(12) United States Patent
Kosuge et al.

(10) Patent No.: US 10,038,152 B2
(45) Date of Patent: Jul. 31, 2018

(54) ORGANIC LIGHT-EMITTING ELEMENT

(71) Applicant: CANON KABUSHIKI KAISHA, Tokyo (JP)

(72) Inventors: Tetsuya Kosuge, Yokohama (JP); Yosuke Nishide, Kawasaki (JP); Hirokazu Miyashita, Tokyo (JP); Shigemoto Abe, Yokohama (JP); Takayuki Horiuchi, Tokyo (JP); Naoki Yamada, Inagi (JP); Jun Kamatani, Tokyo (JP); Akihito Saitoh, Gotemba (JP); Kengo Kishino, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 437 days.

(21) Appl. No.: 14/648,494

(22) PCT Filed: Dec. 24, 2013

(86) PCT No.: PCT/JP2013/085310
§ 371 (c)(1),
(2) Date: May 29, 2015

(87) PCT Pub. No.: WO2014/104386
PCT Pub. Date: Jul. 3, 2014

(65) Prior Publication Data
US 2015/0295188 A1    Oct. 15, 2015

(30) Foreign Application Priority Data

Dec. 27, 2012  (JP) .................................. 2012-285619

(51) Int. Cl.
*H01L 51/00* (2006.01)
*C09K 11/06* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS 6,753,788 B1 * 6/2004 Munyon ............... G06F 1/1622
340/321
6,824,894 B2  11/2004 Takiguchi et al.
(Continued)

FOREIGN PATENT DOCUMENTS

CN    101827834 A    9/2010
CN    102265424 A    11/2011
(Continued)

OTHER PUBLICATIONS

Japanese Office Action issued in counterpart application No. 2012-285619 dated Jul. 14, 2015, along with its English language translation—8 pages.
(Continued)

*Primary Examiner* — Robert S Loewe
(74) *Attorney, Agent, or Firm* — Fitzpatrick, Cella, Harper & Scinto

(57) ABSTRACT

Provided is an organic light-emitting element improved in luminous efficiency and lifetime. The organic light-emitting element includes a pair of electrodes and an organic compound layer placed between the pair of electrodes, in which the organic compound layer includes an iridium complex having a benzo[f]isoquinoline of a specific structure as a ligand and a heterocycle-containing compound of a specific structure.

20 Claims, 1 Drawing Sheet

(51) Int. Cl.
 C07F 15/00 (2006.01)
 H05B 33/14 (2006.01)
 H05B 33/20 (2006.01)
 G03G 15/04 (2006.01)
 G06F 3/041 (2006.01)
 G06F 3/0488 (2013.01)
 G06F 3/0489 (2013.01)
 G09G 3/3208 (2016.01)
 H01L 27/32 (2006.01)
 H05B 33/08 (2006.01)
 H01L 51/50 (2006.01)
 H01L 51/52 (2006.01)

(52) U.S. Cl.
 CPC ........... G03G 15/04 (2013.01); G06F 3/0412
 (2013.01); G06F 3/0489 (2013.01); G06F
 3/04886 (2013.01); G09G 3/3208 (2013.01);
 H01L 27/3248 (2013.01); H01L 51/0052
 (2013.01); H01L 51/0054 (2013.01); H01L
 51/0058 (2013.01); H01L 51/0073 (2013.01);
 H01L 51/0074 (2013.01); H05B 33/0812
 (2013.01); H05B 33/14 (2013.01); H05B
 33/20 (2013.01); C09K 2211/1007 (2013.01);
 C09K 2211/1011 (2013.01); C09K 2211/1014
 (2013.01); C09K 2211/1029 (2013.01); C09K
 2211/1092 (2013.01); C09K 2211/185
 (2013.01); G06F 2203/04101 (2013.01); G06F
 2203/04803 (2013.01); H01L 51/5016
 (2013.01); H01L 51/5028 (2013.01); H01L
 51/5056 (2013.01); H01L 51/5072 (2013.01);
 H01L 51/5096 (2013.01); H01L 51/5206
 (2013.01); H01L 51/5221 (2013.01); H01L
 2251/301 (2013.01); H01L 2251/308 (2013.01)

(56) References Cited

U.S. PATENT DOCUMENTS

| | | | |
|---|---|---|---|
| 7,078,115 B2 | 7/2006 | Takiguchi et al. | |
| 7,232,618 B2 | 6/2007 | Yamada et al. | |
| 7,976,958 B2 | 7/2011 | Takiguchi et al. | |
| 8,268,455 B2 | 9/2012 | Kamatani et al. | |
| 8,330,153 B2 | 12/2012 | Ooishi et al. | |
| 8,367,850 B2 | 2/2013 | Ma et al. | |
| 8,822,708 B2 | 9/2014 | Ma et al. | |
| 9,153,786 B2 | 10/2015 | Ma et al. | |
| 2003/0215668 A1* | 11/2003 | Kondakov | C09K 11/06 428/690 |
| 2005/0052373 A1* | 3/2005 | Devos | G06F 3/1446 345/82 |
| 2006/0066529 A1* | 3/2006 | Kanda | B41J 2/45 345/76 |
| 2006/0120357 A1* | 6/2006 | Kawasaki | G09G 3/325 370/354 |
| 2007/0231601 A1 | 10/2007 | Nakasu et al. | |
| 2008/0210930 A1 | 9/2008 | Kamatani et al. | |
| 2009/0039776 A1 | 2/2009 | Yamada et al. | |
| 2009/0134784 A1 | 5/2009 | Lin et al. | |
| 2009/0153034 A1 | 6/2009 | Lin et al. | |
| 2010/0219407 A1 | 9/2010 | Kamatani et al. | |
| 2010/0237334 A1 | 9/2010 | Ma et al. | |
| 2011/0084599 A1 | 4/2011 | Brooks et al. | |
| 2011/0102136 A1* | 5/2011 | Nakashima | G06F 1/263 340/5.8 |
| 2011/0315965 A1 | 12/2011 | Takashima et al. | |
| 2012/0181518 A1* | 7/2012 | Ogiwara | H01L 51/5004 257/40 |
| 2012/0211701 A1* | 8/2012 | Spreitzer | C07B 59/00 252/301.16 |
| 2013/0175510 A1 | 7/2013 | Ma et al. | |
| 2013/0207540 A1 | 8/2013 | Itai et al. | |
| 2014/0027757 A1 | 1/2014 | Yamada et al. | |
| 2014/0159005 A1 | 6/2014 | Kawamura et al. | |
| 2014/0326977 A1 | 11/2014 | Ma et al. | |
| 2015/0005512 A1 | 1/2015 | Kawamura et al. | |
| 2015/0194609 A1* | 7/2015 | Nishide | C07D 405/14 257/40 |
| 2015/0372243 A1 | 12/2015 | Ma et al. | |

FOREIGN PATENT DOCUMENTS

| | | |
|---|---|---|
| JP | 2009-114137 A | 5/2009 |
| JP | 2010-93048 A | 4/2010 |
| JP | 2010-535809 A | 11/2010 |
| JP | 2012-19173 A | 1/2012 |
| JP | 2012-229195 A | 11/2012 |
| JP | 2012-240952 A | 12/2012 |
| WO | 2009/021126 A2 | 2/2009 |
| WO | 2010/028151 A1 | 3/2010 |
| WO | 2010/074087 A1 | 7/2010 |
| WO | 2010/137285 A1 | 12/2010 |
| WO | 2012/005361 A1 | 1/2012 |

OTHER PUBLICATIONS

Pending U.S. Appl. No. 14/758,683, filed Jun. 30, 2015.
Pending U.S. Appl. No. 14/760,093, filed Jul. 9, 2015.
Pending U.S. Appl. No. 14/648,095, filed May 28, 2015.
Pending U.S. Appl. No. 14/649,048, filed Jun. 2, 2015.
Pending U.S. Appl. No. 141761,049, filed Jul. 15, 2015.
Pending U.S. Appl. No. 14/764,204, filed Jul. 29, 2015.
Pending U.S. Appl. No. 14/764,376, filed Jul. 29, 2015.
S. P. Fletcher et al., "Oxidation of p-Aminophenols and Formal Radical Cyclization onto Benzene Rings: Formation of Benzo-Fused Nitrogen Heterocylces," Org. Lett., vol. 7, No. 1, pp. 23-26 (2005).
R. H. Wiley et al., "Substituted 4,7-Phenanthrolines and Benzo[f]quinolines as Scintillation Solutes," J. Org. Chem., vol. 23, pp. 268-271 (1958).
F. Eloy et al., "Sur une methode nouvelle de sythese des aza-2 phenanthrenes (benzo[f]isoquinoleines) (Note de laboratoire)," Chimica Therapeutica, vol. 6, No. 1, pp. 48-49 (1971).
K. R. Roesch et al., "Synthesis of Isoquinolines and Pyridines by the Palladium-Catalyzed Iminoannulation of Internal Alkynes," J. Org. Chem., vol. 66, pp. 8042-8051 (2001).
Y. Terao et al., "Palladium-Catalyzed Cross-Coupling of Benzyl Ketones and alpha,beta-Unsaturated Carbonyl and Phenolic Compounds with o-Dibromobenzenes to Produce Cyclic Products," Bull. Chem. Soc. Jpn., vol. 72, pp. 2345-2350 (1999).
Chinese office action issued in corresponding application 201380067412.0 dated Apr. 22, 2016—17 pages with English translation.

* cited by examiner

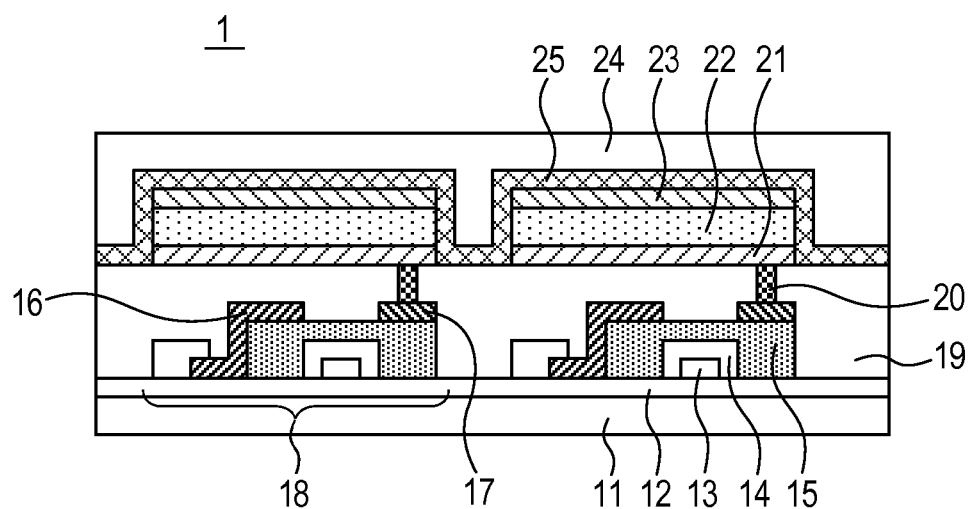

ORGANIC LIGHT-EMITTING ELEMENT

TECHNICAL FIELD

The present invention relates to an organic light-emitting element.

BACKGROUND ART

An organic light-emitting element is an electronic element including an anode and a cathode, and an organic compound layer placed between both the electrodes. A hole and an electron injected from the respective electrodes (the anode and the cathode) recombine in the organic compound layer to produce an exciton, and the organic light-emitting element emits light upon relaxation of the exciton to its ground state. Recent development of the organic light-emitting elements is significant and the developed elements have, for example, the following features. The light-emitting elements can be driven at low voltages, emit light beams having various wavelengths, have high-speed responsiveness, and can be reduced in thickness and weight.

Of the organic light-emitting elements, a phosphorescent light-emitting element utilizing phosphorescence is a light-emitting element that includes a phosphorescent light-emitting material in its organic compound layer and excites the phosphorescent light-emitting material to provide light emission derived from a triplet exciton. However, the phosphorescent light-emitting element has room for additional improvements from the viewpoints of its luminous efficiency and durability lifetime. Specifically, an improvement in emission quantum yield of the phosphorescent light-emitting material and suppression of deterioration of a molecular structure of a host molecule in a light-emitting layer have been main problems.

An iridium complex having a red light-emitting arylbenzo[f]isoquinoline as a ligand (hereinafter described as a biq-based Ir complex) has been known as one phosphorescent light-emitting material having a high emission quantum yield. Patent Literature 1 discloses an organic light-emitting element whose light-emitting layer contains Ir(pbiq)$_3$ (biq-based Ir complex) represented by the following formula as a guest and CBP as a host for an improvement in luminous efficiency.

In addition, Patent Literature 2 discloses an organic light-emitting element whose light-emitting layer contains, as a host, a benzo-fused thiophene or benzo-fused furan compound that is a heterocycle-containing compound.

CITATION LIST

Patent Literature

PTL 1: JP No. 2009-114137A
PTL 2: JP No. 2010-535809A
PTL 3: WO2010/028151
PTL 4: WO2010/137285

Non Patent Literature

NPL 1: J. Org. Chem., Vol. 66, 8042-8051 (2001)
NPL 2: Org. Lett., Vol. 7, No. 1, pp 23-26 (2005)
NPL 3: Chimica Therapeutica, Vol. 6, no. 1, 48-49 (1971), J. Org. Chem., Vol. 23, pp. 268-271 (1958)
NPL 4: Bull. Chem. Soc. Jpn., Vol. 72, 2345-2350 (1999)

SUMMARY OF INVENTION

Solution to Problem

In view of the foregoing, according to one embodiment of the present invention, there is provided an organic light-emitting element, including:

a pair of electrodes; and an organic compound layer placed between the pair of electrodes, in which the organic compound layer has an iridium complex represented by the following general formula [1] and a heterocycle-containing compound represented by the following general formula [5].

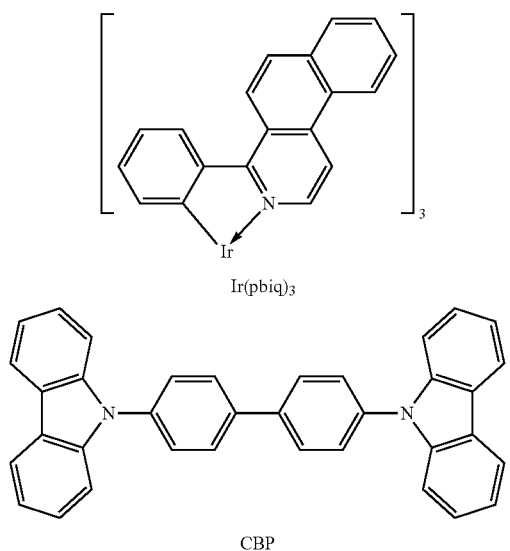

Ir(pbiq)$_3$

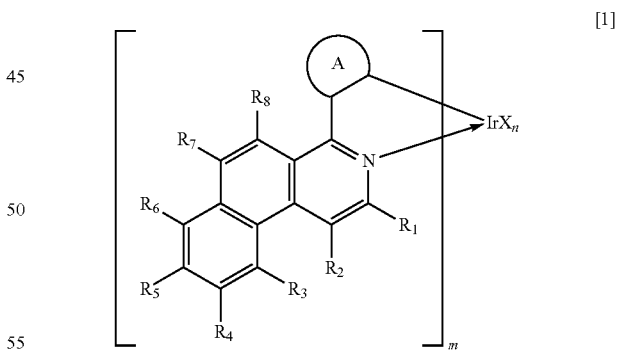

CBP

In the formula [1], $R_1$ to $R_8$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group.

m represents an integer of 1 to 3 and n represents an integer of 0 to 2, provided that m+n equals 3.

A ring A represents a cyclic structure selected from a benzene ring, a naphthalene ring, a fluorene ring, a phenanthrene ring, and a 9,9-spirobifluorene ring, and is covalently bonded to a benzo[f]isoquinoline skeleton and an Ir metal. The ring A may further have a substituent.

X represents a bidentate ligand.

A partial structure $IrX_n$ includes any one of structures represented by the following general formulae [2] to

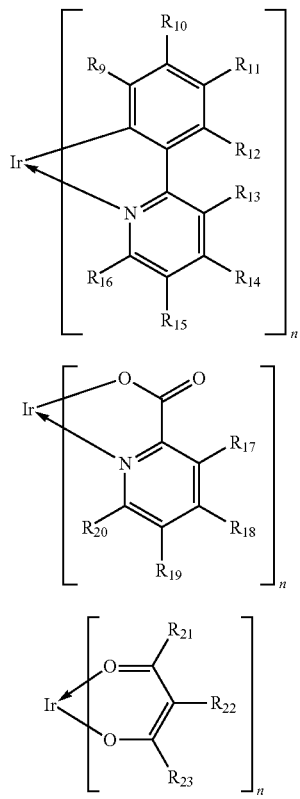

In the formulae [2] to [4], $R_9$ to $R_{23}$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group.

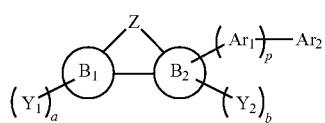

In the formula [5], Z represents an oxygen atom or a sulfur atom.

A ring $B_1$ and a ring $B_2$ each represent a cyclic structure selected from a benzene ring, a naphthalene ring, a phenanthrene ring, a triphenylene ring, and a chrysene ring, and may be identical to or different from each other.

$Y_1$ and $Y_2$ each represent an alkyl group, or a substituted or unsubstituted aromatic hydrocarbon group.

a represents an integer of 0 to 4, and when a represents 2 or more, multiple $Y_1$'s may be identical to or different from each other.

b represents an integer of 0 to 4, provided that when the ring $B_2$ represents a benzene ring, b represents an integer of 0 to 3, and when b represents 2 or more, multiple $Y_2$'s may be identical to or different from each other.

$Ar_1$ represents a substituted or unsubstituted divalent aromatic hydrocarbon group.

$Ar_2$ represents a substituted or unsubstituted monovalent aromatic hydrocarbon group.

p represents an integer of 0 to 4, and when p represents 2 or more, multiple $Ar_1$'s may be identical to or different from each other.

Further features of the present invention will become apparent from the following description of exemplary embodiments with reference to the attached drawing.

BRIEF DESCRIPTION OF DRAWINGS

FIG. 1 is a schematic sectional view illustrating an example of a display apparatus including an organic light-emitting element and a TFT element connected to the organic light-emitting element.

DESCRIPTION OF EMBODIMENTS

However, the high luminous efficiency obtained in the organic light-emitting element described in Patent Literature 1 largely depends on the emission quantum yield of the biq-based Ir complex itself incorporated as the guest into the light-emitting layer. Accordingly, additional contrivance is needed for improving not only the luminous efficiency but also, for example, a lifetime.

In addition, in Patent Literature 2, a green light-emitting iridium complex is incorporated as a guest into the light-emitting layer. However, there is no disclosure of any example in which a red light-emitting iridium complex is used.

The present invention has been made to solve the problems, and an object of the present invention is to provide an organic light-emitting element improved in luminous efficiency and lifetime.

Hereinafter, the present invention is described in detail.

(1) Organic Light-Emitting Element

An organic light-emitting element of the present invention is a light-emitting element including at least: an anode and a cathode as a pair of electrodes opposite to each other; and an organic compound layer placed between the pair of electrodes. In addition, the organic light-emitting element of the present invention includes, in the organic compound layer, an iridium complex represented by the following general formula [1] and a heterocycle-containing compound represented by the following general formula [5].

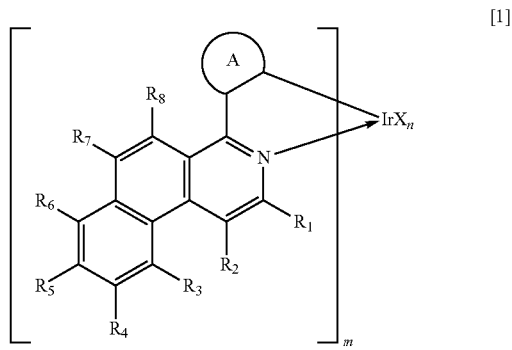

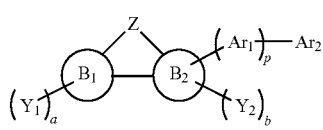

It should be noted that details about the iridium complex represented by the general formula [1] and the heterocycle-containing compound represented by the general formula [5] are described later.

The element construction of the organic light-emitting element of the present invention is, for example, a multilayer-type element construction obtained by sequentially laminating, on a substrate, electrode layers and an organic compound layer described in each of the following constructions (1) to (6). It should be noted that in each of the element constructions, the organic compound layer necessarily includes a light-emitting layer including a light-emitting material.

(1) Anode/light-emitting layer/cathode
(2) Anode/hole-transporting layer/light-emitting layer/electron-transporting layer/cathode
(3) Anode/hole-transporting layer/light-emitting layer/electron-transporting layer/electron-injecting layer/cathode
(4) Anode/hole-injecting layer/hole-transporting layer/light-emitting layer/electron-transporting layer/cathode
(5) Anode/hole-injecting layer/hole-transporting layer/light-emitting layer/electron-transporting layer/electron-injecting layer/cathode
(6) Anode/hole-transporting layer/electron-blocking layer/light-emitting layer/hole-blocking layer/electron-transporting layer/cathode It should be noted that those element construction examples are only very basic element constructions and the element construction of the organic light-emitting element of the present invention is not limited thereto.

For example, the following various layer constructions can each be adopted: an insulating layer, an adhesion layer, or an interference layer is provided at an interface between an electrode and the organic compound layer, the electron-transporting layer or the hole-transporting layer is formed of two layers having different ionization potentials, or the light-emitting layer is formed of two layers including different light-emitting materials.

In the present invention, the aspect according to which light output from the light-emitting layer is extracted (element form) may be the so-called bottom emission system in which the light is extracted from an electrode on a side closer to the substrate or may be the so-called top emission system in which the light is extracted from a side opposite to the substrate. In addition, a double-face extraction system in which the light is extracted from each of the side closer to the substrate and the side opposite to the substrate can be adopted.

Of the element constructions (1) to (6), the construction (6) is preferred because the construction includes both the electron-blocking layer and the hole-blocking layer. In other words, the construction (6) including the electron-blocking layer and the hole-blocking layer provides an organic light-emitting element that does not cause any carrier leakage and has high luminous efficiency because both carriers, i.e., a hole and an electron can be trapped in the light-emitting layer with reliability.

In the organic light-emitting element of the present invention, the iridium complex represented by the general formula [1] and the heterocycle-containing compound represented by the general formula [5] are preferably incorporated into the light-emitting layer out of the organic compound layer. In this case, the light-emitting layer includes at least the iridium complex represented by the general formula [1] and the heterocycle-containing compound represented by the general formula [5]. The applications of the compounds to be incorporated into the light-emitting layer in this case vary depending on their content concentrations in the light-emitting layer. Specifically, the compounds are classified into a main component and a sub-component depending on their content concentrations in the light-emitting layer.

The compound serving as the main component is a compound having the largest weight ratio (content concentration) out of the group of compounds to be incorporated into the light-emitting layer and is a compound also called a host. In addition, the host is a compound present as a matrix around the light-emitting material in the light-emitting layer, and is a compound mainly responsible for the transport of a carrier to the light-emitting material and the donation of an excitation energy to the light-emitting material.

In addition, the compound serving as the sub-component is a compound except the main component and can be called a guest (dopant), a light emission assist material, or a charge-injecting material depending on a function of the compound. The guest as one kind of sub-component is a compound (light-emitting material) responsible for main light emission in the light-emitting layer. The light emission assist material as one kind of sub-component is a compound that assists the light emission of the guest, and is a compound having a smaller weight ratio (content concentration) in the light-emitting layer than that of the host. The light emission assist material is also called a second host by virtue of its function. In the present invention, the (light emission) assist material is preferably an iridium complex, provided that the iridium complex to be used as the (light emission) assist material is an iridium complex except the iridium complex represented by the general formula [1].

The concentration of the guest with respect to the host is 0.01 wt % or more and 50 wt % or less, preferably 0.1 wt % or more and 20 wt % or less with reference to the total amount of the constituent materials for the light-emitting layer. The concentration of the guest is particularly preferably 10 wt % or less from the viewpoint of preventing concentration quenching.

In the present invention, the guest may be uniformly incorporated into the entirety of the layer in which the host serves as a matrix, or may be incorporated so as to have a concentration gradient. In addition, the guest may be partially incorporated into a specific region in the light-emitting layer to make the layer a layer having a region free of the guest and formed only of the host.

In the present invention, the following aspect is preferred: both the iridium complex represented by the general formula [1] and the heterocycle-containing compound represented by the general formula [5] are incorporated as the guest and the host, respectively, into the light-emitting layer. In this case, in addition to the iridium complex represented by the general formula [1], another phosphorescent light-emitting material may be further incorporated into the light-emitting layer for assisting the transfer of an exciton or a carrier.

In addition, a compound different from the heterocycle-containing compound represented by the general formula [5] may be further incorporated as the second host into the light-emitting layer for assisting the transfer of the exciton or the carrier.

(2) Iridium Complex

Next, the iridium complex as one constituent material for the organic light-emitting element of the present invention is described. The iridium complex as one constituent material for the organic light-emitting element of the present invention is a compound represented by the following general formula [1].

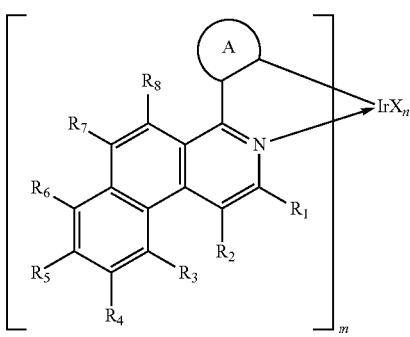

[1]

In the formula [1], $R_1$ to $R_8$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group.

Specific examples of the halogen atom represented by any one of $R_1$ to $R_8$ include fluorine, chlorine, bromine, and iodine atoms.

The alkyl group represented by any one of $R_1$ to $R_8$ is preferably an alkyl group having 1 or more and 6 or less carbon atoms. Specific examples of the alkyl group having 1 or more and 6 or less carbon atoms include a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group. It should be noted that part or all of hydrogen atoms in the alkyl group may be substituted with a fluorine atom as in a trifluoromethyl group or the like. Of those alkyl groups, a methyl group or a tert-butyl group is particularly preferred.

Specific examples of the alkoxy group represented by any one of $R_1$ to $R_8$ include, but, of course, not limited to, a methoxy group, an ethoxy group, an i-propoxy group, an n-butoxy group, and a tert-butoxy group. Of those alkoxy groups, a methoxy group or an ethoxy group is preferred.

Specific examples of the aromatic hydrocarbon group represented by any one of $R_1$ to $R_8$ include, but, of course, not limited to, a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group. Of those aromatic hydrocarbon groups, a phenyl group, a naphthyl group, a fluorenyl group, or a biphenyl group is preferred, and a phenyl group is more preferred.

Specific examples of the heteroaromatic group represented by any one of $R_1$ to $R_8$ include, but, of course, not limited to, a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group.

The aromatic hydrocarbon group and heteroaromatic group each represented by any one of $R_1$ to $R_8$ may further have a substituent. Specific examples thereof include: alkyl groups such as a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group; a halogen atom selected from fluorine, chlorine, bromine, and iodine atoms; alkoxy groups such as a methoxy group, an ethoxy group, an i-propoxy group, an n-butoxy group, and a tert-butoxy group; substituted amino groups such as an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl) amino group, and an N-phenyl-N-(4-trifluoromethylphenyl) amino group; aromatic hydrocarbon groups such as a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group; heteroaromatic groups such as a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group; a cyano group; and a trifluoromethyl group. Of those substitutents, a methyl group, a tert-butyl group, a phenyl group, a naphthyl group, a fluorenyl group, or a biphenyl group is preferred, and a phenyl group is more preferred.

In the formula [1], m represents an integer of 1 to 3 and n represents an integer of 0 to 2, provided that m+n equals 3.

In the formula [1], the ring A represents a cyclic structure selected from a benzene ring, a naphthalene ring, a fluorene ring, a phenanthrene ring, and a 9,9-spirobifluorene ring. The ring A is bonded to a benzo[f]isoquinoline skeleton and an Ir metal with respective covalent bonds.

It should be noted that the ring A may further have a substituent. Specific examples thereof include: alkyl groups such as a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group; a halogen atom selected from fluorine, chlorine, bromine, and iodine atoms; alkoxy groups such as a methoxy group, an ethoxy group, an i-propoxy group, an n-butoxy group, and a tert-butoxy group; substituted amino groups such as an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl) amino group, and an N-phenyl-N-(4-trifluoromethylphenyl) amino group; aromatic hydrocarbon groups such as a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, a terphenyl group, a dimethylphenyl group, a tert-butylphenyl group, a cyanophenyl group, a trifluoromethylphenyl group, and a methoxyphenyl group; heteroaromatic groups such as a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, an oxadiazolyl group, and a dimethylpyridyl group; a cyano group; and a trifluoromethyl group.

In the formula [1], X represents a bidentate ligand. In the present invention, a partial structure $IrX_n$ of the complex including X is specifically any one of the structures represented by the following general formulae [2] to [4].

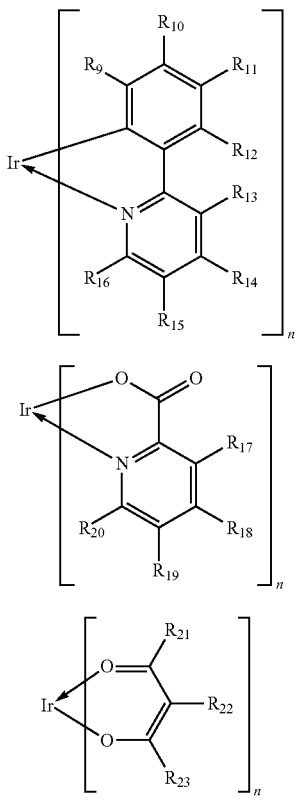

In the formulae [2] to [4], $R_9$ to $R_{23}$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group.

Specific examples of the halogen atom, alkyl group, alkoxy group, trifluoromethyl group, cyano group, aromatic hydrocarbon group, and heteroaromatic group represented by $R_9$ to $R_{23}$ are the same as the specific examples in $R_1$ to $R_8$ in the general formula [1]. In addition, when the substituent represented by any one of $R_9$ to $R_{23}$ is an aromatic hydrocarbon group or a heteroaromatic group, specific examples of the substituent that the substituent may further have are the same as the specific examples in $R_1$ to $R_8$ in the general formula [1].

In the iridium complex represented by the general formula [1], m preferably represents 2 and n preferably represents 1.

In addition, the iridium complex represented by the general formula [1] is preferably an iridium complex represented by the following general formula [6].

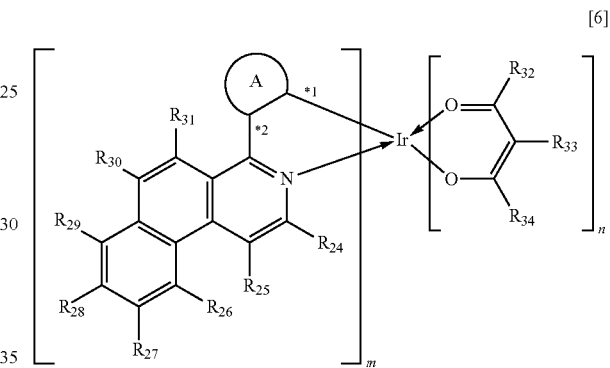

In the formula [6], $R_{24}$ to $R_{34}$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group.

Specific examples of the halogen atom, alkyl group, alkoxy group, trifluoromethyl group, cyano group, aromatic hydrocarbon group, and heteroaromatic group represented by $R_{24}$ to $R_{34}$ are the same as the specific examples of $R_1$ to $R_8$ in the general formula [1]. In addition, when the substituent represented by any one of $R_{24}$ to $R_{34}$ is an aromatic hydrocarbon group or a heteroaromatic group, specific examples of the substituent that the aromatic hydrocarbon group and the heteroaromatic group may each further have are the same as the specific examples of $R_1$ to $R_8$ in the general formula [1].

In the formula [6], m represents an integer of 1 to 3 and n represents an integer of 0 to 2, provided that m+n equals 3.

In the formula [6], *1 represents a bond between the ring A and the Ir metal and *2 represents a bond between the ring A and a carbon atom at the 4-position of the benzo[f]isoquinoline skeleton.

In the formula [6], the ring A is a substituted or unsubstituted aromatic ring, is specifically a partial structure represented by any one of the following general formulae [7] to [11], and is preferably a structure represented by the general formula [7].

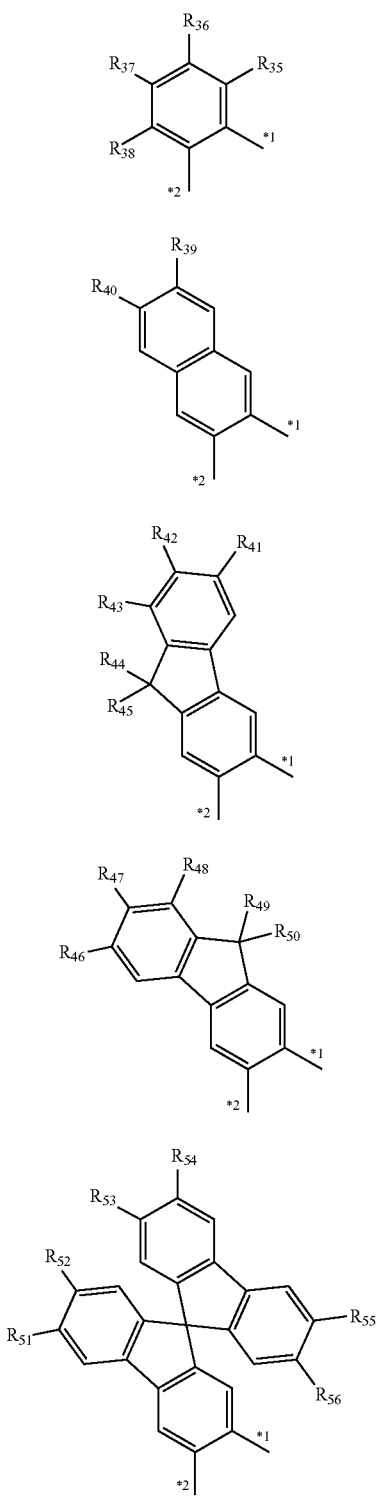

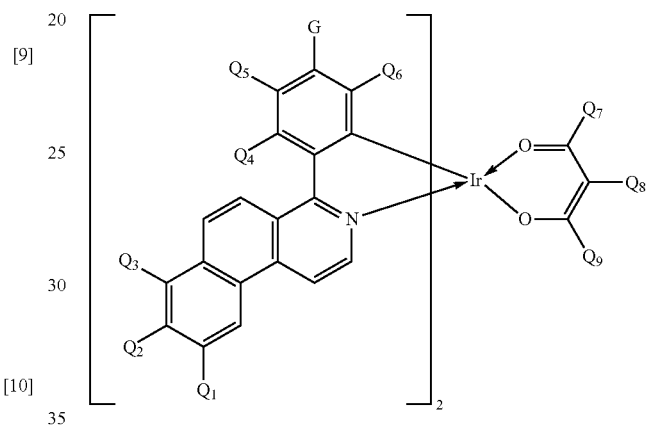

[20]

In the formulae [7] to [11], *1 represents a bonding position with the Ir metal and *2 represents a bonding position with the carbon atom at the 4-position in the benzo[f]isoquinoline skeleton.

In addition, the iridium complex represented by the general formula [1] is particularly preferably an iridium complex represented by the following general formula [20].

In the formula [20], $Q_1$ to $Q_9$ each represent a hydrogen atom, a halogen atom, an alkyl group, an alkoxy group, a trifluoromethyl group, or a cyano group. Specific examples of the halogen atom, alkyl group, and alkoxy group represented by $Q_1$ to $Q_9$ are the same as the specific examples in $R_1$ to $R_8$ in the general formula [1].

In the formula [20], G represents a hydrogen atom, a halogen atom, an alkyl group, an alkoxy group, a trifluoromethyl group, a cyano group, or a substituted or unsubstituted phenyl group. Specific examples of the halogen atom, alkyl group, alkoxy group, the phenyl group and their substituent represented by G are the same as the specific examples in $R_1$ to $R_8$ in the general formula [1].

(3) Heterocycle-Containing Compound

Next, the heterocycle-containing compound to be used as the host for the light-emitting layer of the organic light-emitting element of the present invention is described. The heterocycle-containing compound in the organic light-emitting element of the present invention is specifically a compound represented by the following general formula [5].

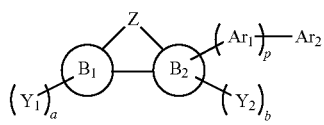

[5]

In the formulae [7] to [11], $R_{35}$ to $R_{56}$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group.

Specific examples of the halogen atom, alkyl group, alkoxy group, trifluoromethyl group, cyano group, aromatic hydrocarbon group, and heteroaromatic group represented by $R_{35}$ to $R_{56}$ are the same as the specific examples of $R_1$ to $R_8$ in the general formula [1]. In addition, when the substituent represented by any one of $R_{35}$ to $R_{56}$ is an aromatic hydrocarbon group or a heteroaromatic group, specific examples of the substituent that the substituent may further have are the same as the specific examples of $R_1$ to $R_8$ in the general formula [1].

In the formula [5], Z represents an oxygen atom or a sulfur atom.

In the formula [5], a ring $B_1$ and a ring $B_2$ each represent a cyclic structure selected from a benzene ring, a naphthalene ring, a phenanthrene ring, a triphenylene ring, and a chrysene ring. That is, the compound represented by the general formula [5] has a heterocycle formed of Z, the ring $B_1$, and the ring $B_2$. In the formula, the ring $B_1$ and the ring $B_2$ may be identical to or different from each other.

It should be noted that the ring $B_1$ and the ring $B_2$ each have the following substituent group, i.e., $Y_1$, $Y_2$, and —$(Ar_1)_p$—$Ar_2$.

In the formula [5], $Y_1$ and $Y_2$ each represent an alkyl group or a substituted or unsubstituted aromatic hydrocarbon group.

The alkyl group represented by $Y_1$ or $Y_2$ is preferably an alkyl group having 1 or more and 6 or less carbon atoms. Specific examples of the alkyl group having 1 or more and 6 or less carbon atoms include a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group. Of those alkyl groups, a methyl group or a tert-butyl group is particularly preferred.

Specific examples of the aromatic hydrocarbon group represented by $Y_1$ or $Y_2$ include, but, of course, not limited to, a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group. Of those aromatic hydrocarbon groups, a phenyl group, a naphthyl group, a fluorenyl group, or a biphenyl group is preferred, and a phenyl group is more preferred.

Specific examples of the substituent that the aromatic hydrocarbon group may further have include: alkyl groups such as a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group; a halogen atom selected from fluorine, chlorine, bromine, and iodine atoms; alkoxy groups such as a methoxy group, an ethoxy group, an i-propoxy group, an n-butoxy group, and a tert-butoxy group; substituted amino groups such as an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group; aromatic hydrocarbon groups such as a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group; heteroaromatic groups such as a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group; a cyano group; and a trifluoromethyl group. Of those substituents, a methyl group, a tert-butyl group, a phenyl group, a naphthyl group, a fluorenyl group, or a biphenyl group is preferred, and a phenyl group is more preferred.

In the formula [5], a represents an integer of 0 to 4, and when a represents 2 or more, multiple $Y_1$'s may be identical to or different from each other.

In the formula [5], b represents an integer of 0 to 4, and when the ring $B_2$ represents a benzene ring, b represents an integer of 0 to 3. When b represents 2 or more, multiple $Y_2$'s may be identical to or different from each other.

In the formula [5], $Ar_1$ represents a substituted or unsubstituted divalent aromatic hydrocarbon group. Specific examples thereof include a phenylene group, a biphenylene group, a terphenylene group, a naphthalenediyl group, a phenanthrenediyl group, an anthracenediyl group, a benzo[a]anthracenediyl group, a fluorenediyl group, a benzo[a]fluorenediyl group, a benzo[b]fluorenediyl group, a benzo[c]fluorenediyl group, a dibenzo[a,c]fluorenediyl group, a dibenzo[b,h]fluorenediyl group, a dibenzo[c,g]fluorenediyl group, a biphenylenediyl group, an acenaphthylenediyl group, a chrysenediyl group, a benzo[b]chrysenediyl group, a pyrenediyl group, a benzo[e]pyrenediyl group, a triphenylenediyl group, a benzo[a]triphenylenediyl group, a benzo[b]triphenylenediyl group, a picenediyl group, a fluoranthenediyl group, a benzo[a]fluoranthenediyl group, a benzo[b]fluoranthenediyl group, a benzo[j]fluoranthenediyl group, a benzo[k]fluoranthenediyl group, a perylenediyl group, and a naphthacenediyl group. Of those, a phenylene group, a biphenylene group, a terphenylene group, a naphthalenediyl group, a fluorenediyl group, a phenanthrenediyl group, a chrysenediyl group, or a triphenylenediyl group is preferred.

Specific examples of the substituent that the divalent aromatic hydrocarbon group represented by $Ar_1$ may further have include: alkyl groups such as a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group; a halogen atom selected from fluorine, chlorine, bromine, and iodine atoms; alkoxy groups such as a methoxy group, an ethoxy group, an i-propoxy group, an n-butoxy group, and a tert-butoxy group; substituted amino groups such as an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group; aromatic hydrocarbon groups such as a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group; heteroaromatic groups such as a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group; a cyano group; and a trifluoromethyl group.

In the formula [5], $Ar_2$ represents a substituted or unsubstituted monovalent aromatic hydrocarbon group. Specific examples thereof include a phenyl group, a naphthyl group, a phenanthryl group, an anthryl group, a benzo[a]anthryl group, a fluorenyl group, a benzo[a]fluorenyl group, a benzo[b]fluorenyl group, a benzo[c]fluorenyl group, a dibenzo[a,c]fluorenyl group, a dibenzo[b,h]fluorenyl group, a dibenzo[c,g]fluorenyl group, a biphenylenyl group, an acenaphthylenyl group, a chrysenyl group, a benzo[b]chrysenyl group, a pyrenyl group, a benzo[e]pyrenyl group, a triphenylenyl group, a benzo[a]triphenylenyl group, a benzo[b]triphenylenyl group, a picenyl group, a fluoranthenyl group, a benzo[a]fluoranthenyl group, a benzo[b]fluoranthenyl group, a benzo[j]fluoranthenyl group, a benzo[k]fluoranthenyl group, a perylenyl group, and a naphthacenyl group. Of those, a phenyl group, a biphenyl group, a terphenyl group, a naphthyl group, a fluorenyl group, a phenanthrenyl group, a chrysenyl group, or a triphenylenyl group is preferred.

Specific examples of the substituent that the monovalent aromatic hydrocarbon group represented by $Ar_2$ may further have include: alkyl groups such as a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group; a halogen atom selected from fluorine, chlorine, bromine, and iodine atoms; alkoxy groups such as a methoxy group, an ethoxy group, an i-propoxy group, an n-butoxy group, and a tert-butoxy group; substituted amino groups such as an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group; aromatic hydrocarbon groups such as a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group; heteroaromatic groups such as a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group; a cyano group; and a trifluoromethyl group.

In the formula [5], p represents an integer of 0 to 4, and when p represents 2 or more, multiple $Ar_1$'s may be identical to or different from each other.

In addition, in the heterocycle-containing compound represented by the general formula [5], the heterocycle formed of Z, the ring $B_1$, and the ring $B_2$ is preferably selected from heterocycles represented by the following general formulae [12] to [19].

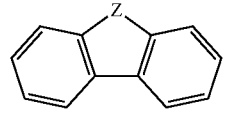

[12]

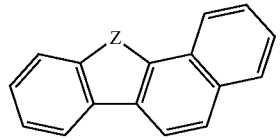

[13]

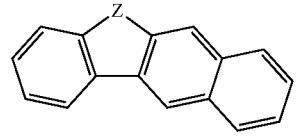

[14]

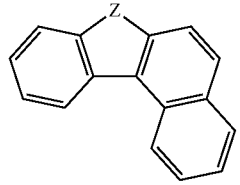

[15]

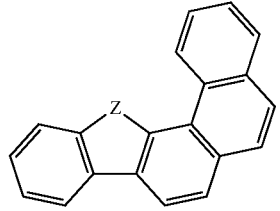

[16]

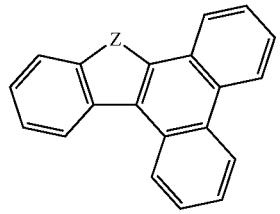

[17]

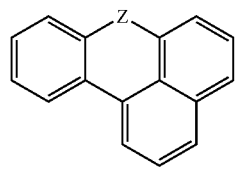

[18]

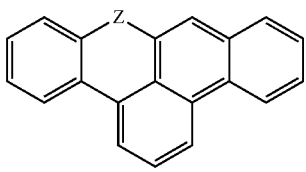

[19]

In the formulae [12] to [19], Z represents an oxygen atom or a sulfur atom.

Dibenzothiophene, benzonaphthothiophene, benzophenanthrothiophene, or dibenzoxanthene is more preferred as the heterocycle formed of Z, the ring $B_1$, and the ring $B_2$.

Any one of compounds represented by the following general formulae [21] to [25] is particularly preferred as the heterocycle-containing compound represented by the general formula [5].

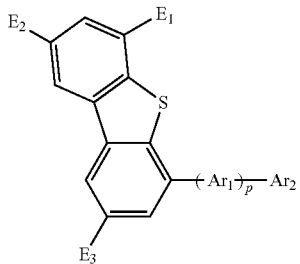

[21]

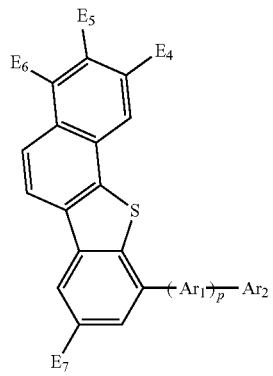

[22]

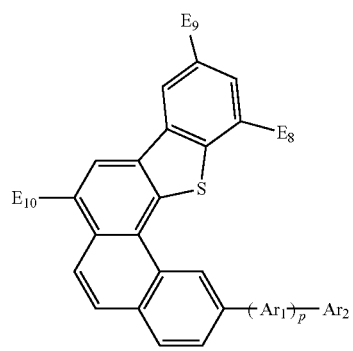

[23]

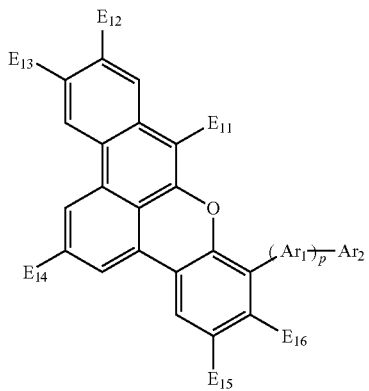

[24]

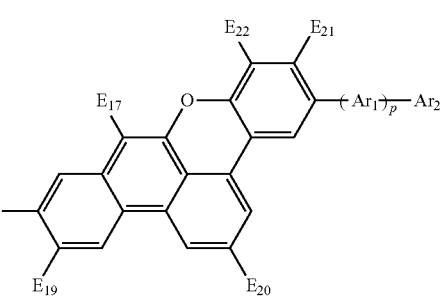

[25]

In the formula [21], $E_1$ to $E_3$ each represent a hydrogen atom, an alkyl group, or a substituted or unsubstituted aromatic hydrocarbon group. Specific examples of the alkyl group and aromatic hydrocarbon group represented by $E_1$ and $E_2$, and the substituent that the aromatic hydrocarbon group may further have are the same as the specific examples of $Y_1$ in the general formula [5]. An alkyl group having 1 or more and 6 or less carbon atoms, a phenyl group, a naphthyl group, a fluorenyl group, a biphenyl group, or a terphenyl group is preferred, and a methyl group, a tert-butyl group, or a phenyl group is more preferred. In addition, specific examples of the alkyl group and aromatic hydrocarbon group represented by $E_3$, and the substituent that the aromatic hydrocarbon group may further have are the same as the specific examples of $Y_2$ in the general formula [5]. An alkyl group having 1 or more and 6 or less carbon atoms, a phenyl group, a naphthyl group, a fluorenyl group, a biphenyl group, or a terphenyl group is preferred, and a methyl group, a tert-butyl group, or a phenyl group is more preferred.

In the formula [22], $E_4$ to $E_7$ each represent a hydrogen atom, an alkyl group, or a substituted or unsubstituted aromatic hydrocarbon group. Specific examples of the alkyl group and aromatic hydrocarbon group represented by $E_4$ to $E_6$, and the substituent that the aromatic hydrocarbon group may further have are the same as the specific examples of $Y_1$ in the general formula [5]. An alkyl group having 1 or more and 6 or less carbon atoms, a phenyl group, a naphthyl group, a fluorenyl group, a biphenyl group, or a terphenyl group is preferred, and a methyl group, a tert-butyl group, or a phenyl group is more preferred. In addition, specific examples of the alkyl group and aromatic hydrocarbon group represented by $E_7$, and the substituent that the aromatic hydrocarbon group may further have are the same as the specific examples of $Y_2$ in the general formula [5]. An alkyl group having 1 or more and 6 or less carbon atoms, a phenyl group, a naphthyl group, a fluorenyl group, a biphenyl group, or a terphenyl group is preferred, and a methyl group, a tert-butyl group, or a phenyl group is more preferred.

In the formula [23], $E_8$ to $E_{10}$ each represent a hydrogen atom, an alkyl group, or a substituted or unsubstituted aromatic hydrocarbon group. Specific examples of the alkyl group and aromatic hydrocarbon group represented by $E_8$ and $E_9$, and the substituent that the aromatic hydrocarbon group may further have are the same as the specific examples of $Y_1$ in the general formula [5]. An alkyl group having 1 or more and 6 or less carbon atoms, a phenyl group, a naphthyl group, a fluorenyl group, a biphenyl group, or a terphenyl group is preferred, and a methyl group, a tert-butyl group, or a phenyl group is more preferred. In addition, specific examples of the alkyl group and aromatic hydrocarbon group represented by $E_{10}$, and the substituent that the aromatic hydrocarbon group may further have are the same as the specific examples of $Y_2$ in the general formula [5]. An alkyl group having 1 or more and 6 or less carbon atoms, a phenyl group, a naphthyl group, a fluorenyl group, a biphenyl group, or a terphenyl group is preferred, and a methyl group, a tert-butyl group, or a phenyl group is more preferred.

In the formula [24], $E_{11}$ to $E_{16}$ each represent a hydrogen atom, an alkyl group, or a substituted or unsubstituted aromatic hydrocarbon group. Specific examples of the alkyl group and aromatic hydrocarbon group represented by $E_{11}$ to $E_{14}$, and the substituent that the aromatic hydrocarbon group may further have are the same as the specific examples of $Y_1$ in the general formula [5]. An alkyl group having 1 or more and 6 or less carbon atoms, a phenyl group, a naphthyl group, a fluorenyl group, a biphenyl group, or a terphenyl group is preferred, and a methyl group, a tert-butyl group, or a phenyl group is more preferred. In addition, specific examples of the alkyl group and aromatic hydrocarbon group represented by $E_{15}$ and $E_{16}$, and the substituent that the aromatic hydrocarbon group may further have are the same as the specific examples of $Y_2$ in the general formula [5]. An alkyl group having 1 or more and 6 or less carbon atoms, a phenyl group, a naphthyl group, a fluorenyl group, a biphenyl group, or a terphenyl group is preferred, and a methyl group, a tert-butyl group, or a phenyl group is more preferred.

In the formula [25], $E_{17}$ to $E_{22}$ each represent a hydrogen atom, an alkyl group, or a substituted or unsubstituted aromatic hydrocarbon group. Specific examples of the alkyl group and aromatic hydrocarbon group represented by $E_{17}$ to $E_{20}$, and the substituent that the aromatic hydrocarbon group may further have are the same as the specific examples of $Y_1$ in the general formula [5]. An alkyl group having 1 or more and 6 or less carbon atoms, a phenyl group, a naphthyl group, a fluorenyl group, a biphenyl group, or a terphenyl group is preferred, and a methyl group, a tert-butyl group, or a phenyl group is more preferred. In addition, specific examples of the alkyl group and aromatic hydrocarbon group represented by $E_{21}$ and $E_{22}$, and the substituent that the aromatic hydrocarbon group may further have are the same as the specific examples of $Y_2$ in the general formula [5]. An alkyl group having 1 or more and 6 or less carbon atoms, a phenyl group, a naphthyl group, a fluorenyl group, a biphenyl group, or a terphenyl group is preferred, and a methyl group, a tert-butyl group, or a phenyl group is more preferred.

In the formulae [21] to [25], $E_1$ to $E_{22}$ each preferably represent a hydrogen atom.

In the formulae [21] to [25], $Ar_1$ represents a substituted or unsubstituted divalent aromatic hydrocarbon group. It should be noted that specific examples of $Ar_1$ are the same as the specific examples of $Ar_1$ in the formula [5].

In the formulae [21] to [25], $Ar_2$ represents a substituted or unsubstituted monovalent aromatic hydrocarbon group. It should be noted that specific examples of $Ar_2$ are the same as the specific examples of $Ar_2$ in the formula [5].

In the formulae [21] to [25], p represents an integer of 0 to 4. p preferably represents 1. When p represents 2 or more, multiple $Ar_1$'s may be identical to or different from each other.

In addition, a compound to be used as a constituent material for the organic light-emitting element of the present invention is desirably purified in advance. Sublimation purification is preferred as a method of purifying the compound. This is because the sublimation purification exhibits a large purifying effect in an improvement in purity of an organic compound. In general, in the sublimation purification, heating at higher temperature is needed as the molecular weight of an organic compound to be purified increases, and at that time, its thermal decomposition or the like is liable to occur owing to the high temperature. Therefore, the organic compound to be used as a constituent material for the organic light-emitting element preferably has a molecular weight of 1,500 or less so that the sublimation purification can be performed without excessive heating.

(4) Operations and Effects Exhibited by Host and Guest

As described above, in the organic light-emitting element of the present invention, the organic compound layer (preferably the light-emitting layer) includes both the iridium complex represented by the general formula [1] and the heterocycle-containing compound represented by the general formula [5].

The iridium complex represented by the formula [1] is an organometallic complex in which at least one arylbenzo[f]isoquinoline ligand coordinates to an iridium metal, i.e., a biq-based Ir complex. Here, as described in Patent Literature 1, the biq-based Ir complex is a phosphorescent light-emitting material having a high emission quantum yield and capable of emitting red light. Here, the term "red light emission" refers to such light emission that an emission peak wavelength is 580 nm or more and 650 nm or less, i.e., the lowest triplet excited level ($T_1$) falls within the range of 1.9 eV or more to 2.1 eV or less. In addition, the organic light-emitting element obtained by incorporating the biq-based Ir complex as a guest into the light-emitting layer has extremely high luminous efficiency.

Meanwhile, with regard to the driving durability lifetime of the organic light-emitting element, it has been generally known that the following measures (lifetime-lengthening guidelines) have only to be taken on the light-emitting layer for reducing luminance deterioration to improve the driving durability lifetime:

(I) an improvement in carrier balance in the light-emitting layer;

(II) the extension of a light-emitting region (carrier recombination region); and (III) an improvement in structural stability of a light-emitting layer host material molecule.

That is, the lifetime of the organic light-emitting element can be lengthened by suppressing an element considered to be a factor for the luminance deterioration. Here, with regard to the measure (I), carrier accumulation at an interface between the light-emitting layer and a carrier-transporting layer is suppressed. With regard to the measure (II), local light emission leading to the deterioration of the light-emitting material is suppressed. With regard to the measure (III), the host in the light-emitting layer is prevented from deteriorating to the extent possible.

In addition, the inventors of the present invention have paid attention to the lifetime-lengthening guidelines with regard to the driving durability lifetime of the organic light-emitting element using the big-based Ir complex, and have considered that the driving durability lifetime can be additionally lengthened (a longer lifetime can be achieved) from the viewpoints of the material characteristics of the host in the light-emitting layer. That is, the heterocycle-containing compound represented by the general formula is used instead of CBP used in Patent Literature 1 as the host in the light-emitting layer. Thus, the lifetime of the organic light-emitting element using the big-based Ir complex can be additionally lengthened.

By the way, CBP is a compound having high hole-transporting property because CBP has a carbazole ring. However, in consideration of a combination with the big-based Ir complex to be incorporated as the guest into the light-emitting layer, moderately reducing the hole-transporting property of the host was considered to exhibit large effects on the measure (I) (the improvement in carrier balance) and the measure (II) (the extension of the light-emitting region).

Then, as a result of their extensive studies, the inventors of the present invention have found that a compound having a heterocycle containing oxygen or sulfur in its molecular structure, the compound being a material having moderately low hole-transporting property, is suitable as a host for the big-based Ir complex (guest). The compound can have moderately low hole-transporting property probably because a hole is moderately trapped by the oxygen or sulfur atom on the heterocycle.

Further, CBP contains, in its molecular structure, a bond having low bonding stability (an unstable bond owing to its small bonding energy), specifically a nitrogen-carbon bond that bonds a carbazole ring and a phenylene group. When a compound having such a bond having a small bonding energy is incorporated as a host into the light-emitting layer of an organic light-emitting element, the deterioration of the structure of the compound is liable to occur at the time of the driving of the element and hence there is a high possibility that the durability lifetime of the light-emitting element is adversely affected.

In contrast, the heterocycle-containing compound represented by the general formula [5] does not contain the bond having a small bonding energy. Shown below is comparison between calculated values for the bonding energies of CBP and Exemplified Compound H-308 as a typical example of the heterocycle-containing compound represented by the general formula [5]. It should be noted that the calculation was performed by employing an approach "b3-lyp/def2-SV(P)".

Bonding energy (calculated value)

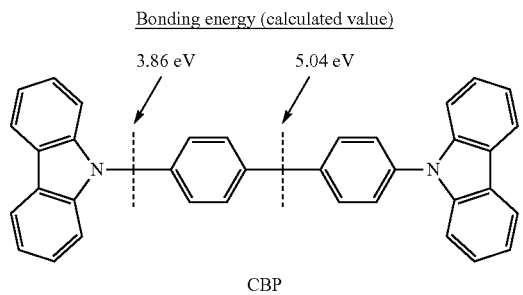

CBP

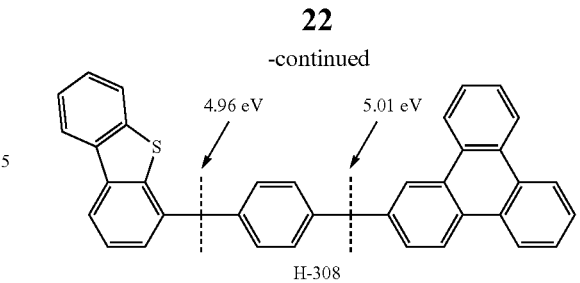

H-308

In Exemplified Compound H-308 as a typical example of the heterocycle-containing compound represented by the general formula [5], a heterocycle and an aromatic hydrocarbon group are bonded to each other by a carbon-carbon bond. Accordingly, the bonding energy is as large as about 5 eV and hence bonding stability is high. On the other hand, in a carbazole derivative such as CBP, carbazole and an aromatic hydrocarbon group are bonded to each other by a nitrogen-carbon bond. Accordingly, the bonding energy is as small as less than 4 eV and hence bonding stability is low. Therefore, the incorporation of the heterocycle-containing compound represented by the general formula [5] as the host into the light-emitting layer can suppress material deterioration upon driving of the element because the structural stability of the compound itself is high. It is understood from the foregoing that a large effect is exhibited on the measure (III) (the improvement in structural stability of the host material molecule).

By the way, the heterocycle-containing compound represented by the general formula [5] and an analogue thereof are each incorporated as a host into a light-emitting layer in an organic light-emitting element, the light-emitting layer containing a green phosphorescent light-emitting iridium complex as a guest, in Patent Literature 2 or the like.

Meanwhile, the inventors of the present invention have found that the heterocycle-containing compound represented by the general formula [5] is suitable as a host for the red phosphorescent light-emitting organometallic complex as the guest in the light-emitting layer. This is because the $S_1$ energy value and $T_1$ energy value of the heterocycle-containing compound represented by the general formula [5] are suitable as the host for the guest in the light-emitting layer, the guest emitting red phosphorescence.

That is, the $T_1$ energy of the host is preferably 2.1 eV or more in order that the quenching of a $T_1$ exciton may be prevented. In addition, the $S_1$ energy of the host is desirably as low as possible in order that an increase in driving voltage may be prevented by good carrier injection, and the energy is preferably 3.0 eV or less. In other words, a $\Delta ST$ value as a difference between the $S_1$ energy and the $T_1$ energy is preferably as small as possible. The heterocycle-containing compound represented by the general formula [5] is suitable as the host to be incorporated into the light-emitting layer that emits red phosphorescence because the compound satisfies those requirements.

Accordingly, the organic light-emitting element of the present invention whose organic compound layer (preferably light-emitting layer) contains the iridium complex represented by the general formula [1] as the guest and the heterocycle-containing compound represented by the general formula [5] as the host can efficiently output red phosphorescence. In addition, the organic light-emitting element of the present invention is such an organic light-emitting element that the lifetime of the element itself is long because the element has at least the iridium complex represented by the general formula [1] and the heterocycle-containing compound represented by the general formula [5].
(5) Specific Examples of Iridium Complex
Specific structural formulae of the iridium complex defined by the general formula [1] are exemplified below.
[Group 1 Iridium Complex]
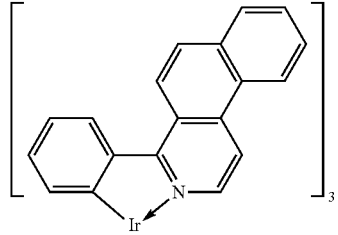
Ir-101
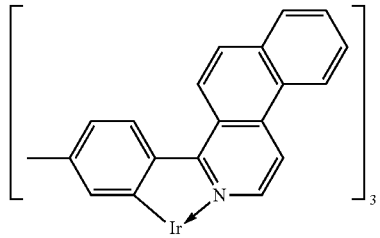
Ir-102
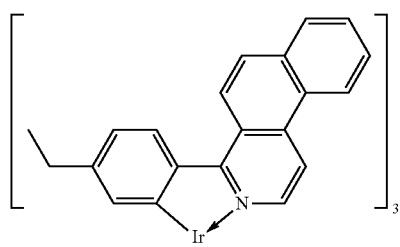
Ir-103
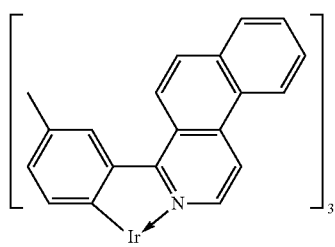
Ir-104
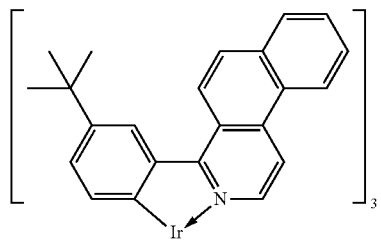
Ir-105
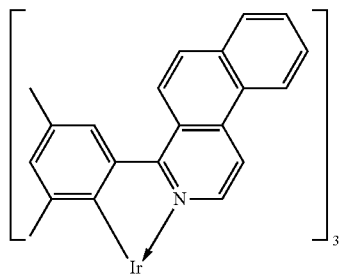
Ir-106
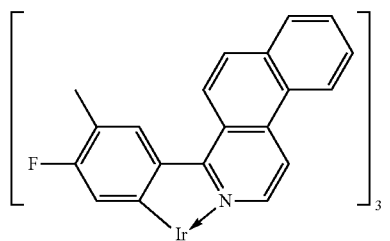
Ir-107
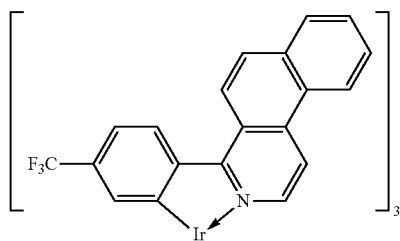
Ir-108
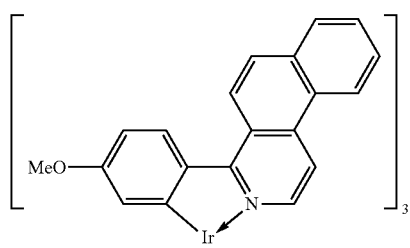
Ir-109
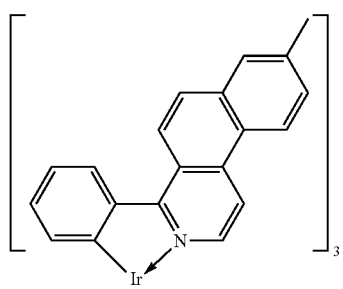
Ir-110

-continued
Ir-111
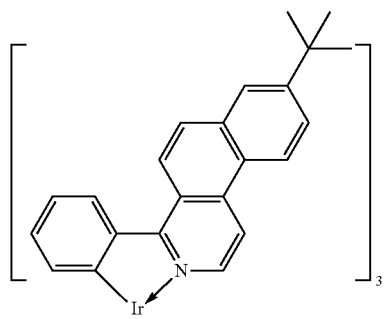
Ir-112
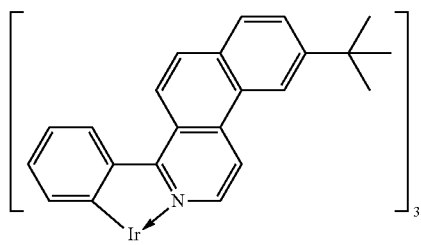
Ir-113
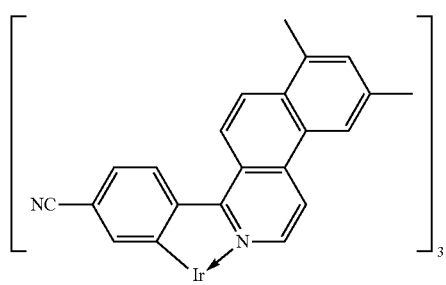
Ir-114
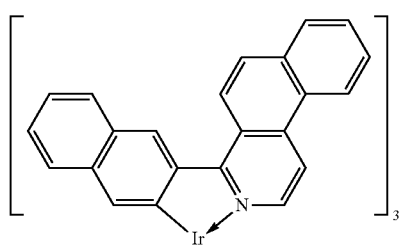
Ir-115
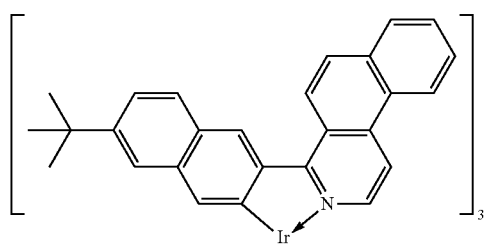
Ir-116
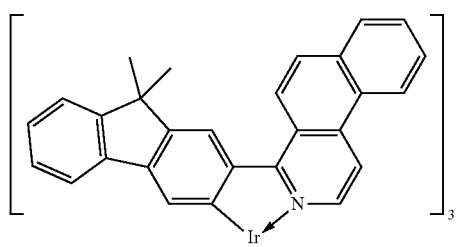
Ir-117
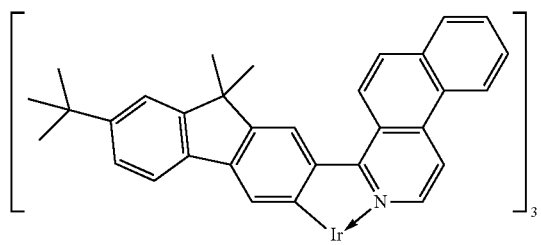
Ir-118
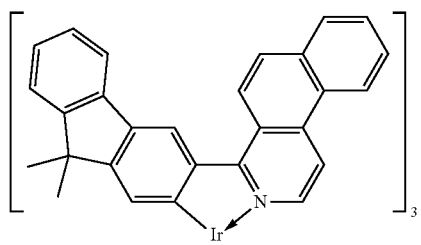
Ir-119
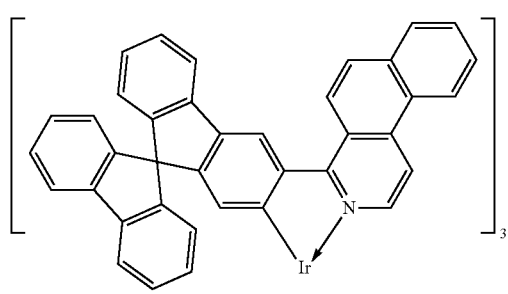
Ir-120
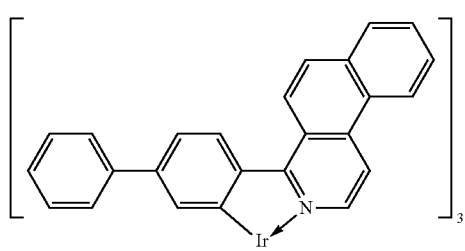

Ir-121 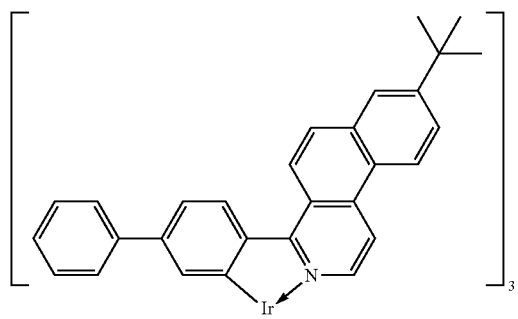
Ir-122 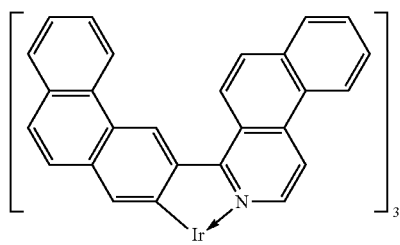
Ir-123 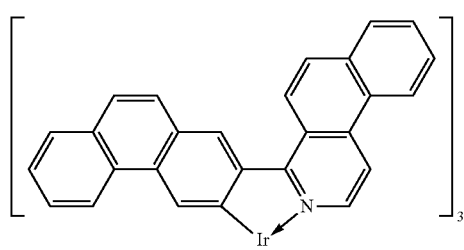
[Group 2 Iridium Complex]
Ir-201 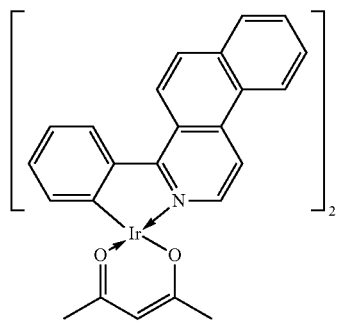
Ir-202 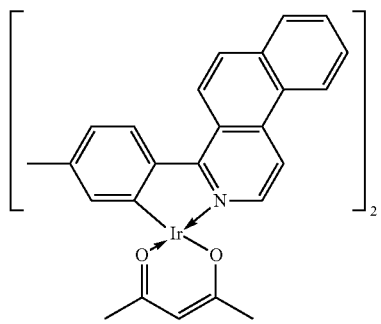
Ir-203 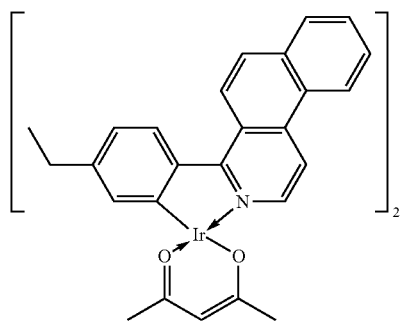
Ir-204 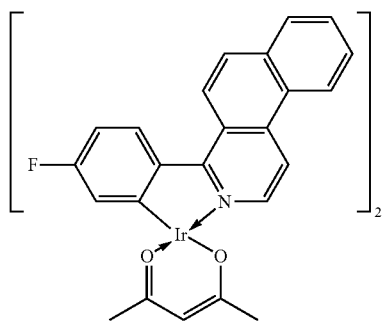
Ir-205 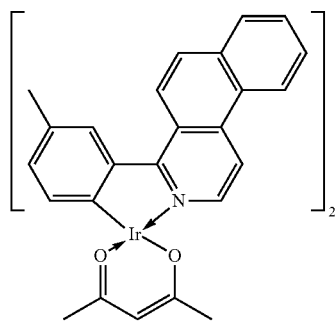
Ir-206 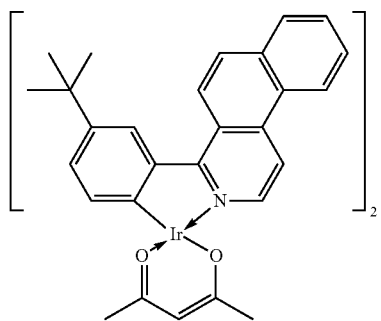

-continued
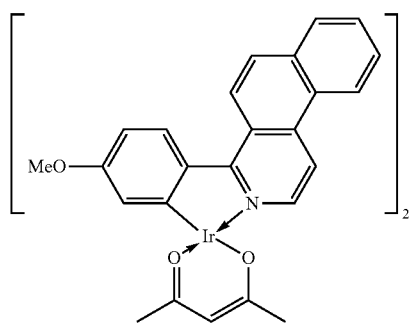
Ir-207
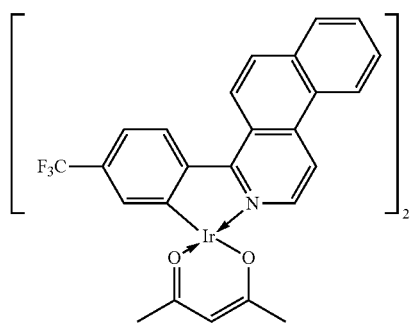
Ir-208
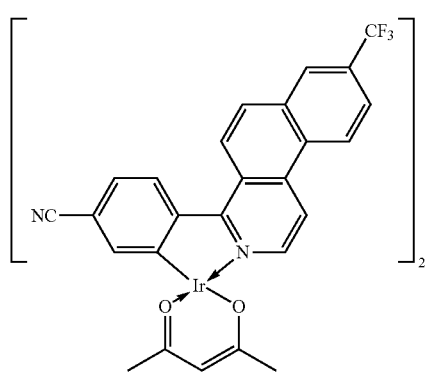
Ir-209
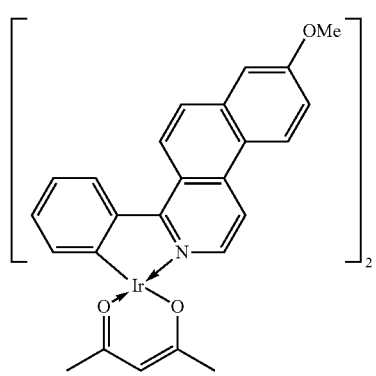
Ir-210
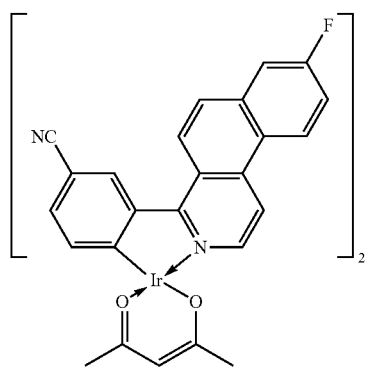
Ir-211
Ir-212
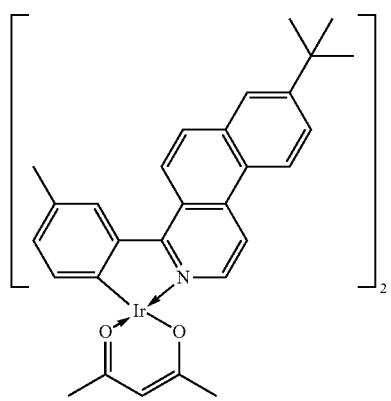
Ir-213
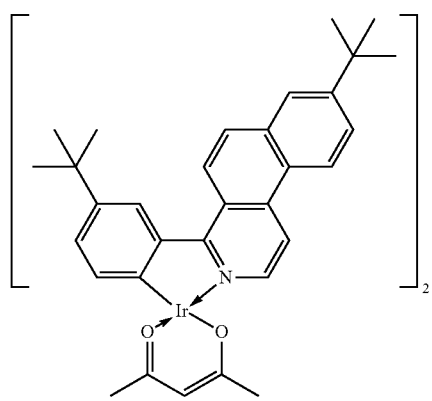
Ir-214

-continued
Ir-215
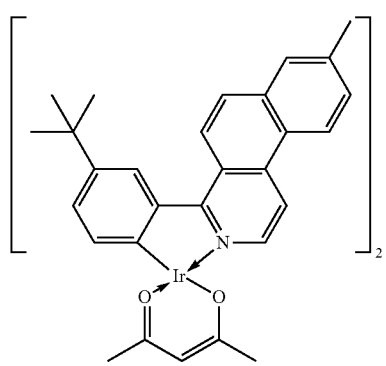
Ir-216
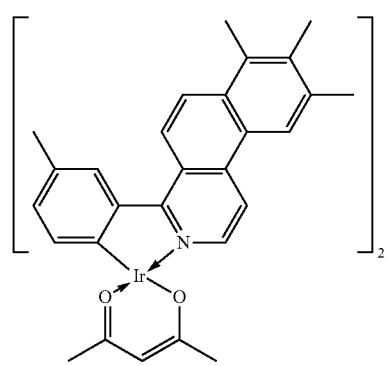
Ir-217
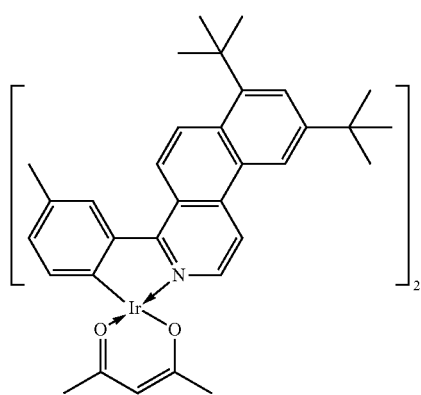
Ir-218
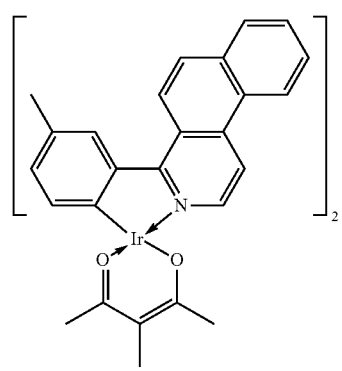
Ir-219
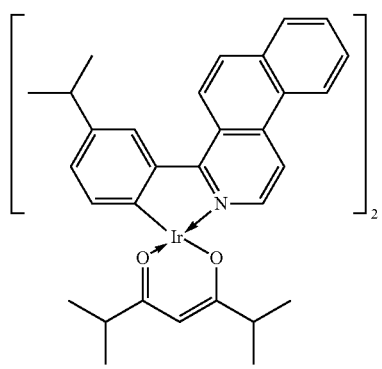
Ir-220
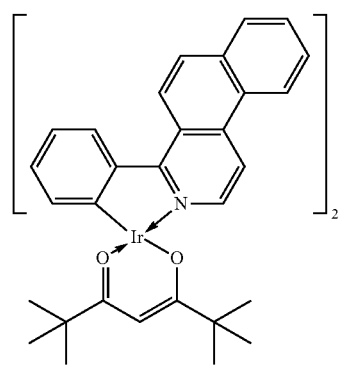
Ir-221
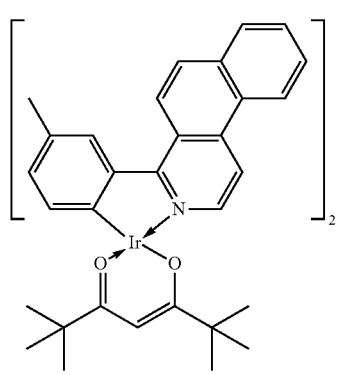
Ir-222
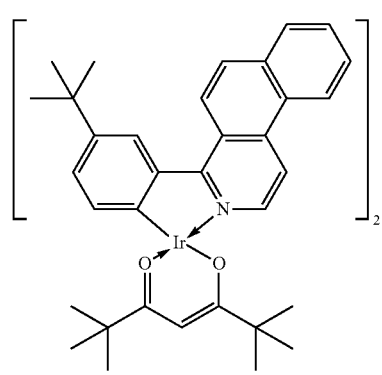

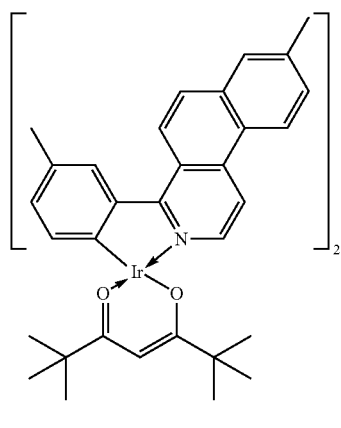
Ir-223
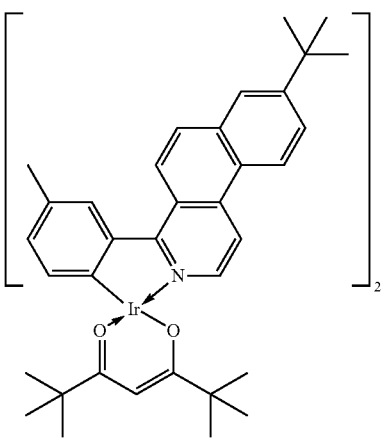
Ir-224
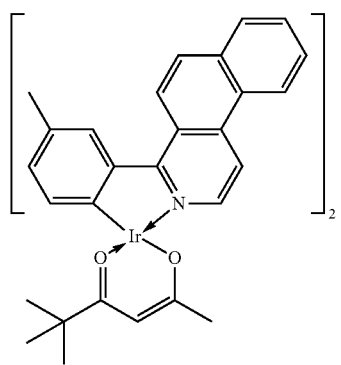
Ir-225
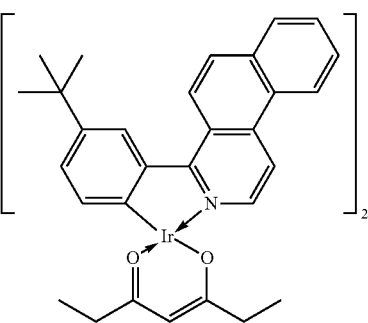
Ir-226
[Group 3 Iridium Complex]
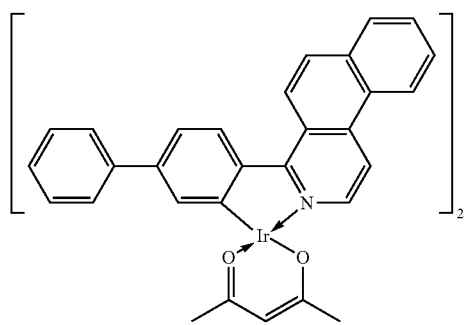
Ir-301
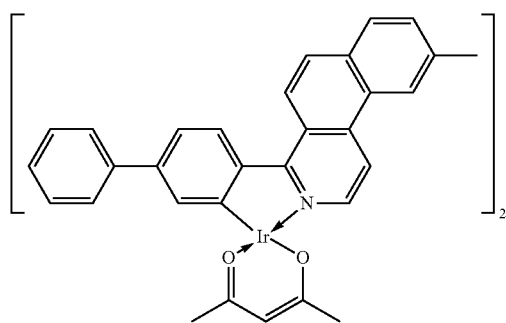
Ir-303
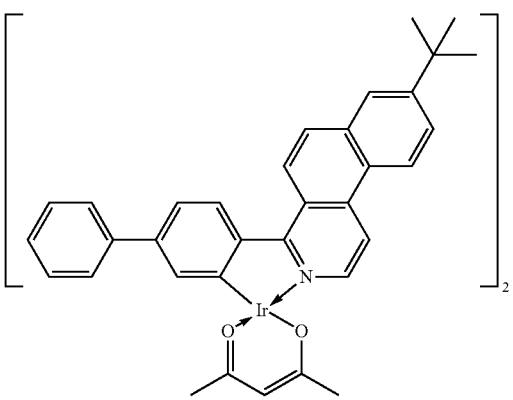
Ir-302
Ir-304

-continued
Ir-305
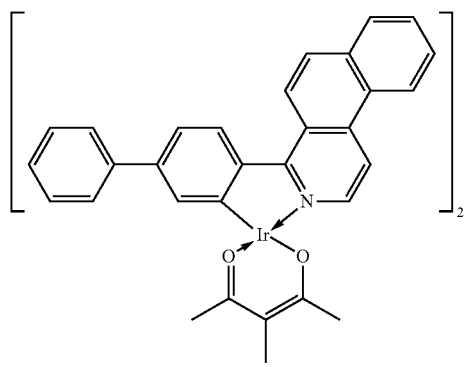
Ir-306
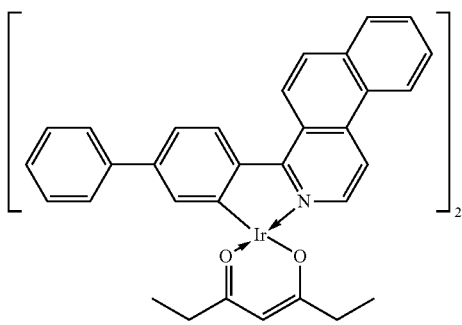
Ir-307
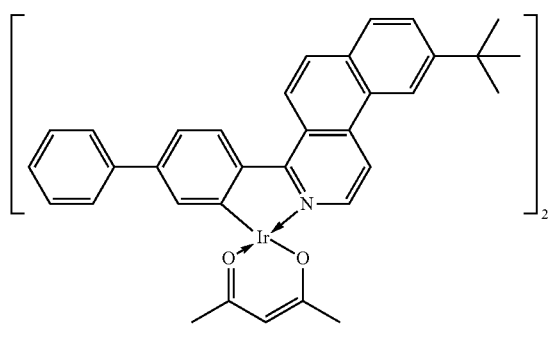
Ir-308
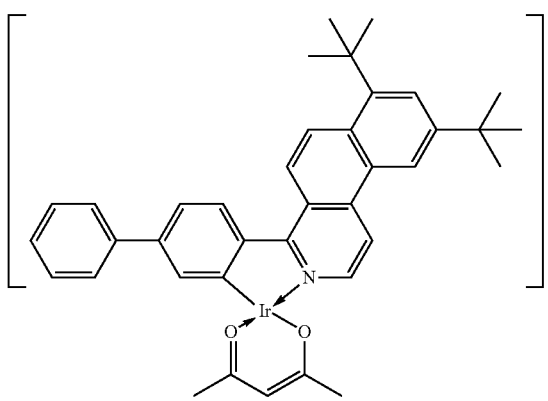
Ir-309
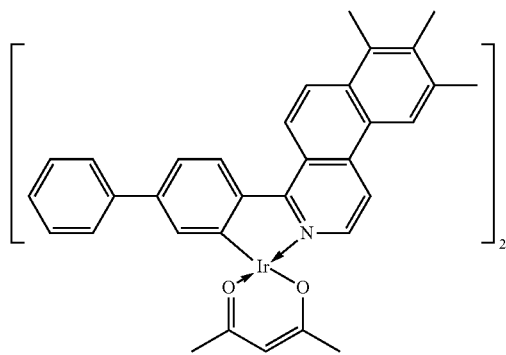
Ir-310
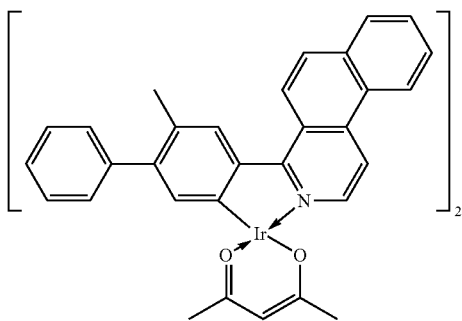
Ir-311
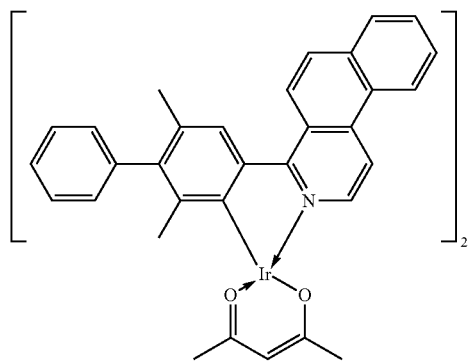
Ir-312
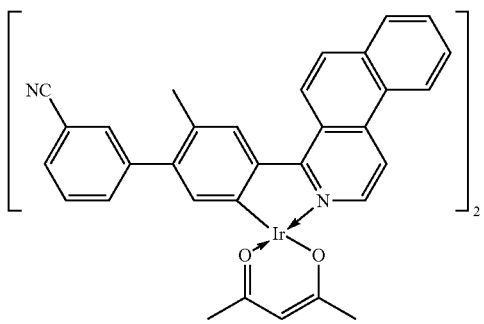

-continued
Ir-313
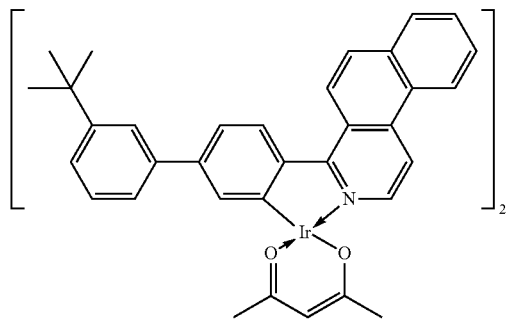
Ir-314
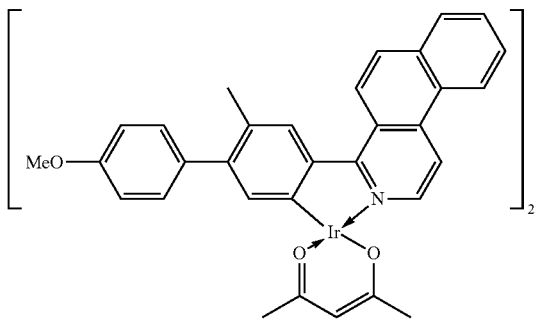
Ir-315
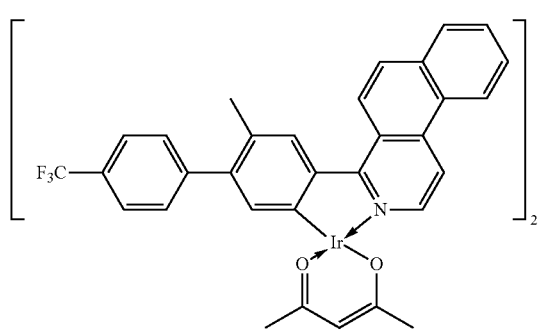
Ir-316
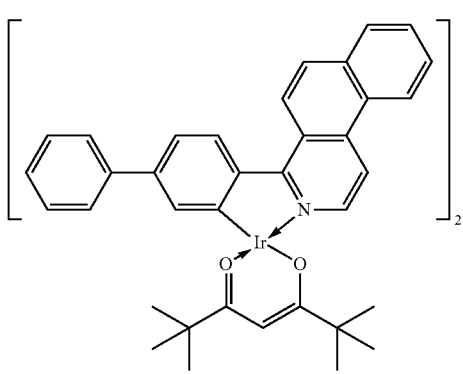
Ir-317
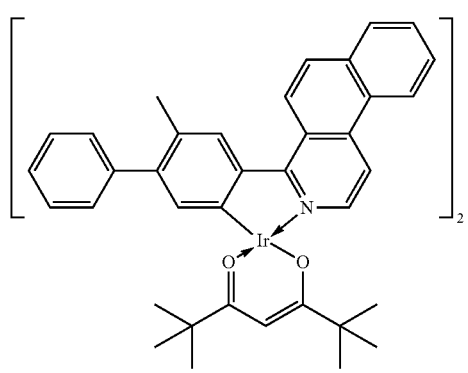
Ir-318
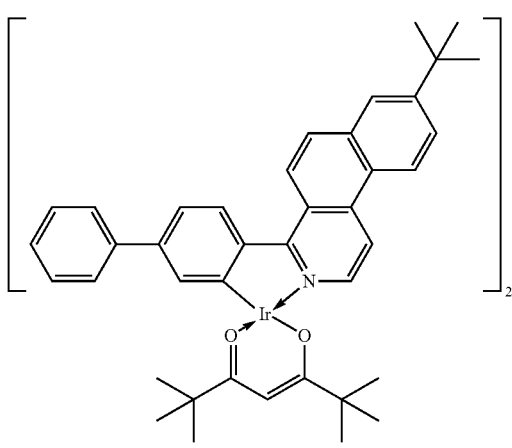
Ir-319
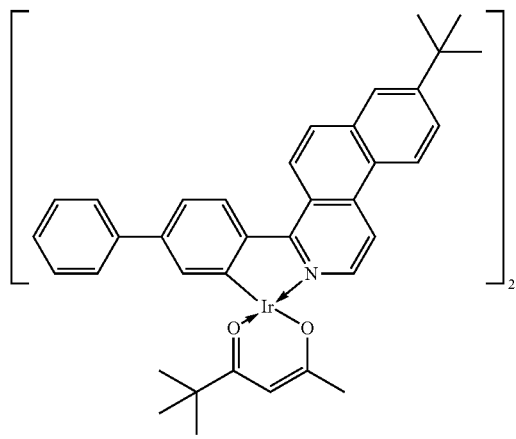
Ir-320

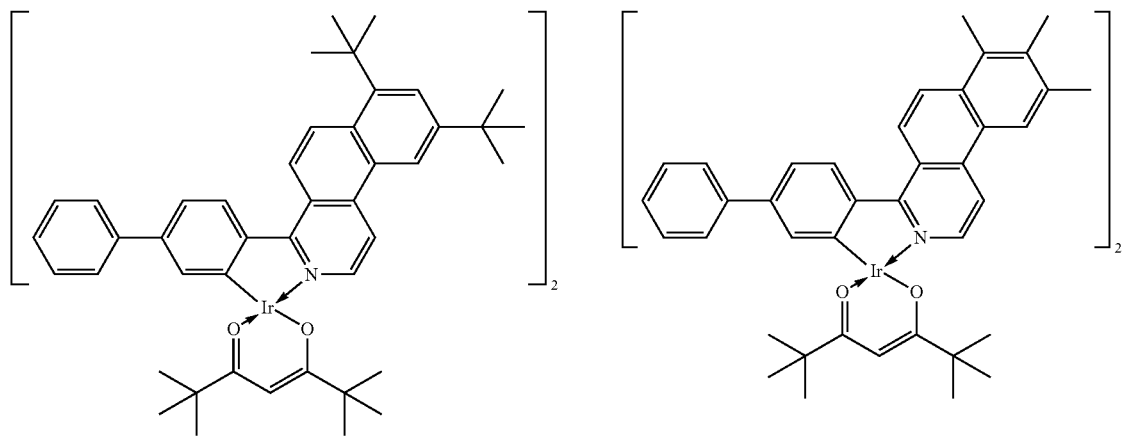
[Group 4 Iridium Complex]
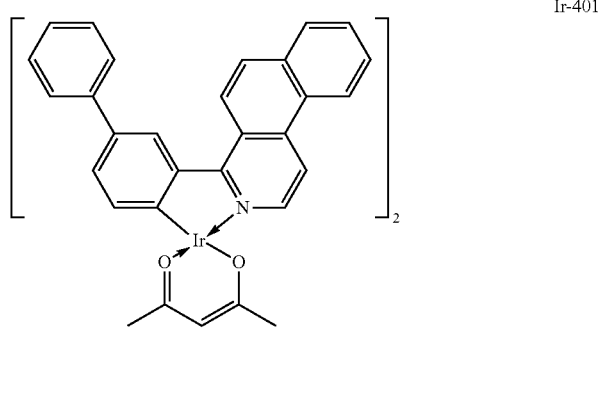
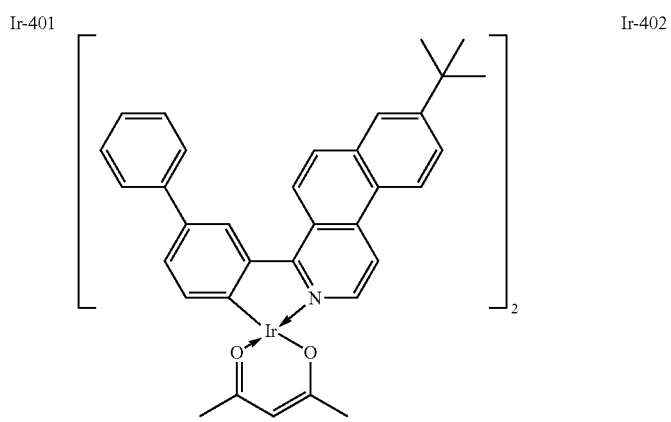
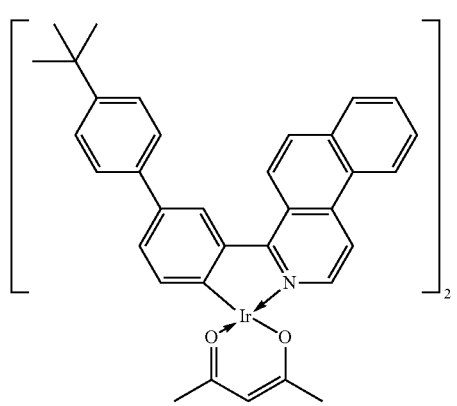
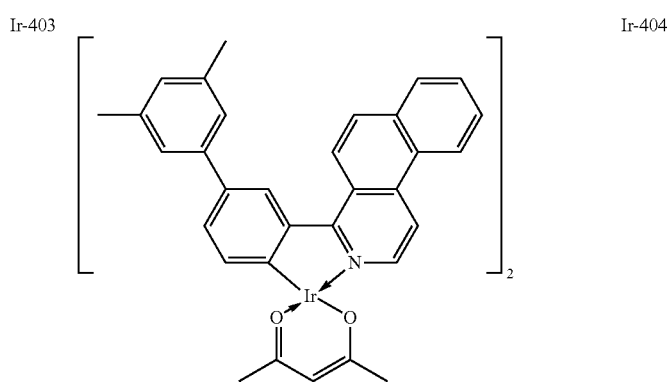

-continued
Ir-405
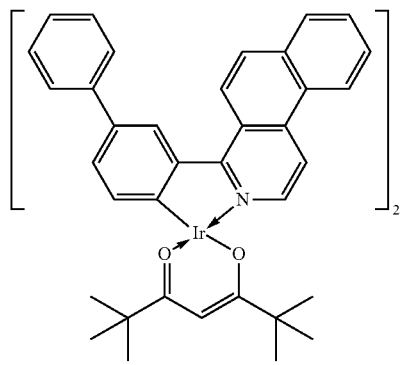
Ir-406
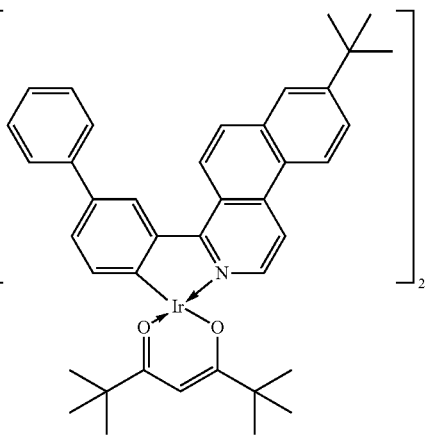
Ir-407
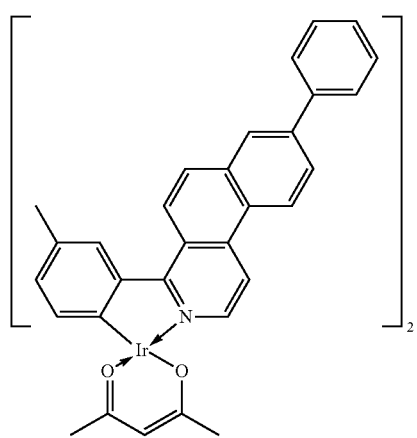
Ir-408
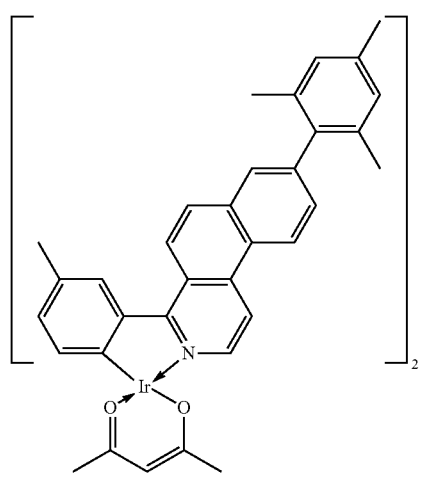
Ir-409
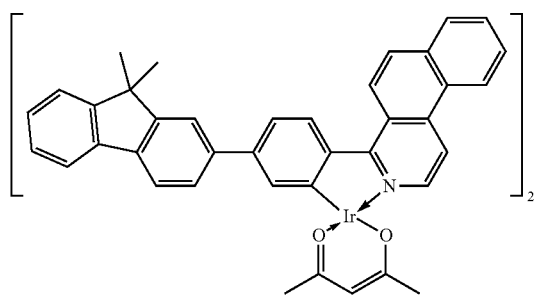
Ir-410
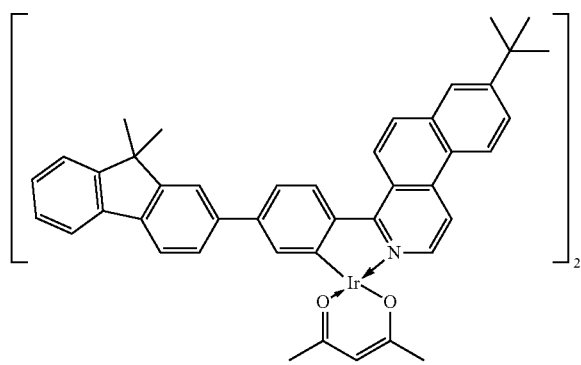
Ir-411
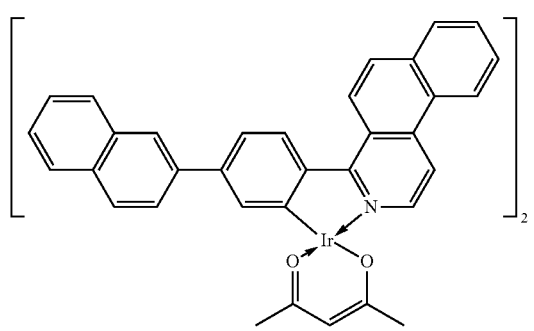
Ir-412
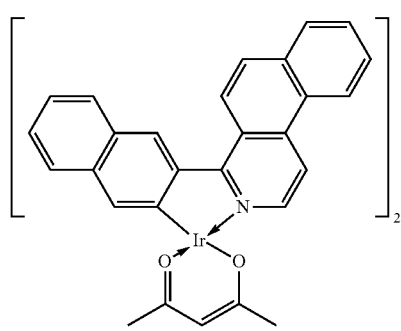

-continued
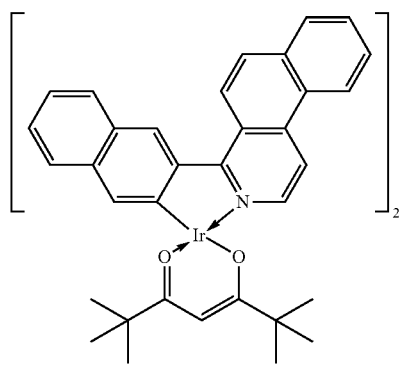
Ir-413
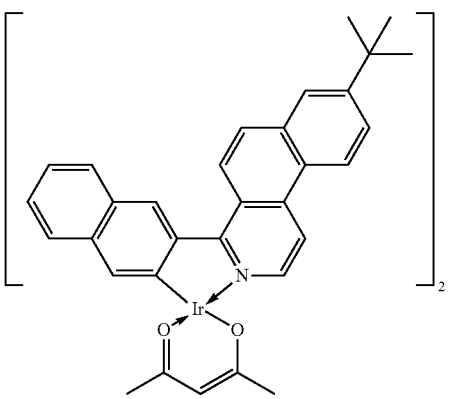
Ir-414
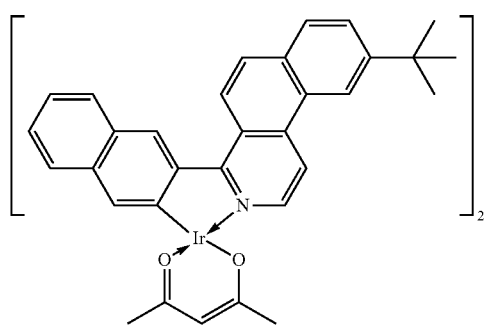
Ir-415
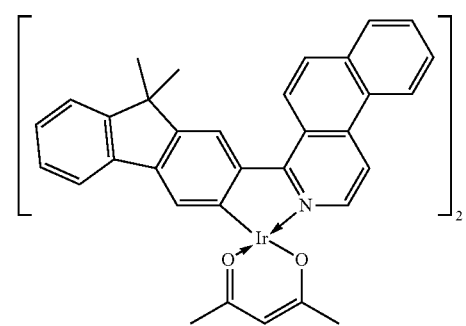
Ir-416
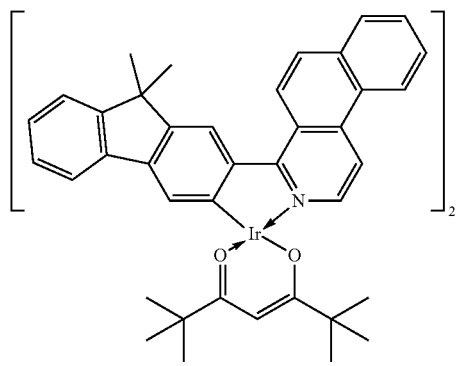
Ir-417
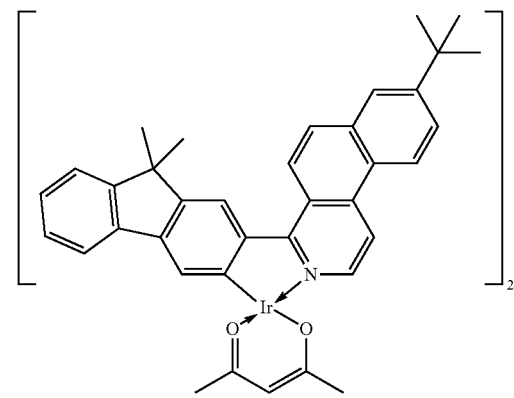
Ir-418
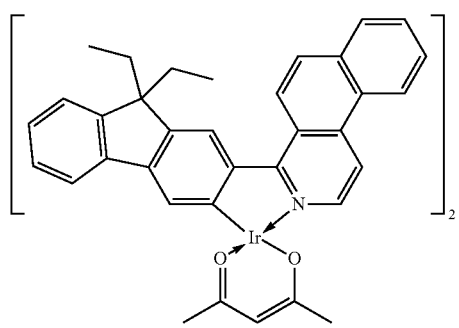
Ir-419
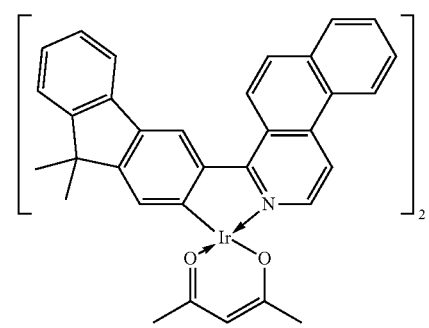
Ir-420

-continued
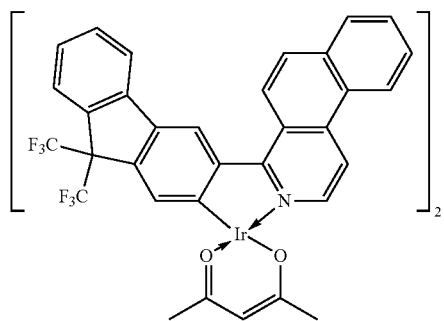
Ir-421
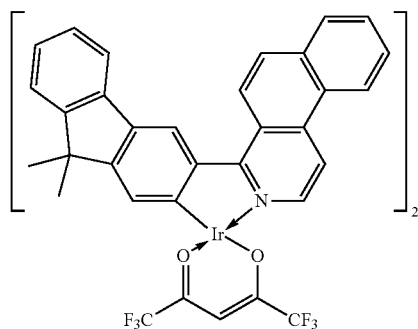
Ir-422
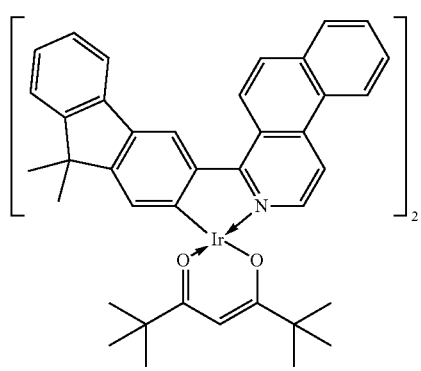
Ir-423
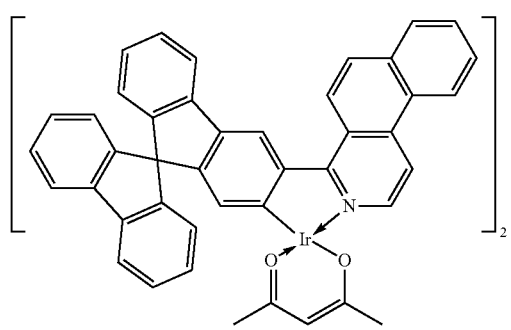
Ir-424
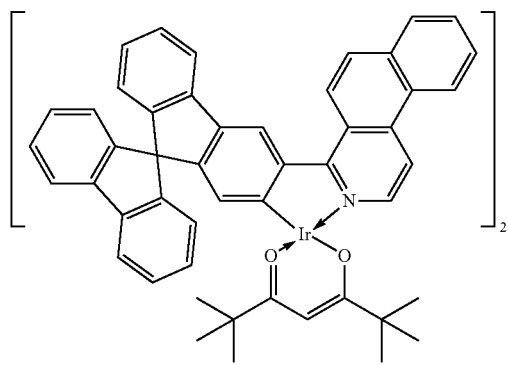
Ir-425
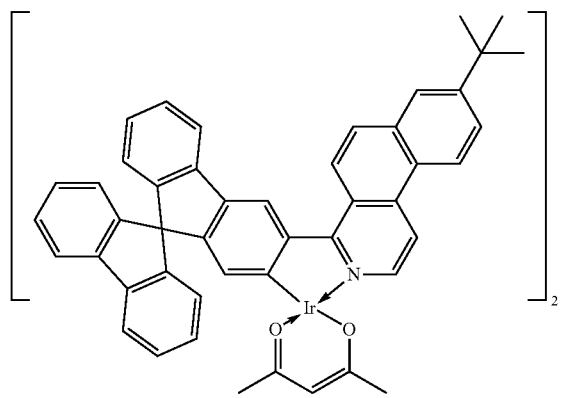
Ir-426
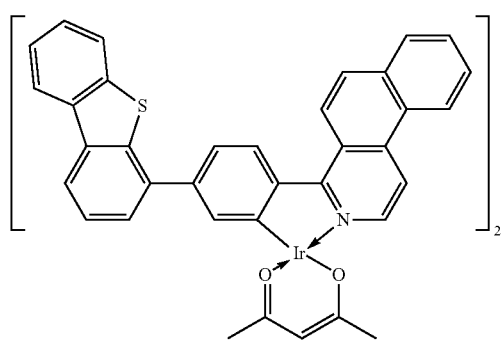
Ir-427
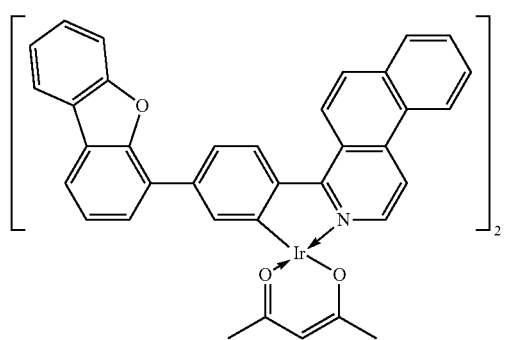
Ir-428

Ir-429
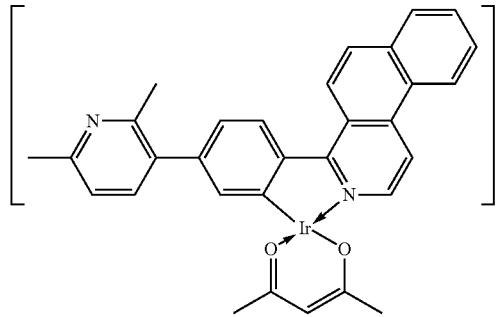
[Group 5a Iridium Complex]
Ir-501
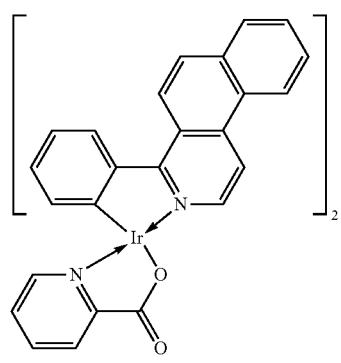
Ir-502
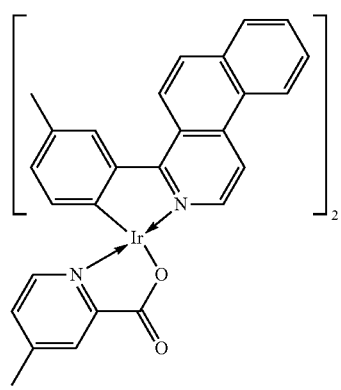
Ir-503
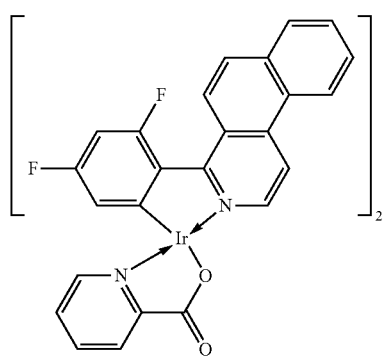
Ir-504
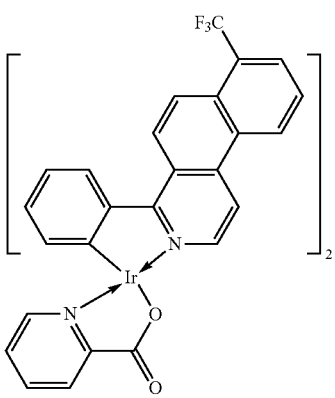
Ir-505
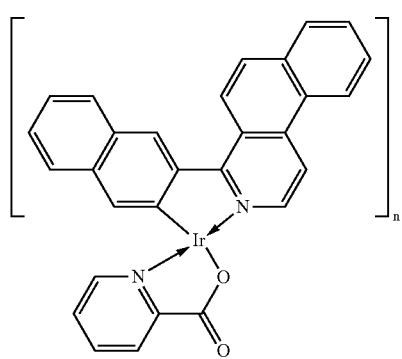
Ir-506
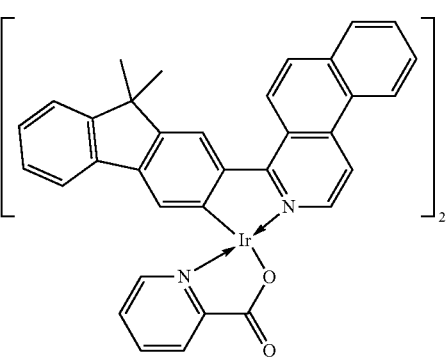

Ir-507 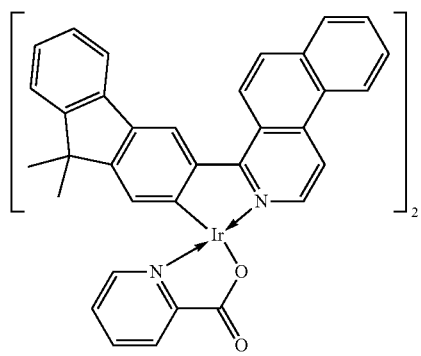 Ir-508 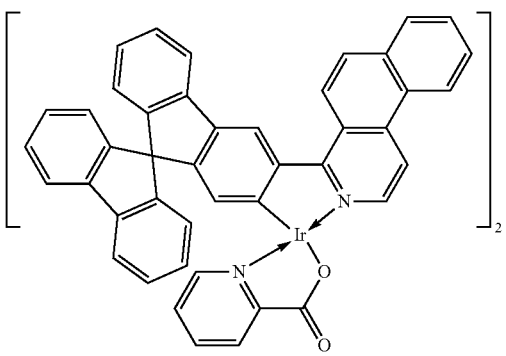
[Group 5b Iridium Complex]
Ir-509 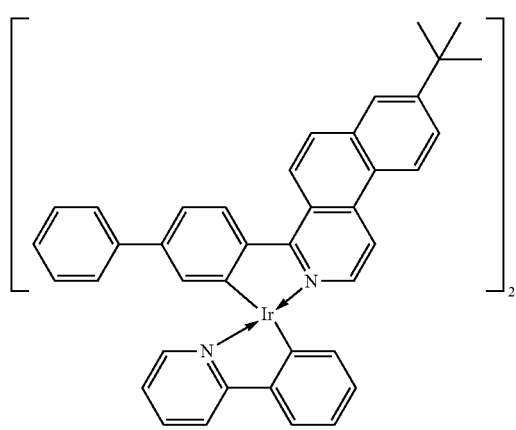 Ir-510 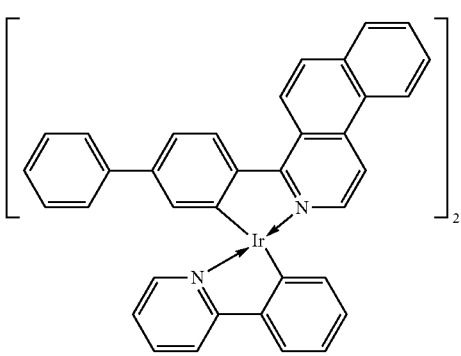
Ir-511 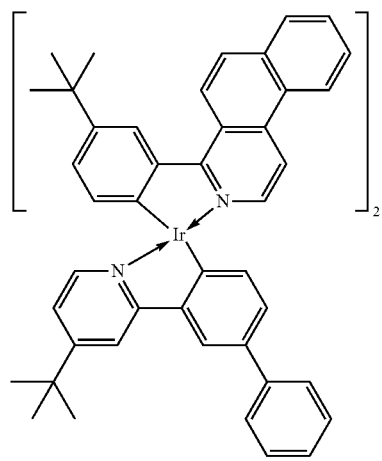 Ir-512 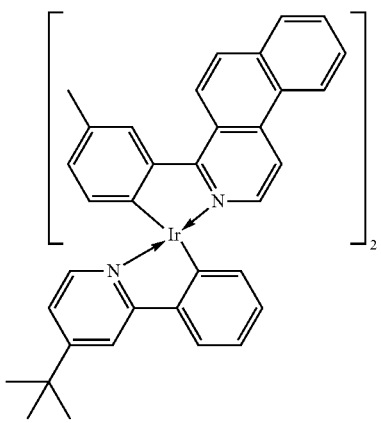
Ir-513 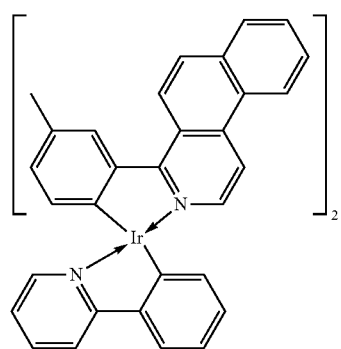 Ir-514 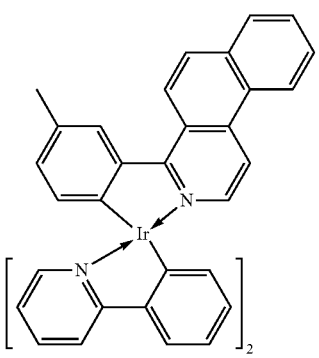

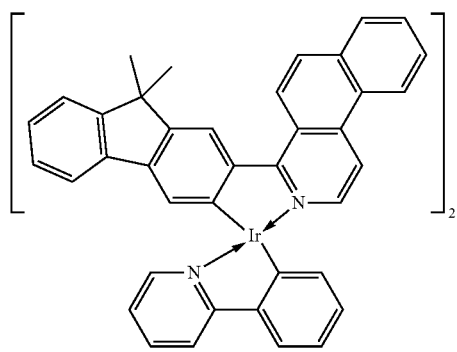

Ir-515

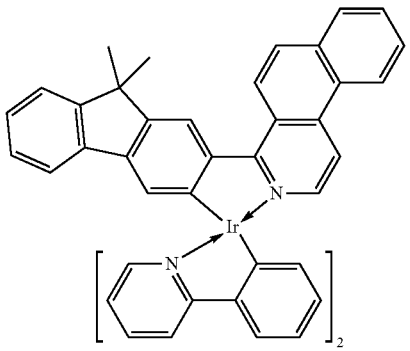

Ir-516

Of the exemplified compounds, the iridium complexes represented by Ir-101 to Ir-123 are each an iridium complex in which m represents 3 and n represents 0 out of the iridium complexes each represented by the general formula [1]. The stability of each of those iridium complexes in the group 1 itself is extremely high by virtue of the structure of the ligand (arylbenzo[f]isoquinoline ligand) of the complex. Therefore, the incorporation of any such complex as a guest into the light-emitting layer provides a long-lifetime organic light-emitting element because the incorporation improves its driving durability.

Of the exemplified compounds, the iridium complexes represented by Ir-201 to Ir-226 are each an iridium complex in which G does not represent a substituted or unsubstituted phenyl group out of the iridium complexes each represented by the general formula [20]. Those iridium complexes in the group 2 are each a complex having an extremely high emission quantum yield and hence the incorporation of any such complex as a guest into the light-emitting layer provides an organic light-emitting element having high luminous efficiency. Further, three ligands of each iridium complex in the group 2 include one acac-based ligand (diketone-based bidentate ligand) having a small molecular weight. Accordingly, the complex has the following advantage: the complex can be easily subjected to sublimation purification because the molecular weight of the complex itself is relatively small.

Of the exemplified compounds, the iridium complexes represented by Ir-301 to Ir-322 are each an iridium complex in which G represents a substituted or unsubstituted phenyl group out of the iridium complexes each represented by the general formula [20]. Those iridium complexes in the group 3 are each a complex having an extremely high emission quantum yield as in the iridium complexes in the group 2. Accordingly, the incorporation of any such complex as a guest into the light-emitting layer improves the luminous efficiency of the organic light-emitting element.

Of the exemplified compounds, the iridium complexes represented by Ir-401 to Ir-429 are each an iridium complex represented by the general formula [6] in which m represents 2 and n represents 1, but the iridium complex does not correspond to any iridium complex represented by the general formula [20]. Those iridium complexes in the group 4 are each also a complex having an extremely high emission quantum yield as in the iridium complexes in the groups 2 and 3. Accordingly, the incorporation of any such complex as a guest into the light-emitting layer improves the luminous efficiency of the organic light-emitting element.

Of the exemplified compounds, the iridium complexes represented by Ir-501 to Ir-508 are each an iridium complex represented by the general formula [1] in which the partial structure $IrX_n$ is represented by the formula [3]. Those iridium complexes in the group 5a each contain, in a molecule thereof, one picolinic acid derivative as a ligand. In this case, when the picolinic acid derivative is introduced as a ligand, the emission peak wavelength of the complex itself shifts to shorter wavelengths as compared to that in the case where the acac-based ligand is introduced.

Of the exemplified compounds, the iridium complexes represented by Ir-509 to Ir-516 are each an iridium complex represented by the general formula [1] in which the partial structure $IrX_n$ is represented by the formula [2]. Those iridium complexes in the group 5b each contain one or two phenylpyridine (ppy) derivative ligands in three ligands of each iridium complex. Each iridium complex in the group 5b provides red light emission derived from the arylbenzo[f]isoquinoline ligand because the ppy derivative ligand in this case is a non-light-emitting ligand. In addition, the ligand ppy has a smaller molecular weight than that of the arylbenzo[f]isoquinoline ligand. Accordingly, the complex has a smaller molecular weight than that of any iridium complex in the group 1 and hence can be easily subjected to sublimation purification. Therefore, the incorporation of any iridium complex in the group 5b as a guest into the light-emitting layer as in any iridium complex in the group 1 can provide a long-lifetime organic light-emitting element.

By the way, the following structural isomers sterically exist for the iridium complex represented by the general formula [1]: an facial (fac) form and an meridional (mer) form. Although the steric structure of the iridium complex represented by the general formula [1] is not particularly limited in the present invention, the fac form generally credited with having a high quantum yield is preferred. However, in the case of an iridium complex in which two kinds of ligands having different structures coordinate to an iridium atom, the mer form such as $Ir(ppy)_2acac$ may also have a high quantum yield. Accordingly, the fac form is not necessarily preferred. In addition, it is difficult to synthesize one of the structural isomers selectively at the time of the synthesis of the complex, and both isomers may be used as a mixture in terms of a cost.

(6) Specific Examples of Heterocycle-Containing Compound

Specific structural formulae of the heterocycle-containing compound defined by the general formula [5] are exemplified below.

[Group 1 compound]
H-101
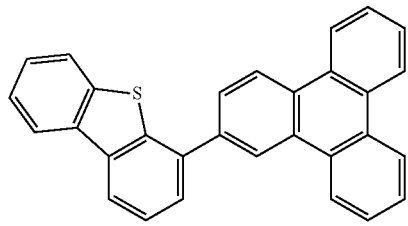
H-102
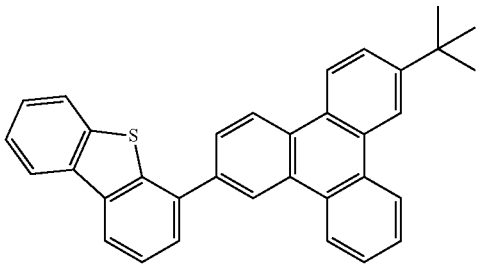
H-103
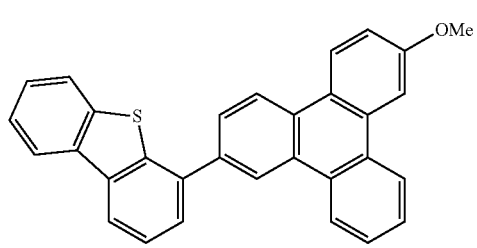
H-104
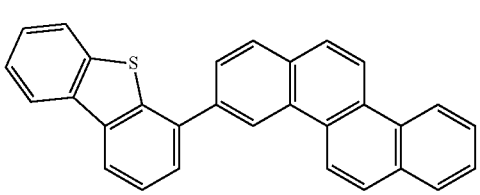
H-105
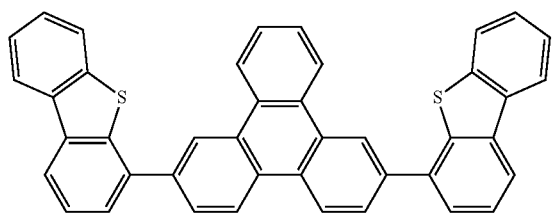
H-106
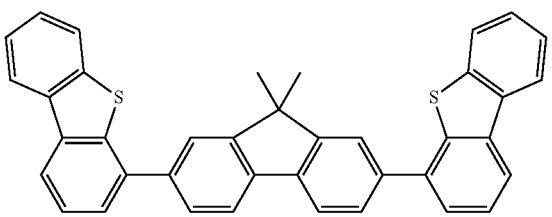
H-107
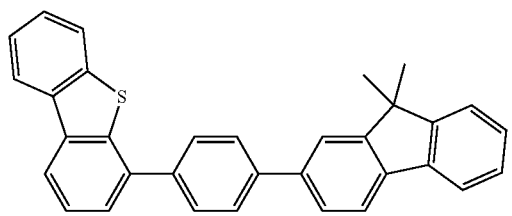
H-108
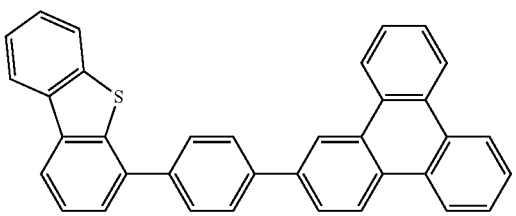
H-109
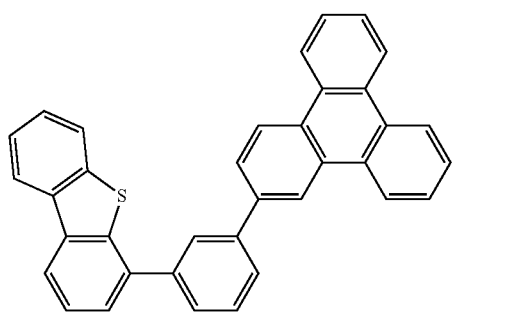
H-110
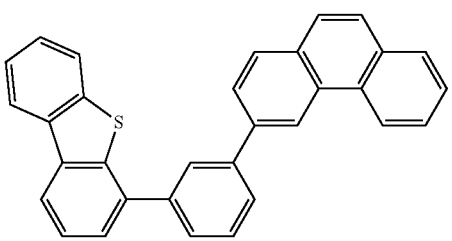
H-111
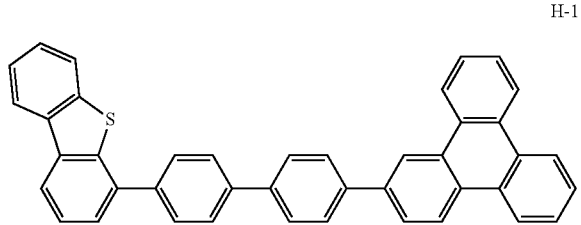
H-112
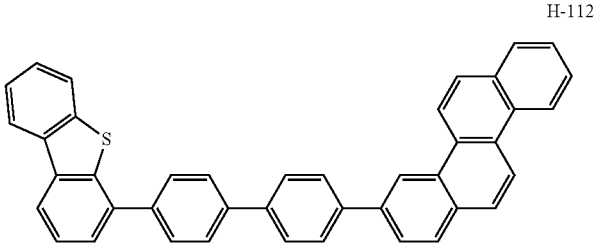

-continued
H-113
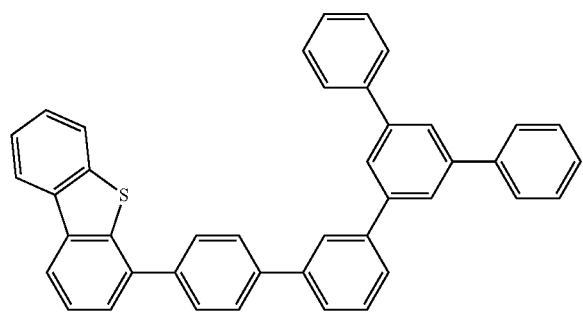
H-114
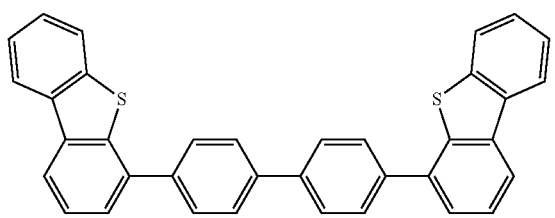
H-115
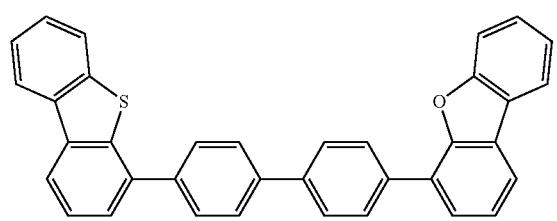
H-116
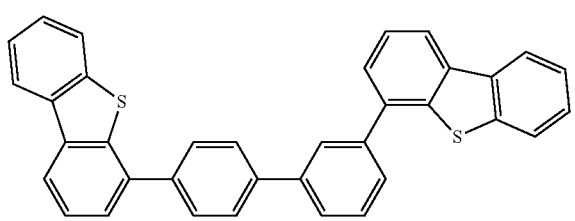
H-117
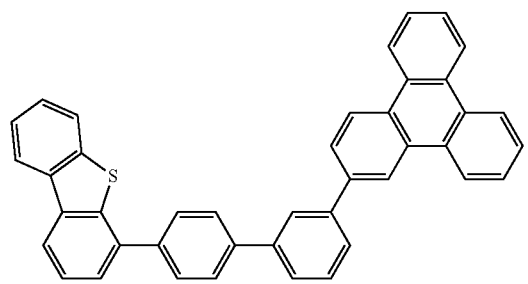
H-118
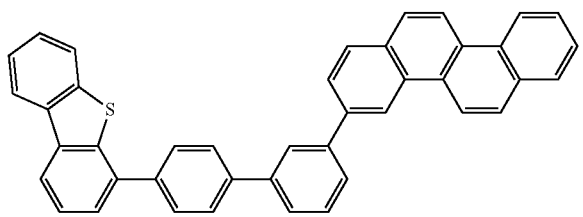
H-119
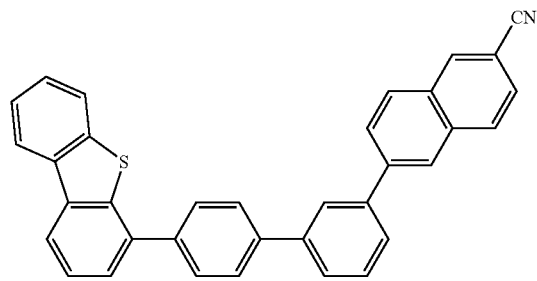
H-120
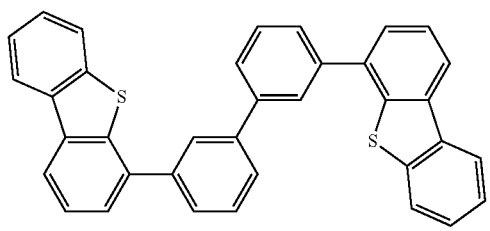
H-121
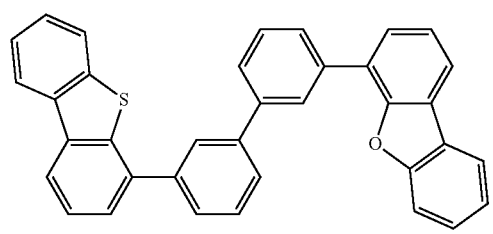
H-122
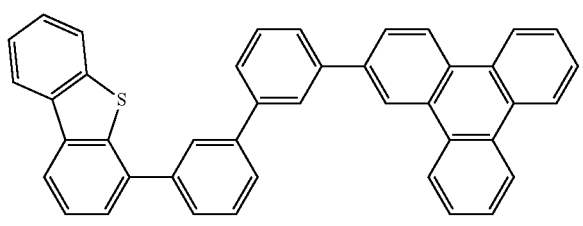

-continued
H-123
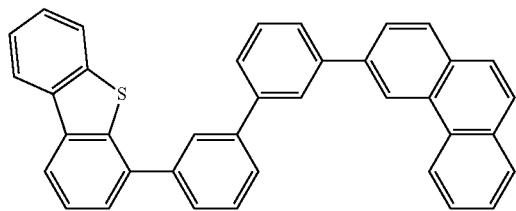
H-124
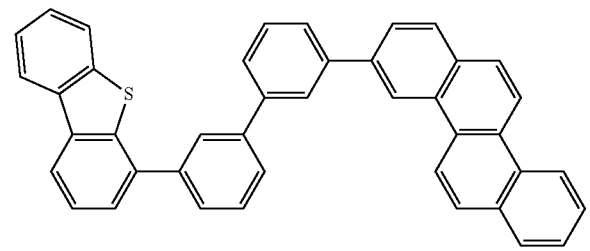
H-125
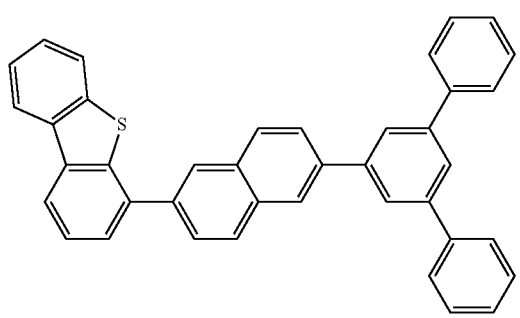
H-126
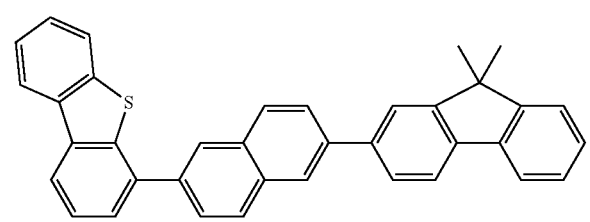
H-127
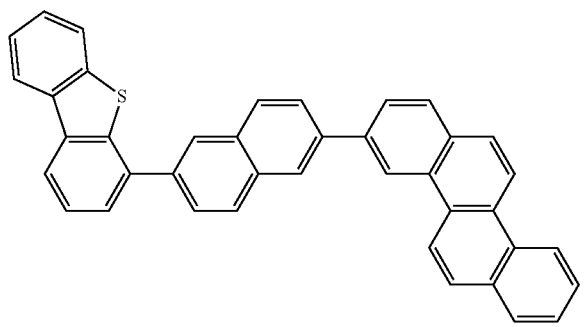
H-128
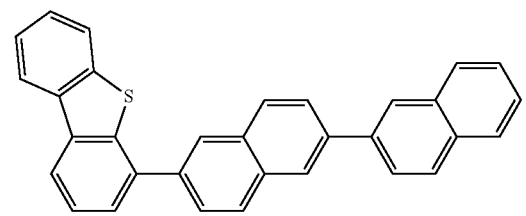
H-129
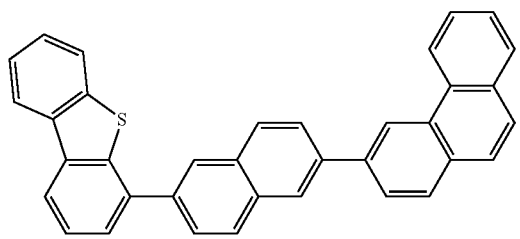
H-130
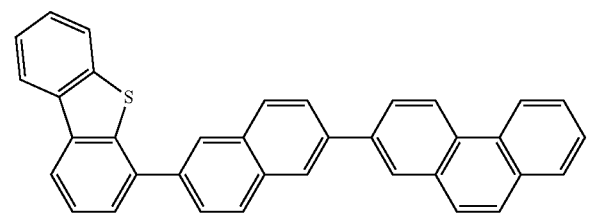
H-131
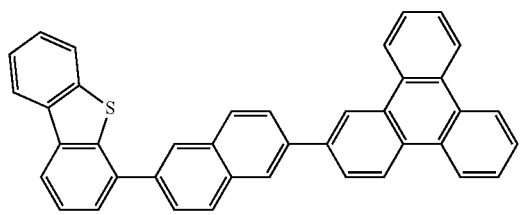
H-132
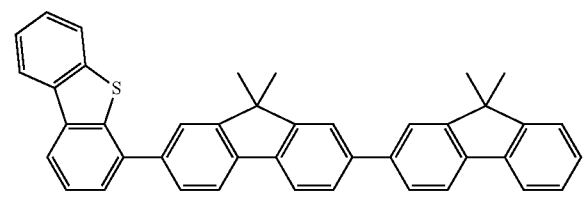

-continued
H-133
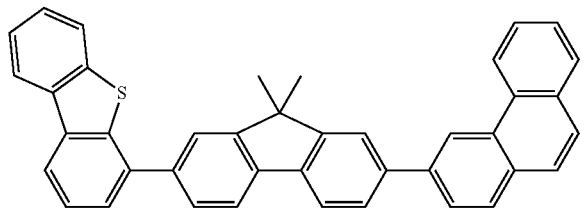
H-134
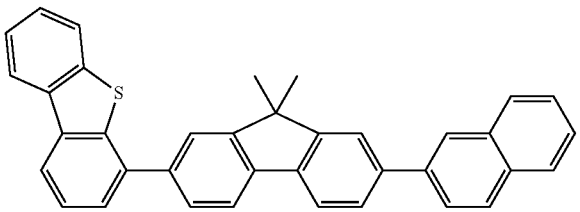
H-135
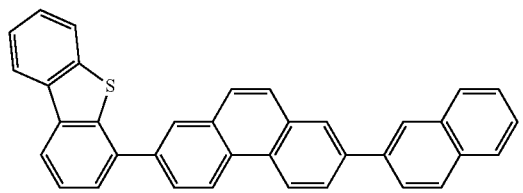
H-136
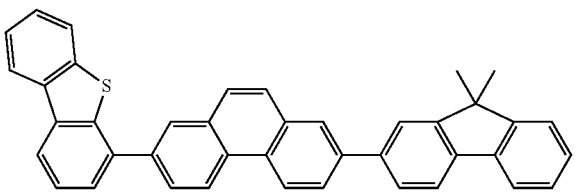
H-137
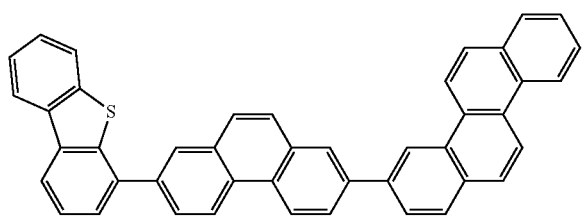
H-138
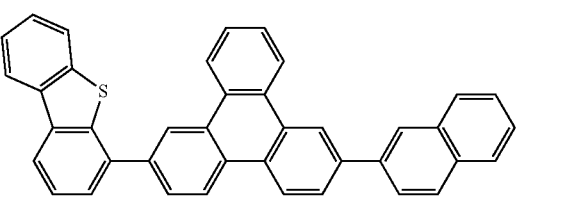
H-139
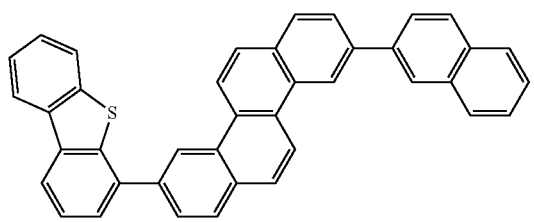
H-140
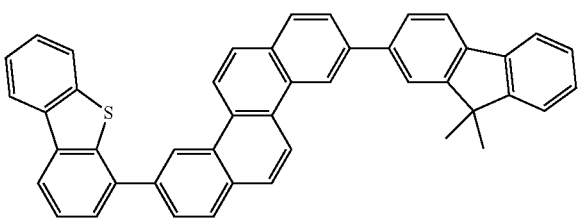
H-141
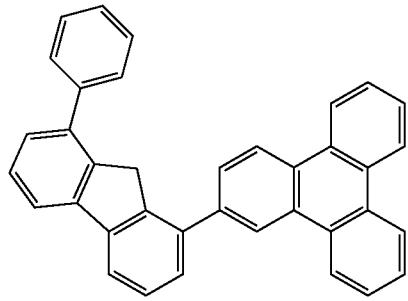
H-142
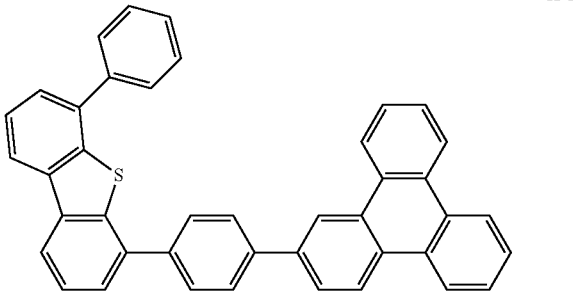
H-143
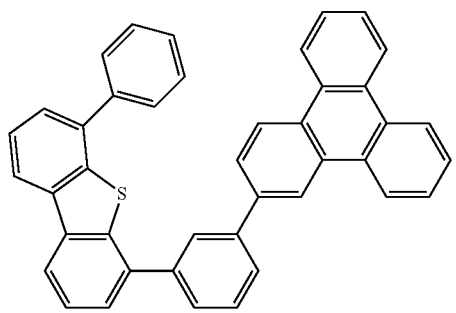
H-144
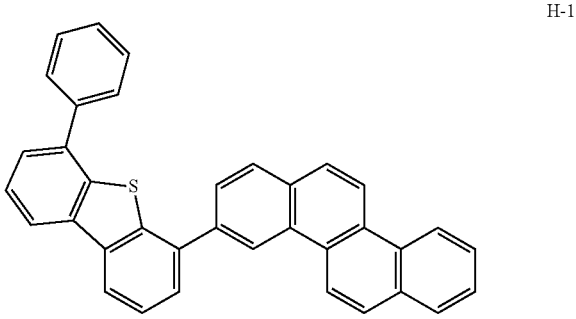

-continued
H-145
H-146
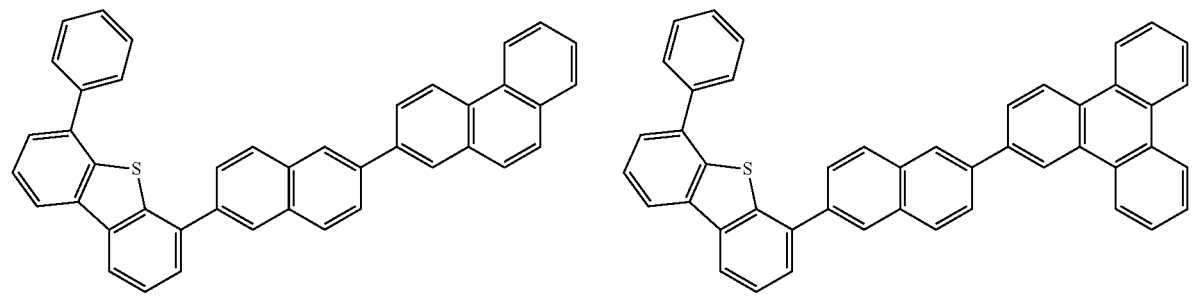
H-147
H-148
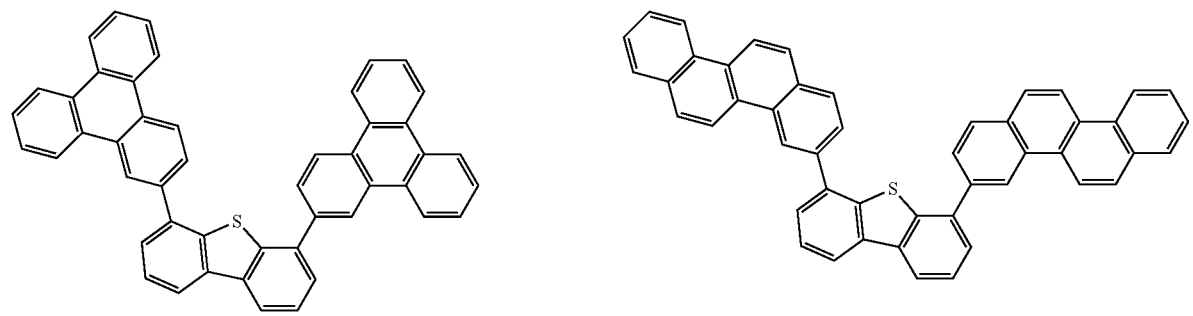
H-149
H-150
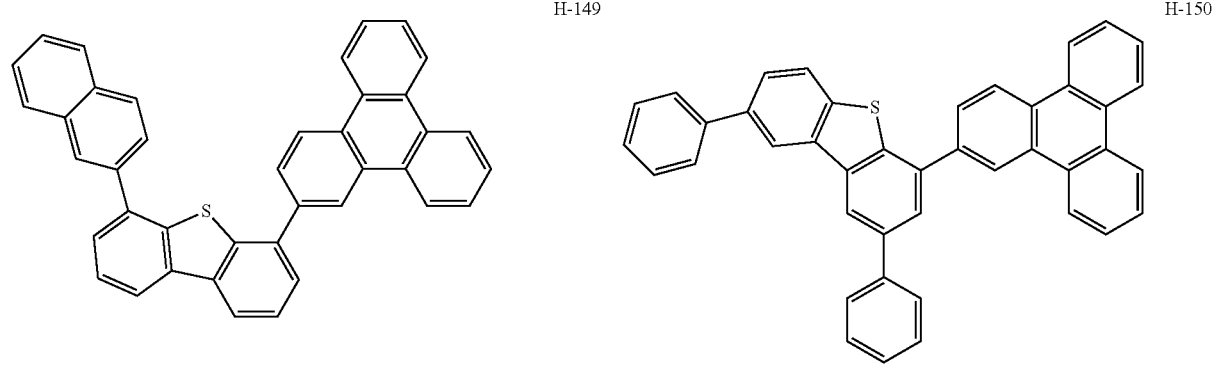
H-151
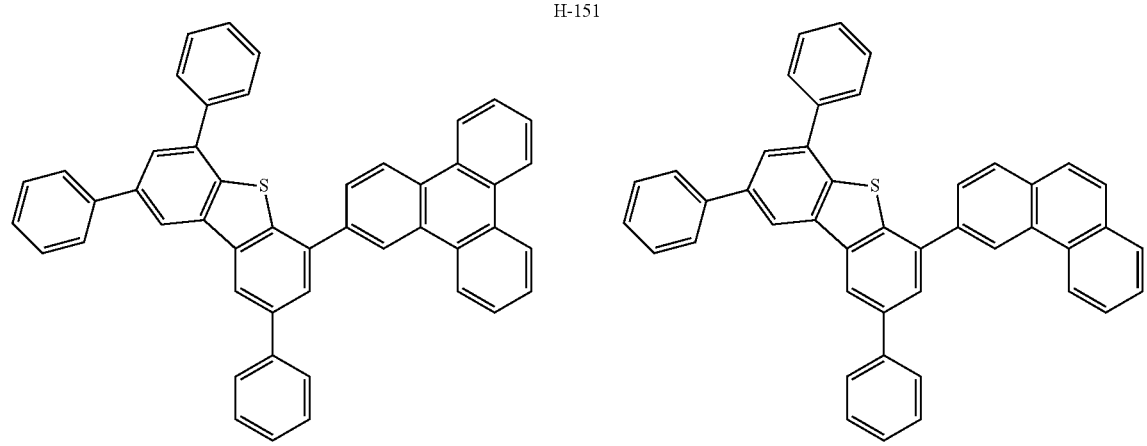

-continued
H-153
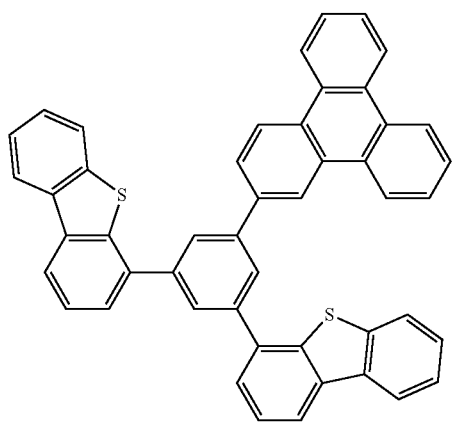
H-154
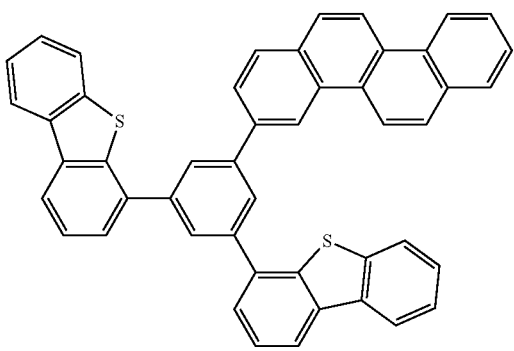
H-155
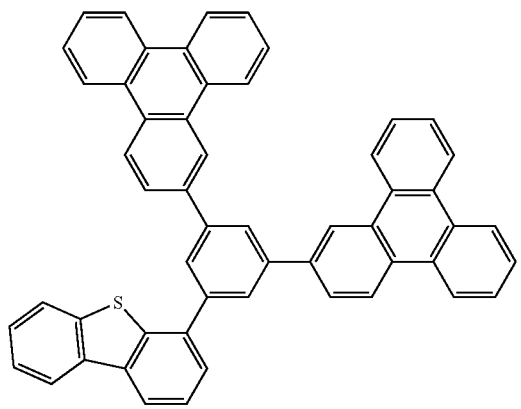
H-156
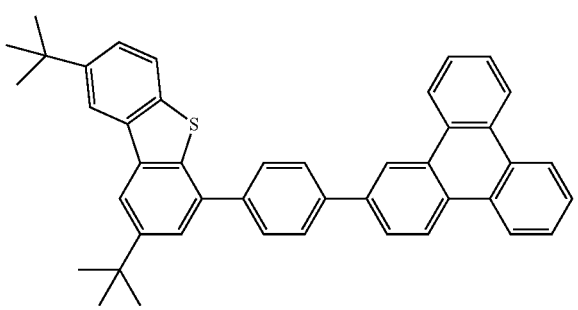
H-157
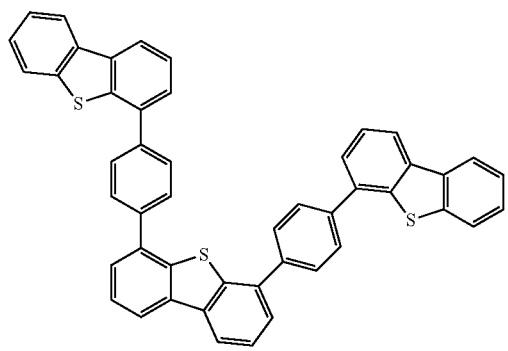
H-158
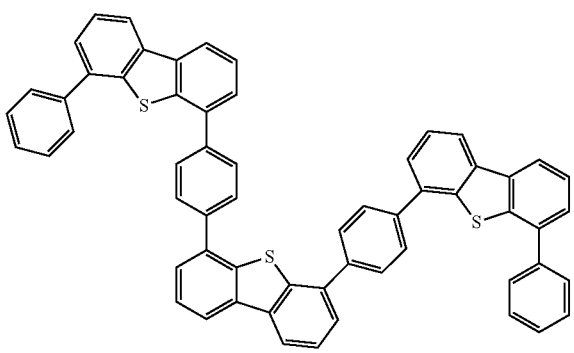
[Group 2 compound]
H-201
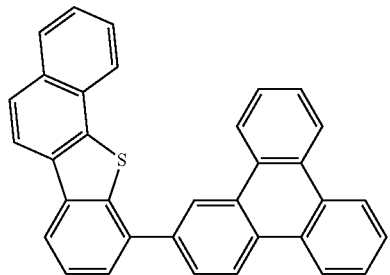
H-202
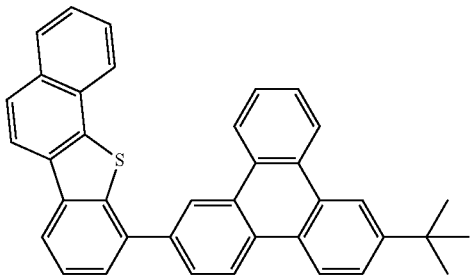

H-203
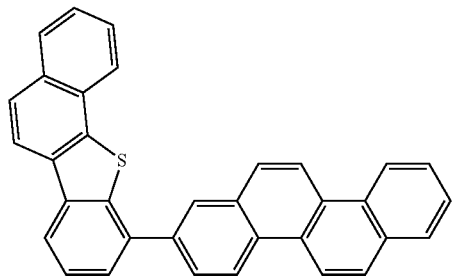
H-204
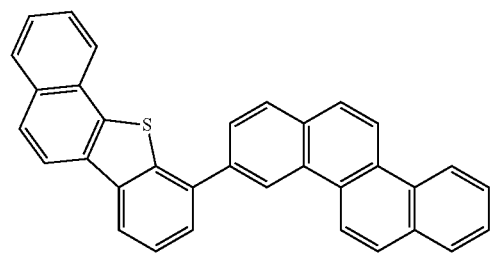
H-205
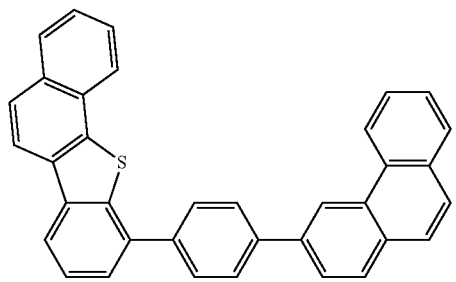
H-206
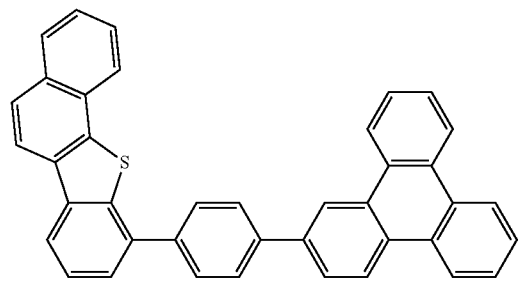
H-207
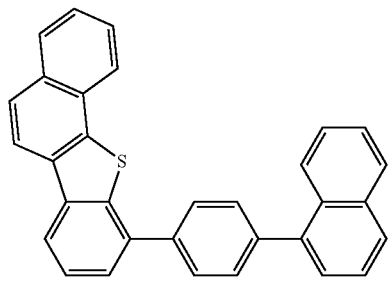
H-208
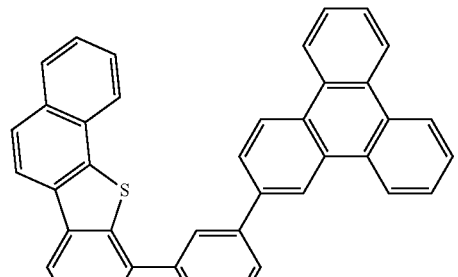
H-209
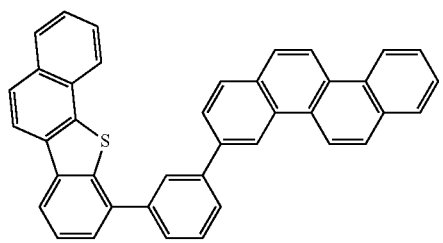
H-210
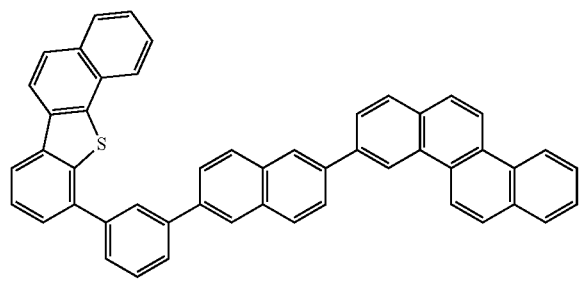
H-211
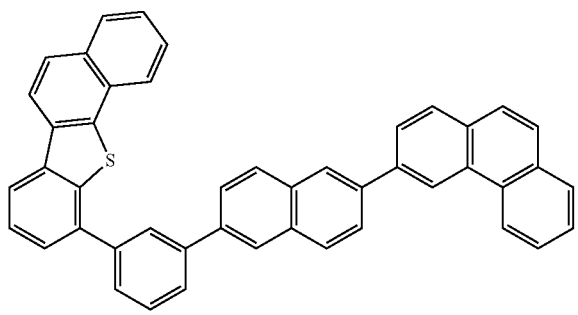
H-212
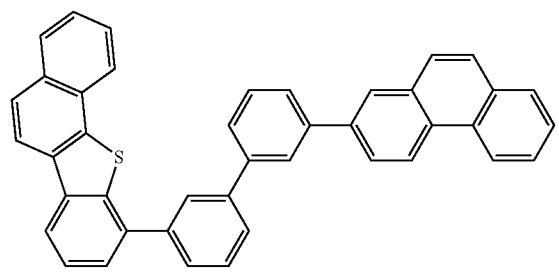

-continued
H-213
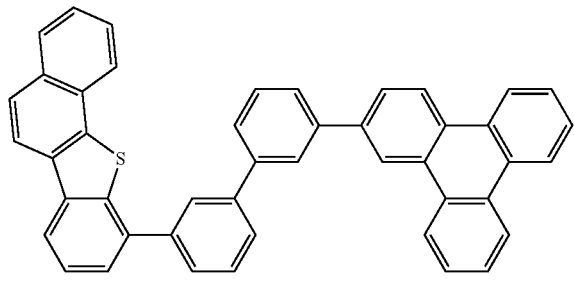
H-214
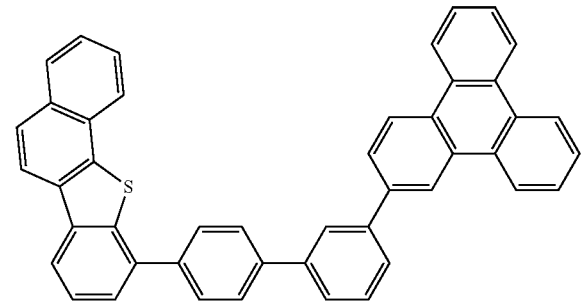
H-215
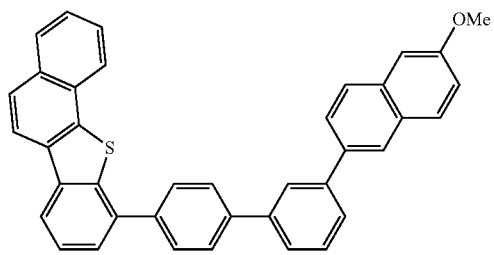
H-216
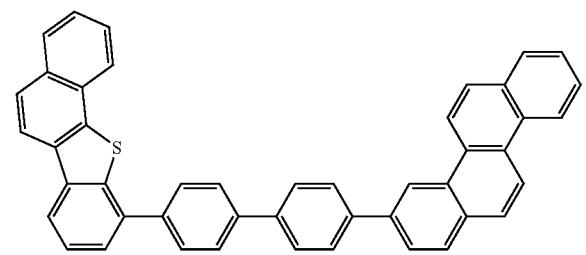
H-217
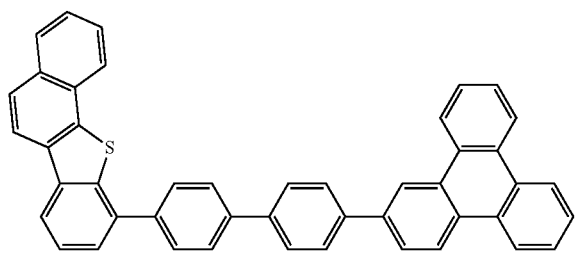
H-218
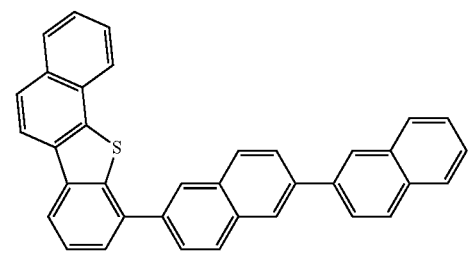
H-219
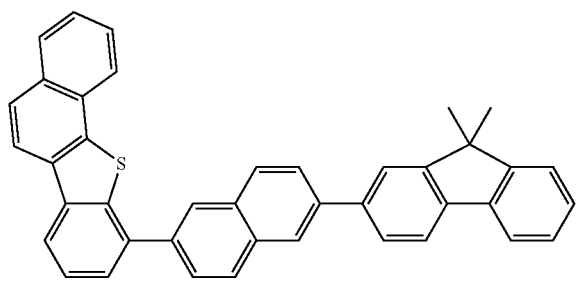
H-220
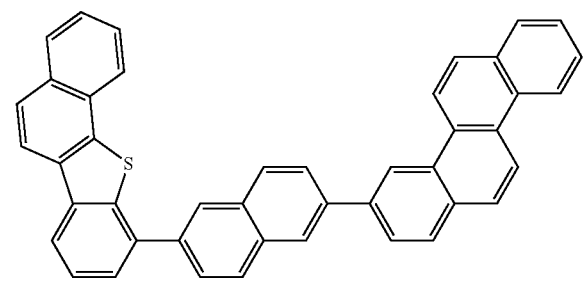
H-221
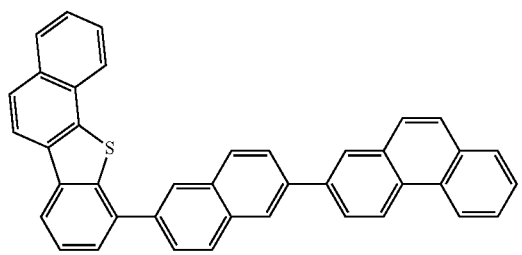
H-222
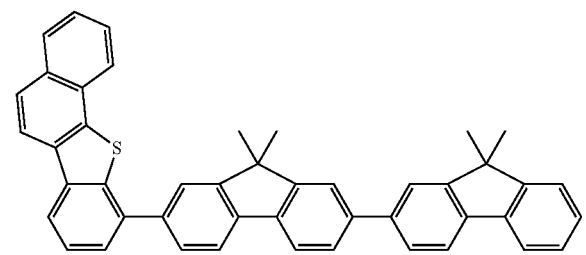

-continued
H-223
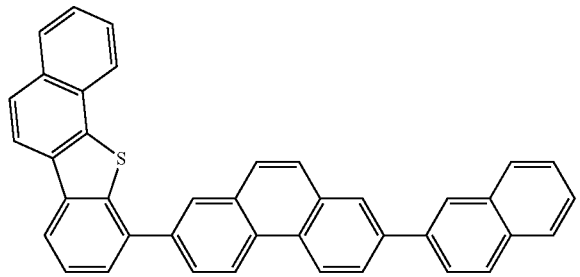
H-224
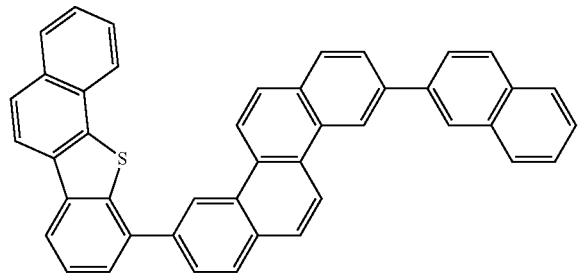
H-225
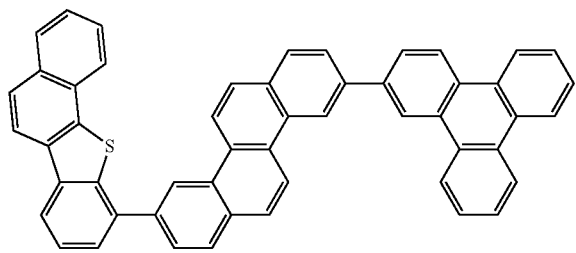
H-226
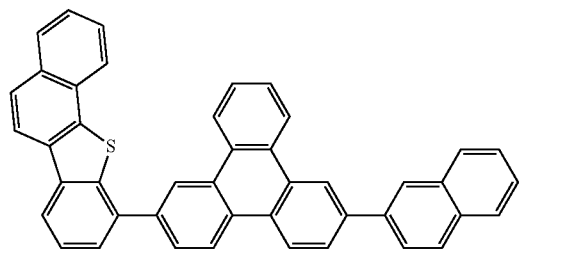
H-227
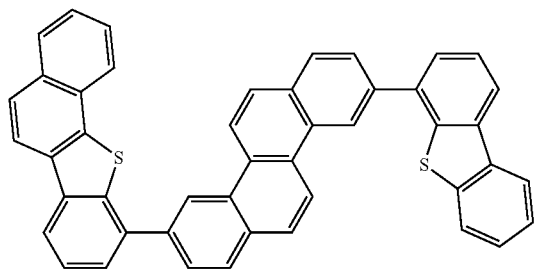
H-228
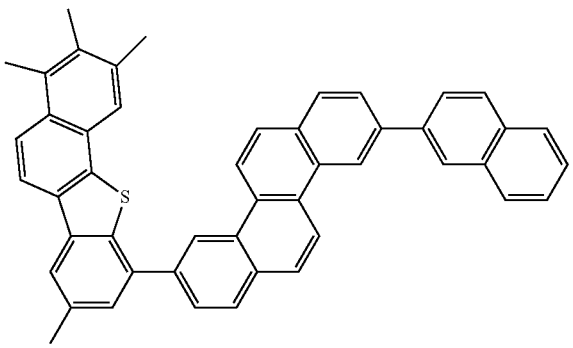
H-229
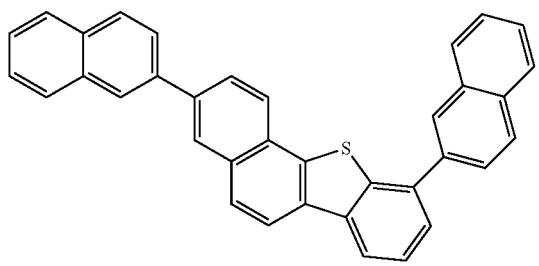
[Group 3 compound]
H-301
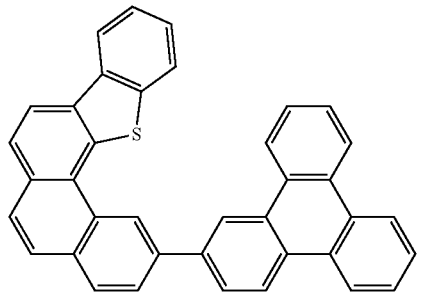
H-302
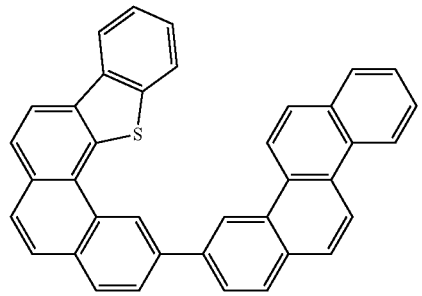

-continued
H-303
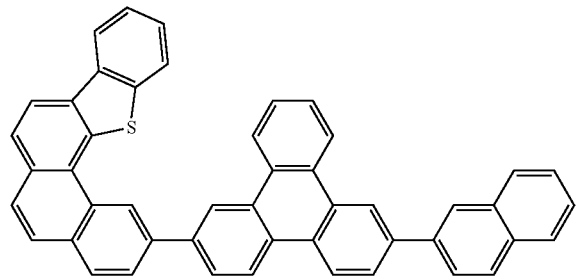
H-304
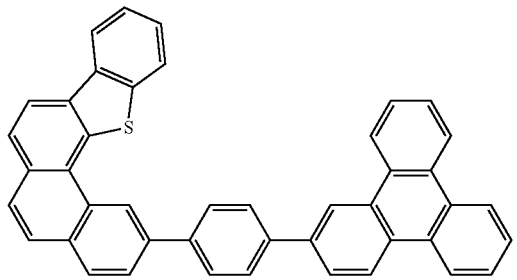
H-305
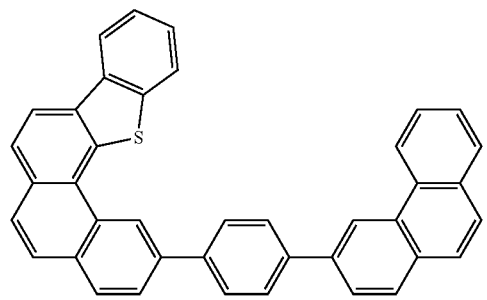
H-306
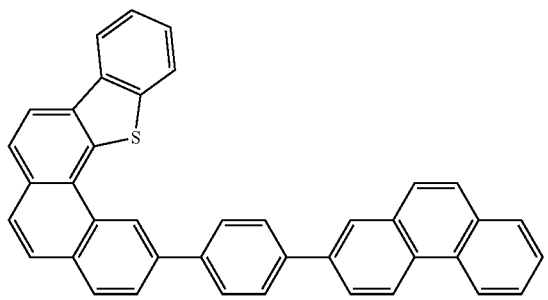
H-307
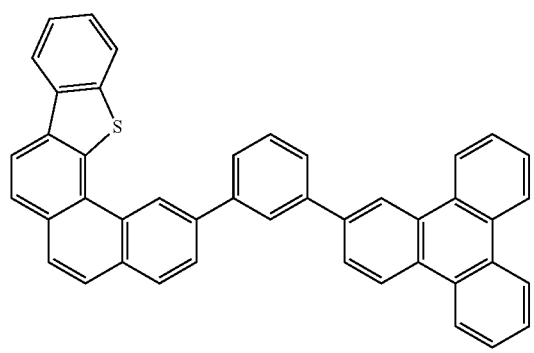
H-308
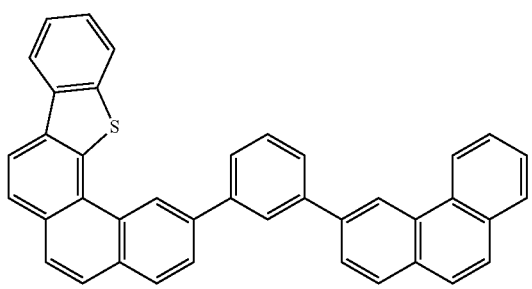
H-309
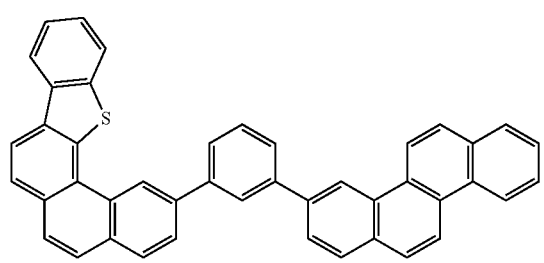
H-310
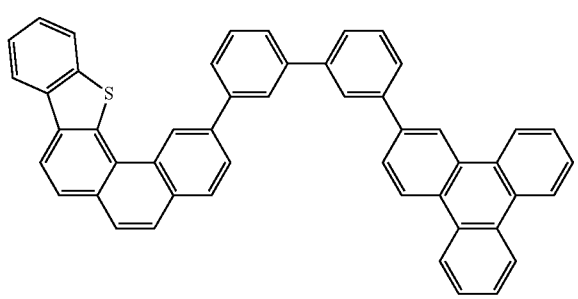
H-311
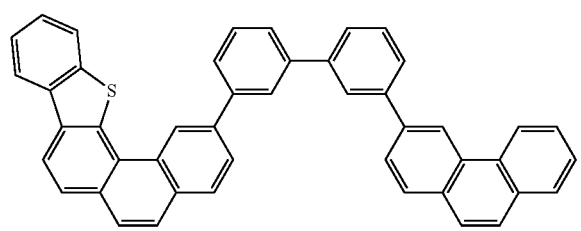
H-312
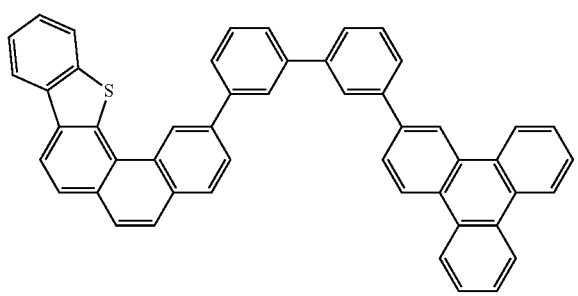

H-313
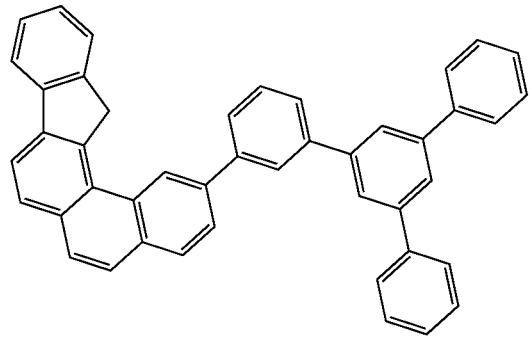
H-314
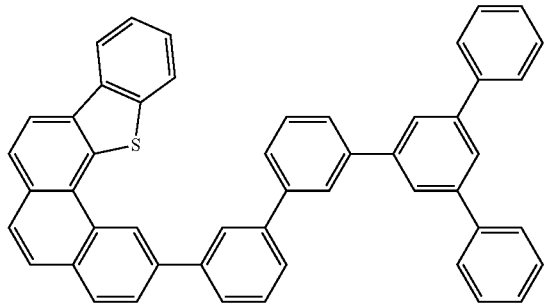
H-315
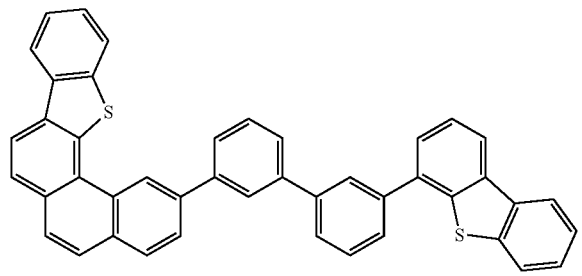
H-316
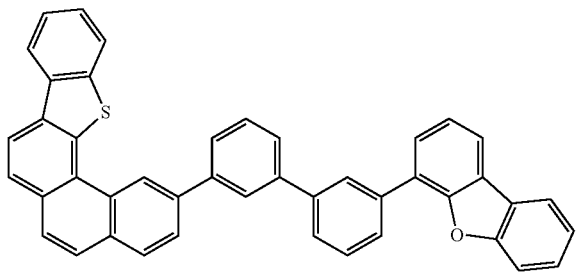
H-317
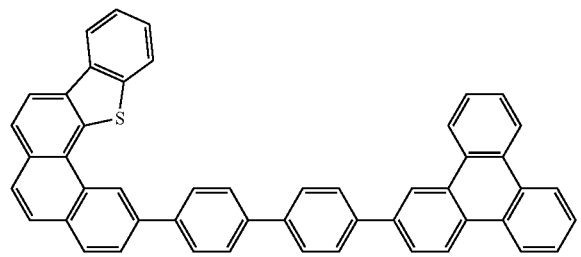
H-318
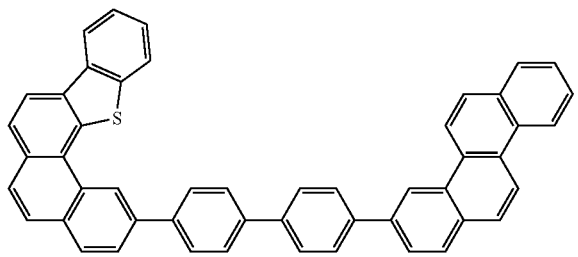
H-319
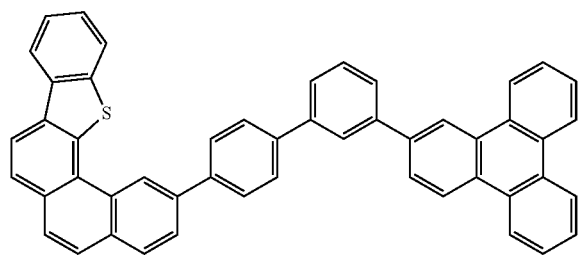
H-320
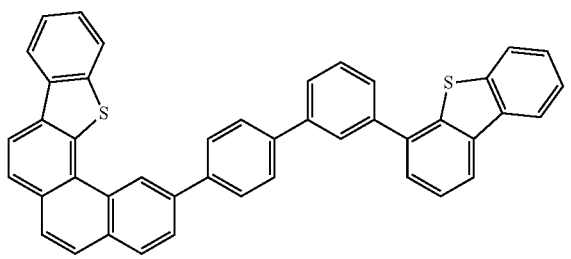
H-321
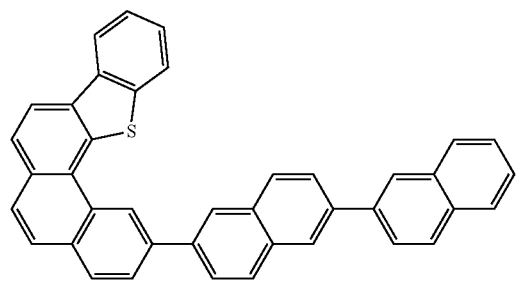
H-322
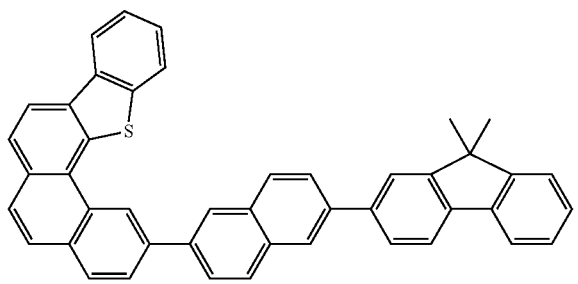

-continued
H-323
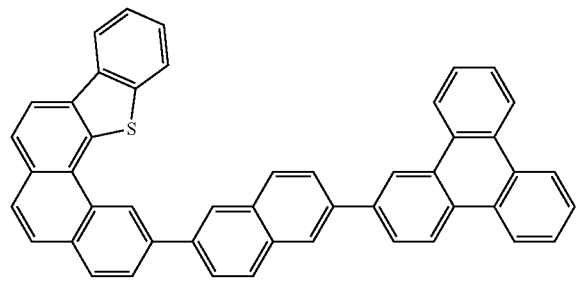
H-324
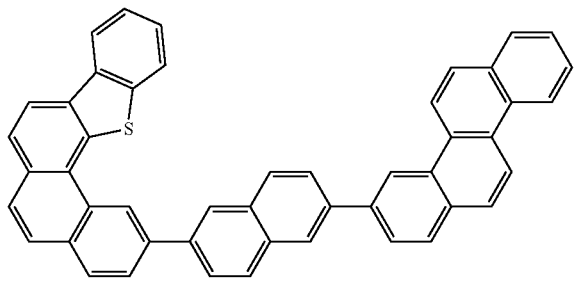
H-325
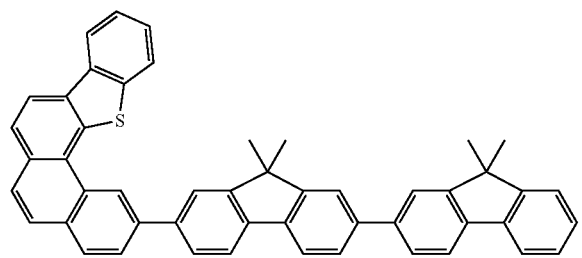
H-326
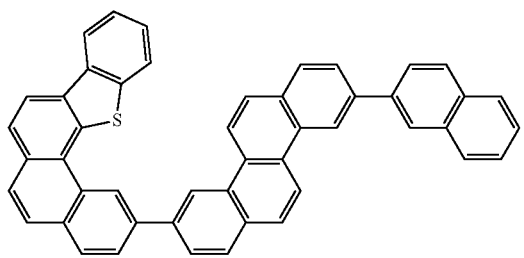
H-327
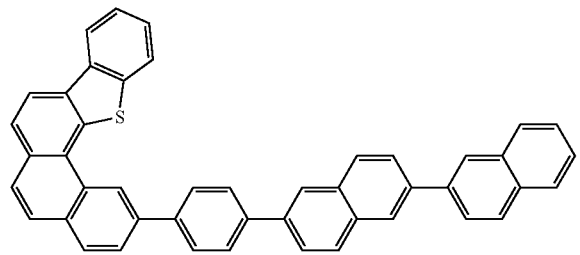
H-328
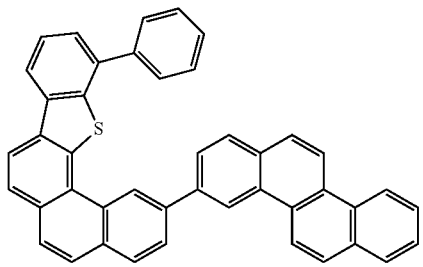
H-329
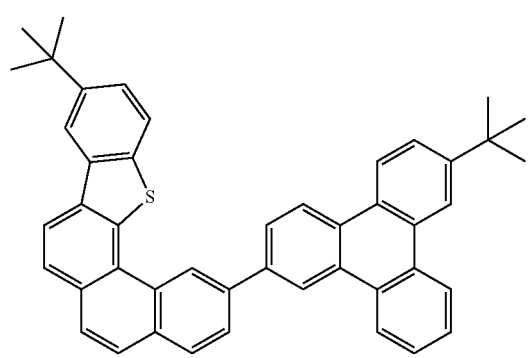
[Group 4 compound]
H-401
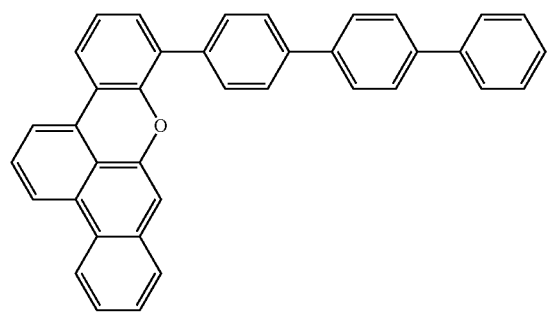
H-402
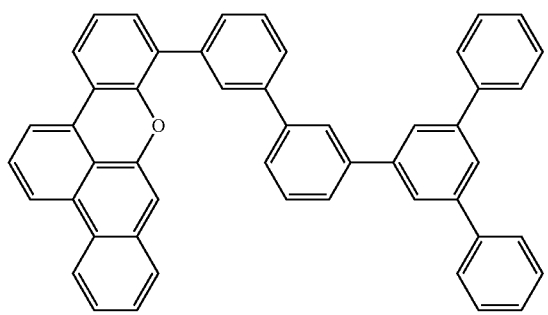

-continued
H-403
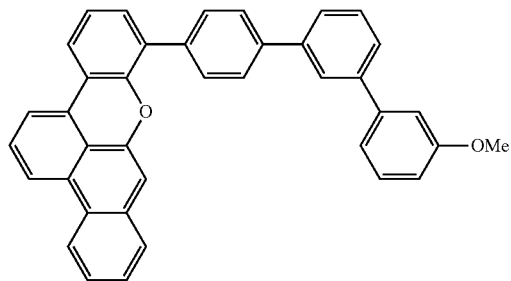
H-404
H-405
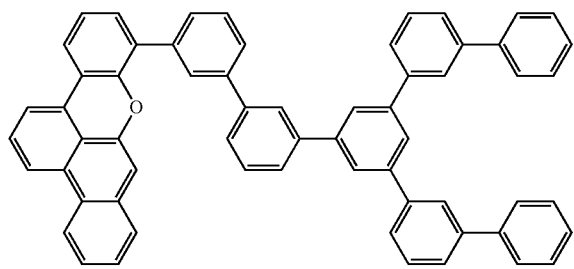
H-406
H-407
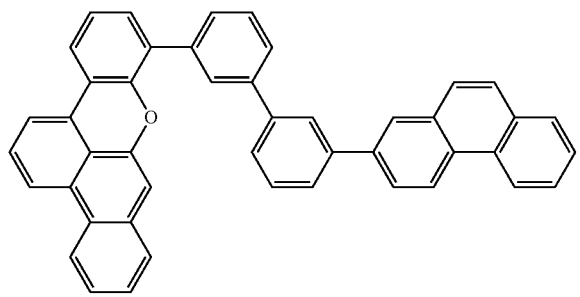
H-408
H-409
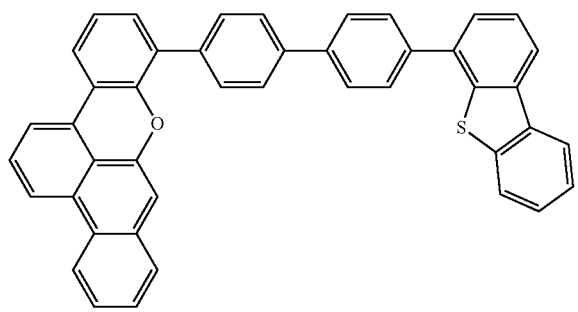
H-410
H-411
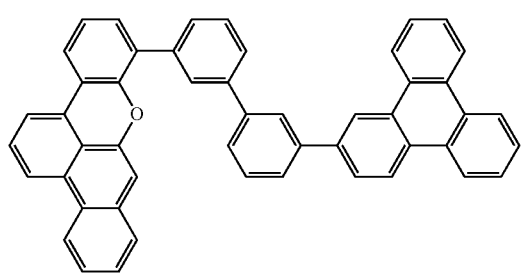
H-412
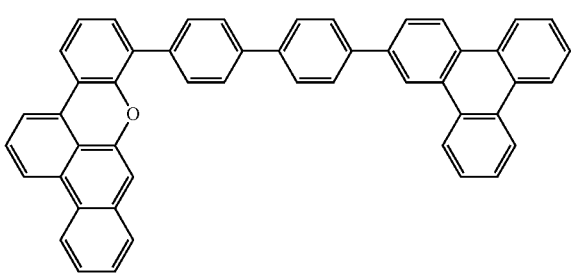

-continued

H-413

H-414

H-415

H-416

H-417

H-418

H-419

H-420

-continued
H-421
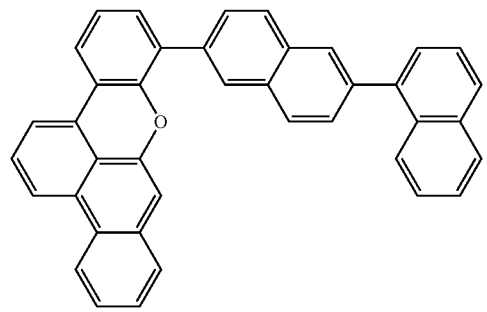
H-422
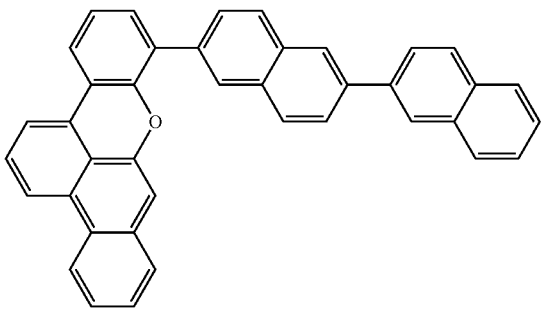
H-423
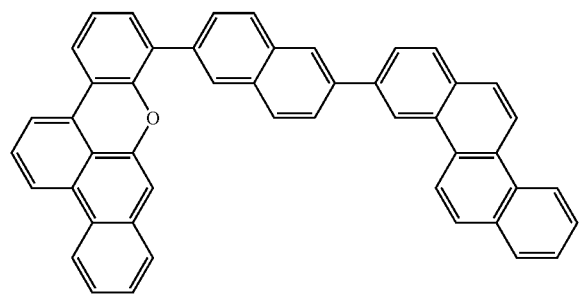
H-424
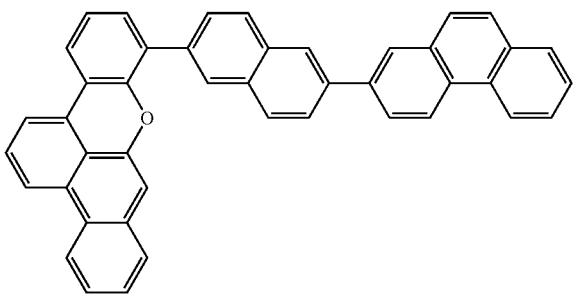
H-425
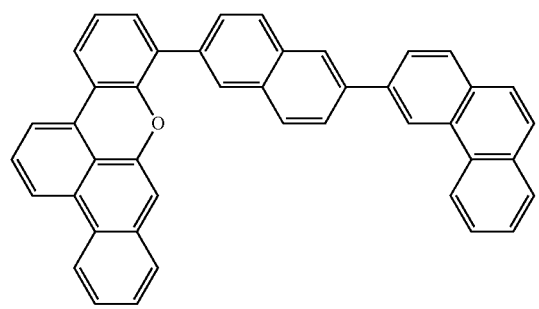
H-426
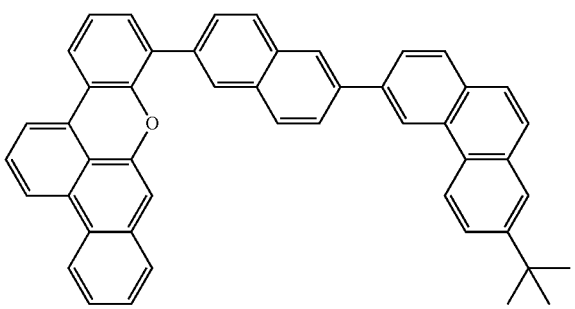
H-427
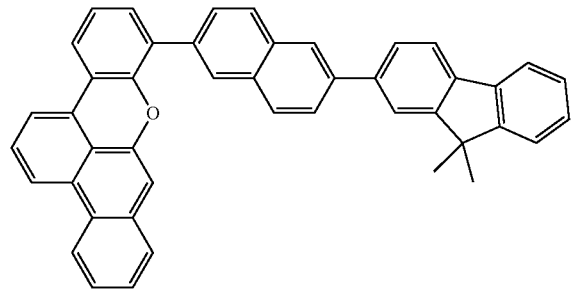
H-428
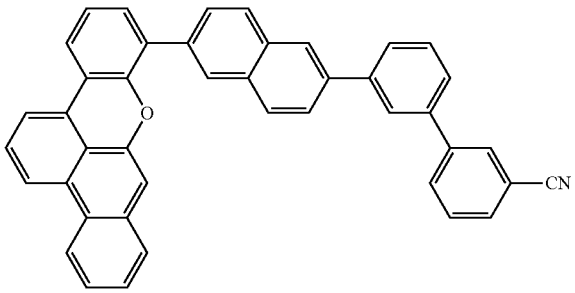
H-429
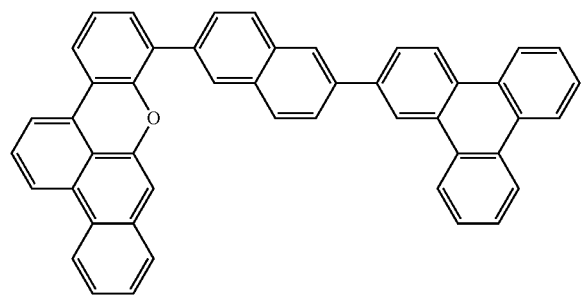
H-430
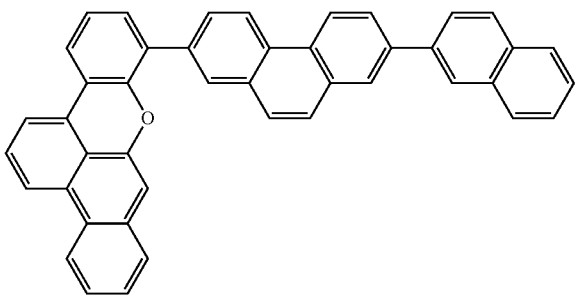

-continued
H-431
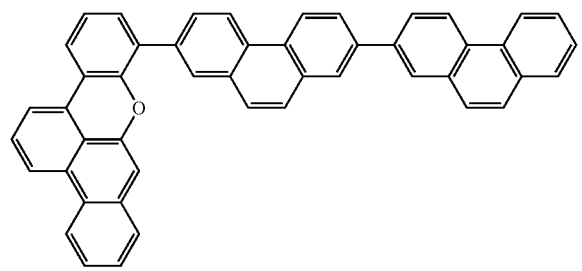
H-432
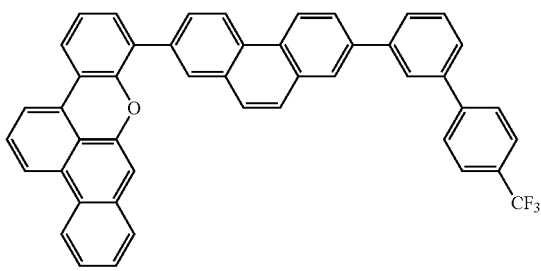
H-433
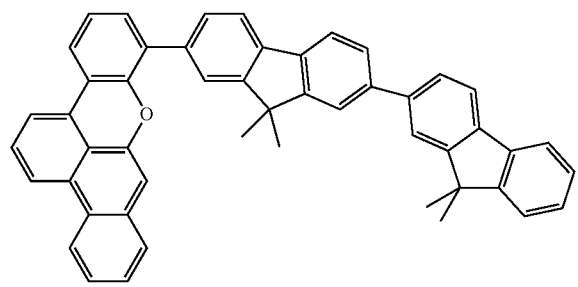
H-434
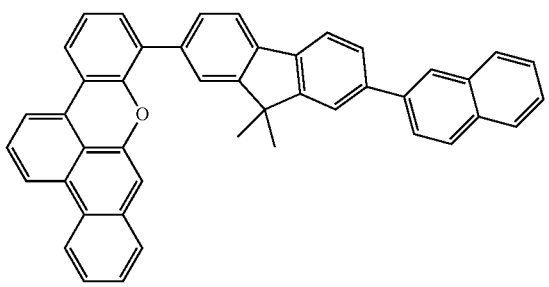
H-435
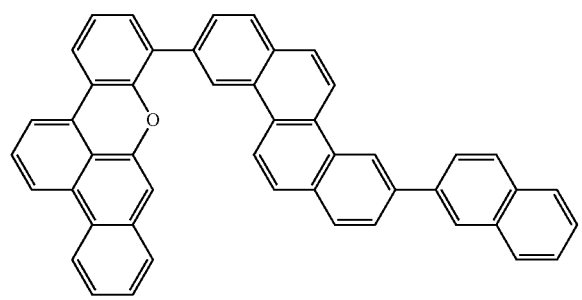
H-436
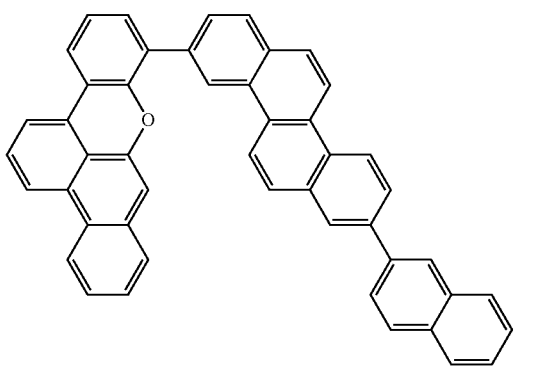
H-437
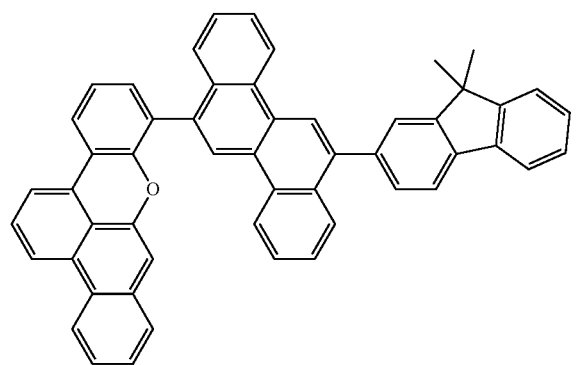
H-438
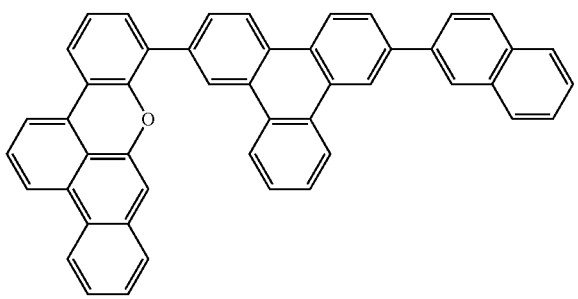

-continued
H-439
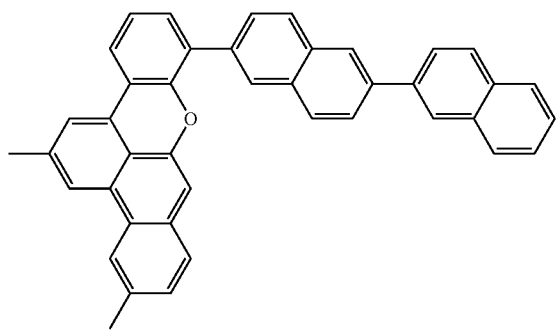
H-440
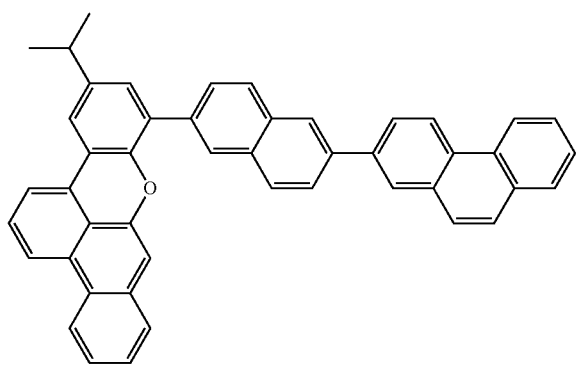
H-441
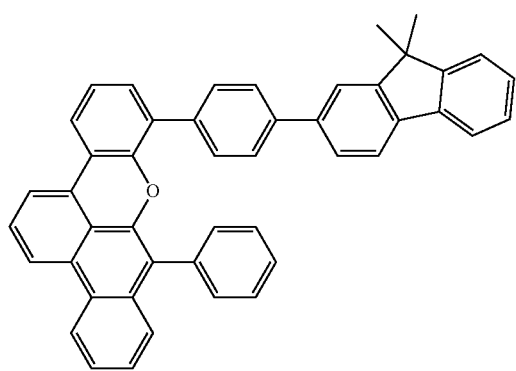
H-442
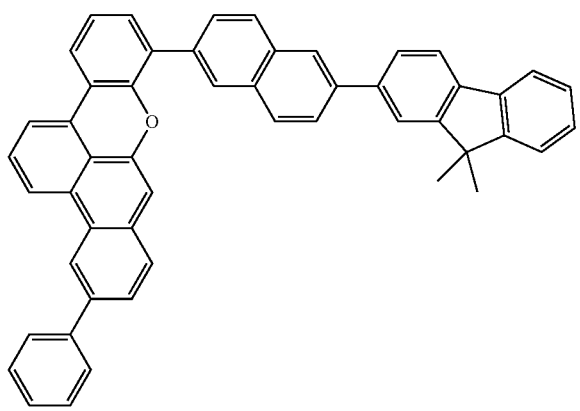
H-443
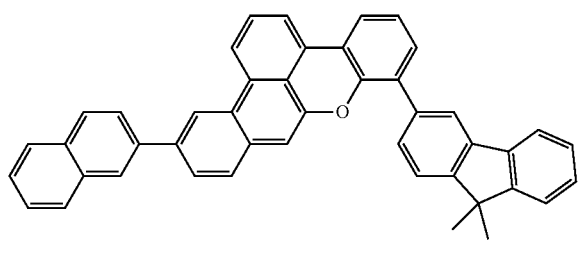
H-444
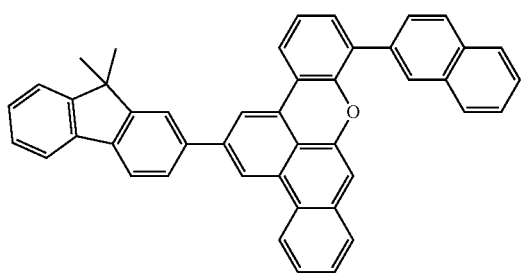
[Group 5 compound]
H-501
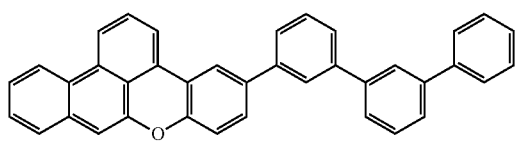
H-502
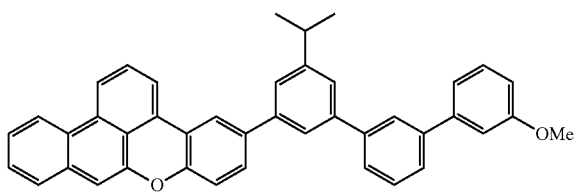

-continued
H-503
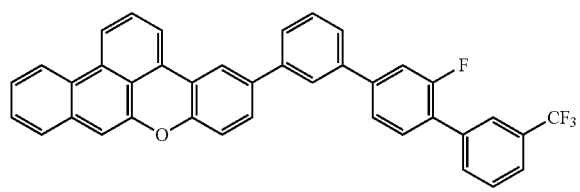
H-504
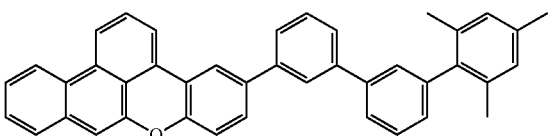
H-505
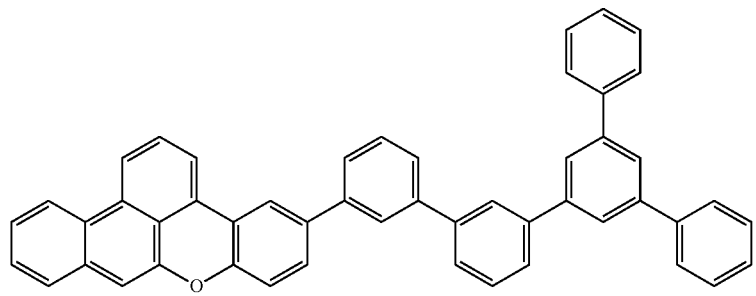
H-506
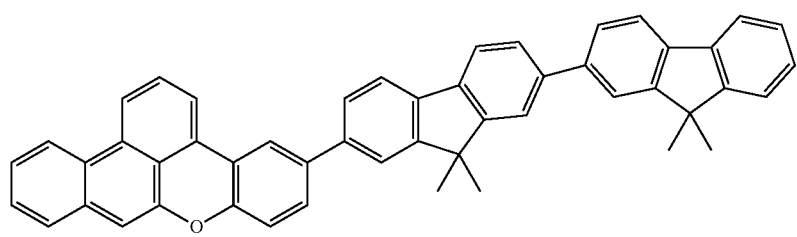
H-507
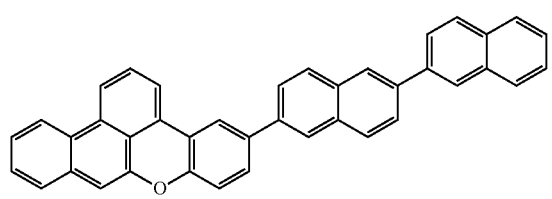
H-508
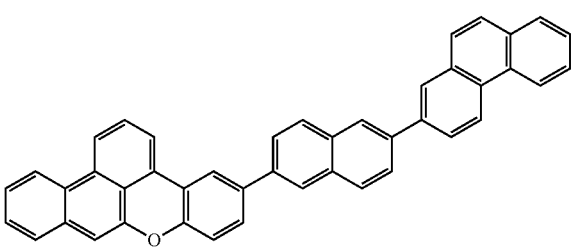
H-509
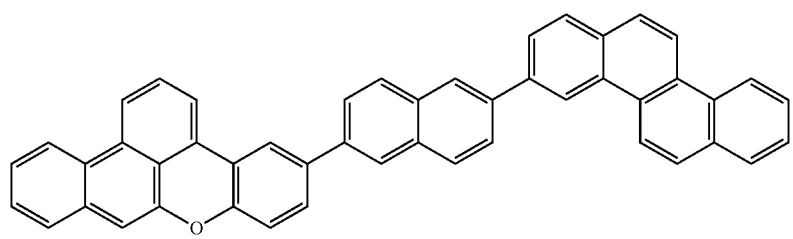
H-510
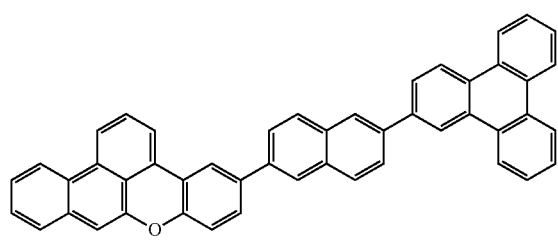
H-511
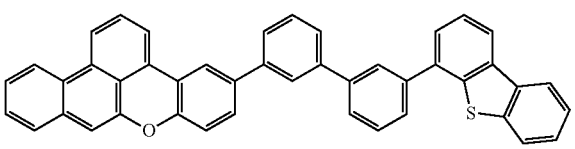

-continued
H-512
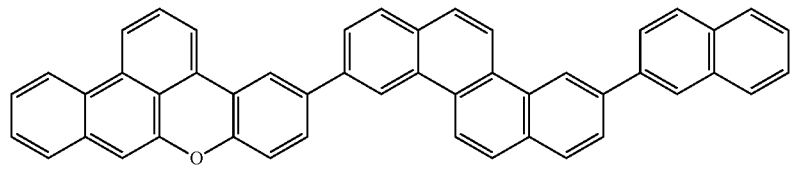
H-513 H-514
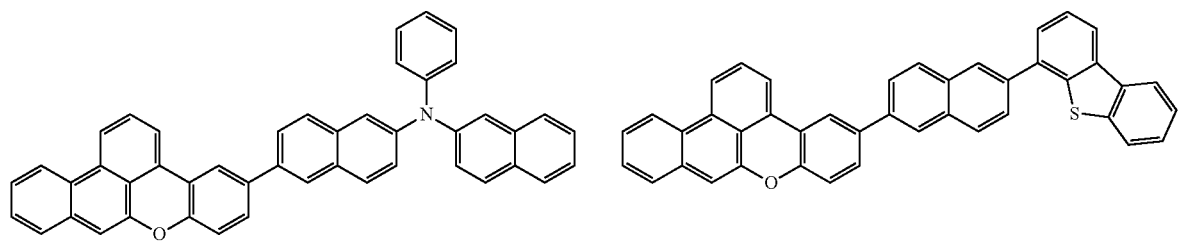
H-515 H-516
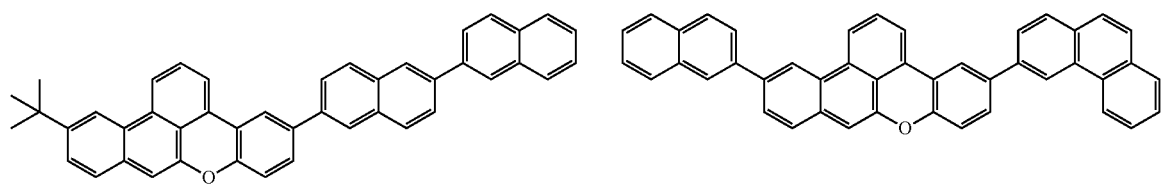
H-517 H-518
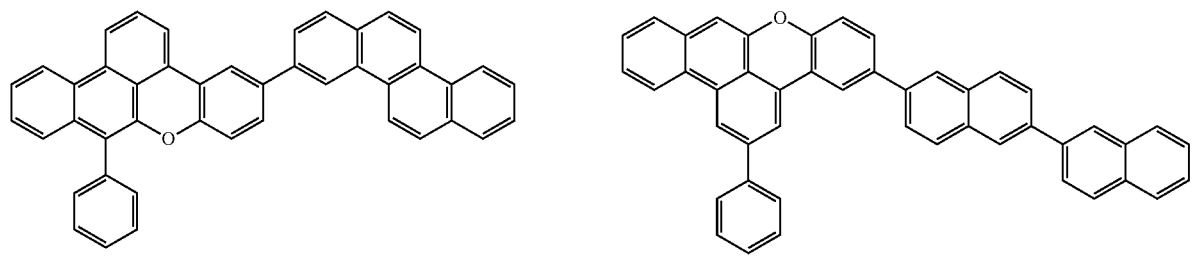
[Group 6 compound]
H-601 H-602
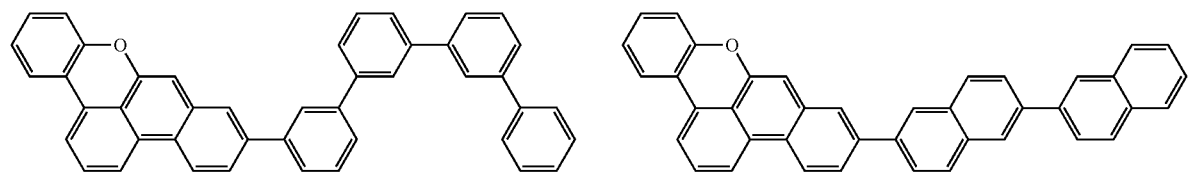
H-603 H-604
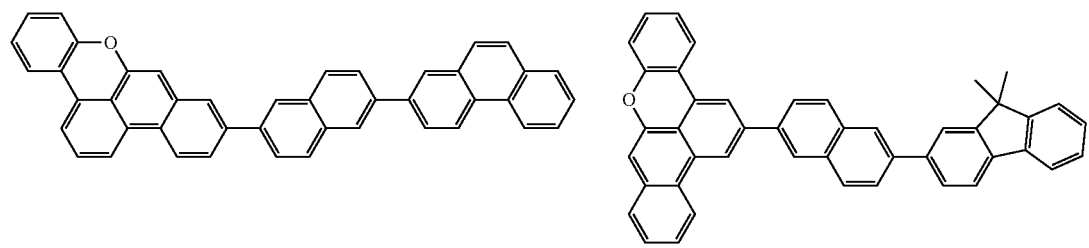

-continued
H-605
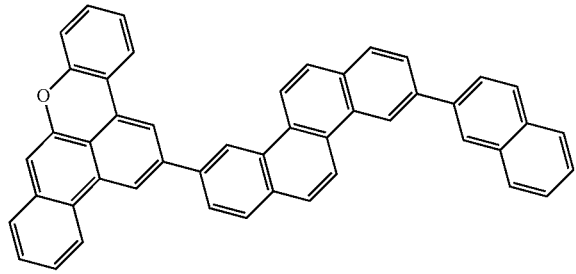
H-606
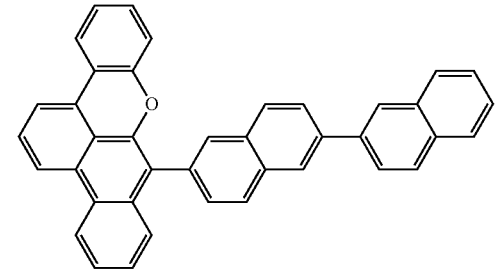
H-607
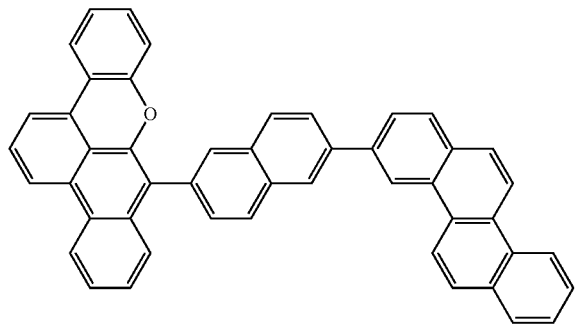
H-608
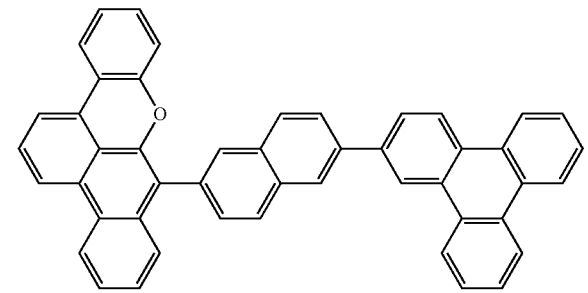
H-609
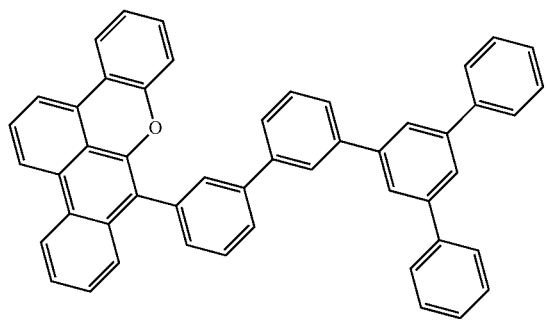
H-610
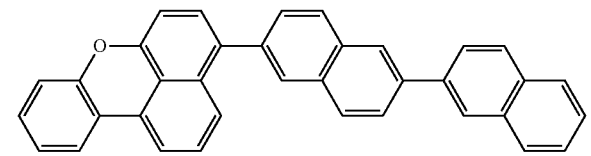
H-611
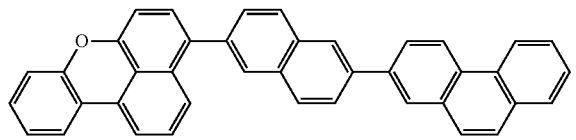
H-612
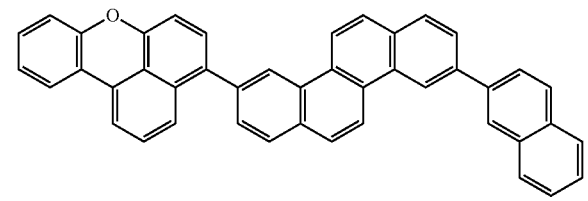
H-613
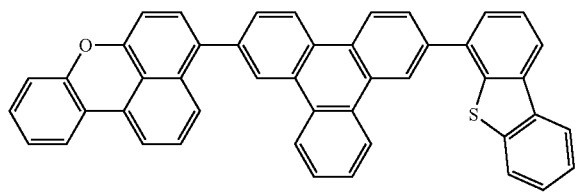
H-614
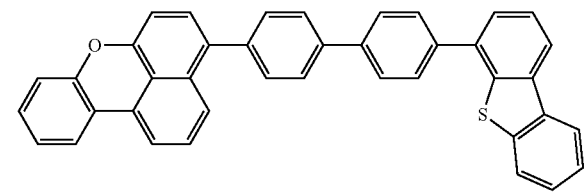

-continued
H-615
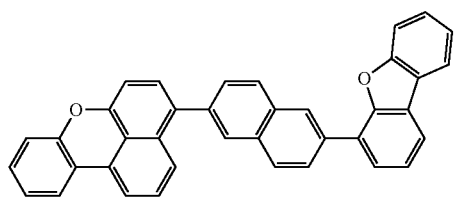
H-616
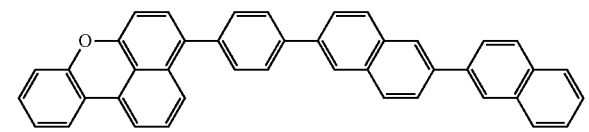
H-617
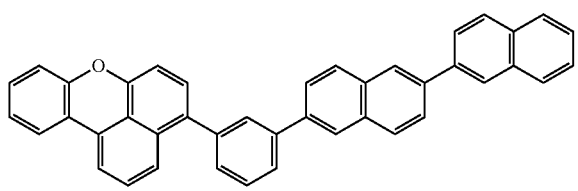
H-618
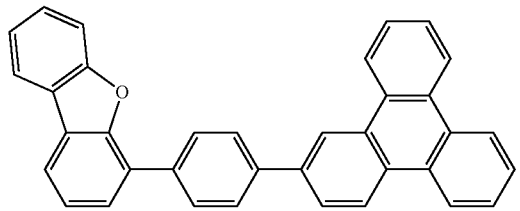
H-619
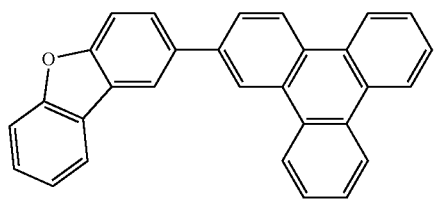
H-620
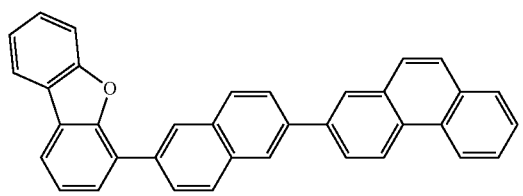
H-621
H-622
H-623
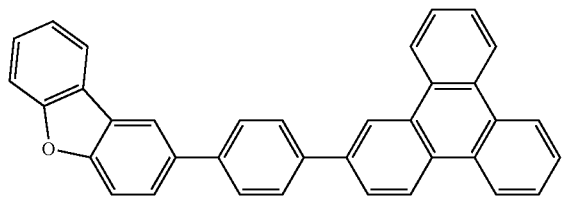
H-624
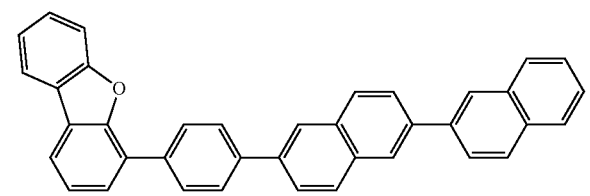
H-625
H-626

-continued
H-627
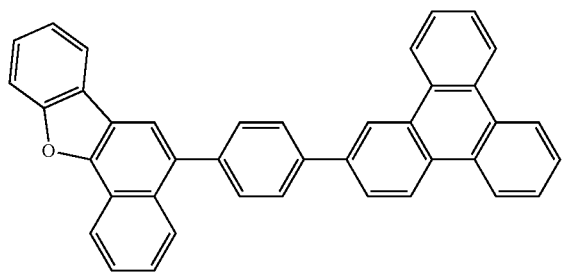
H-628
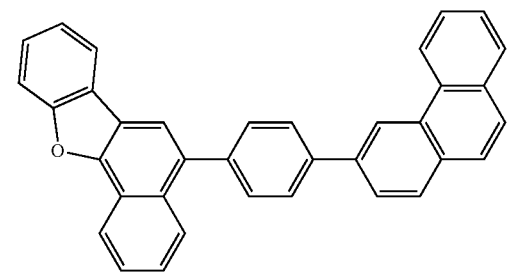
H-629
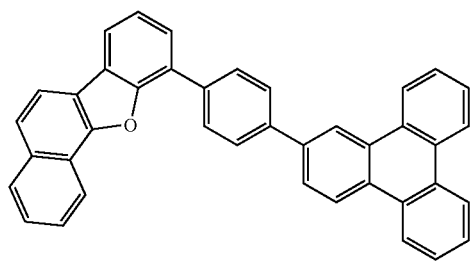
H-630
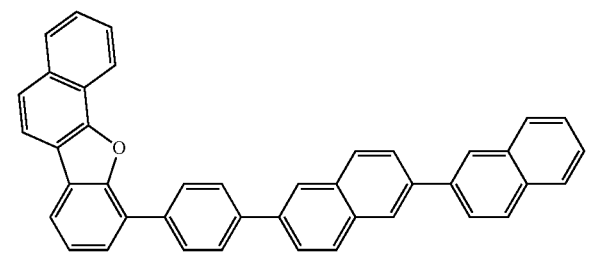
H-631
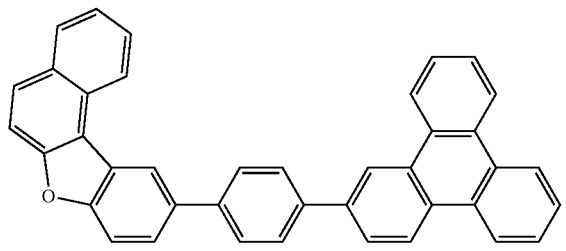
H-632
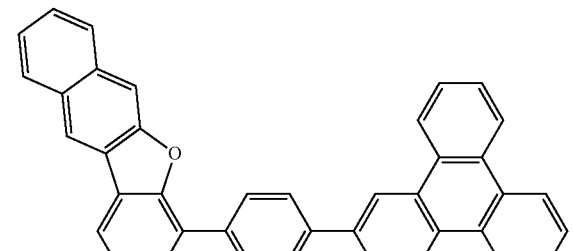
H-634
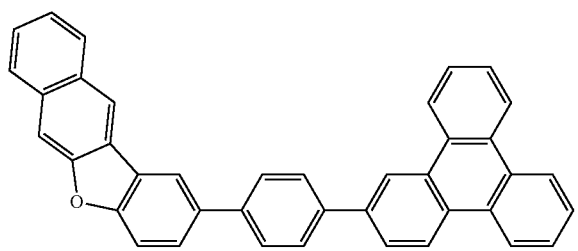
H-635
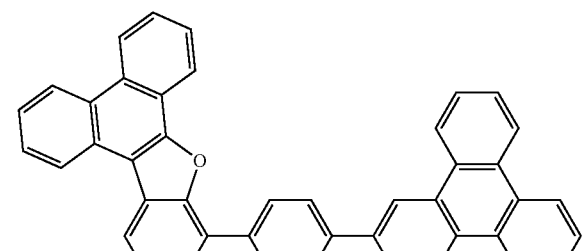
H-636
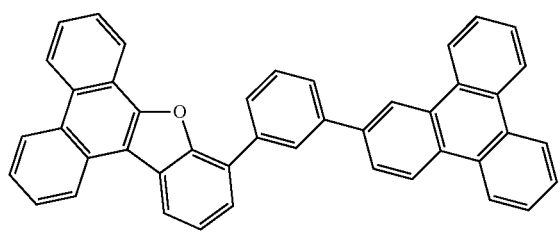
H-637
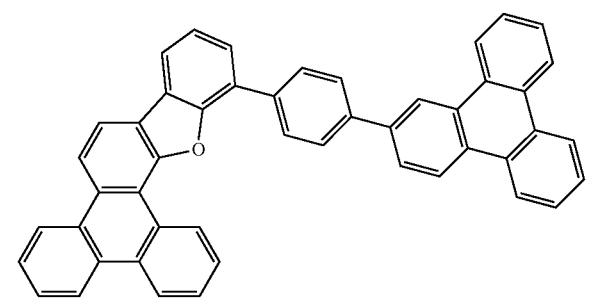

-continued
H-638
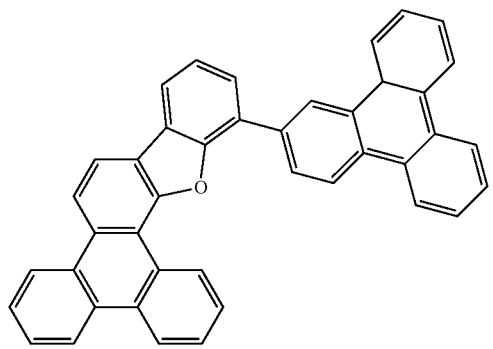
H-639
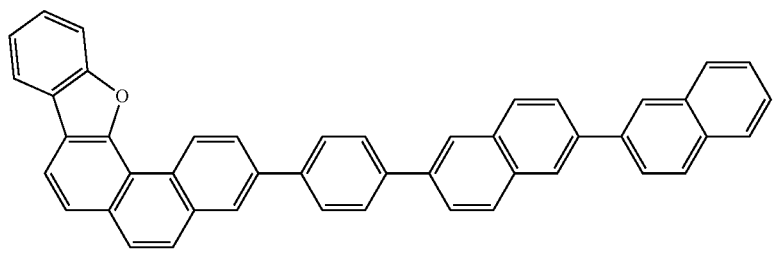
H-640
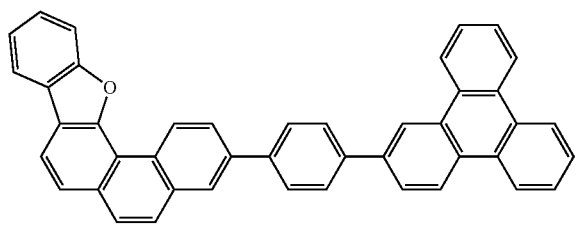
H-641
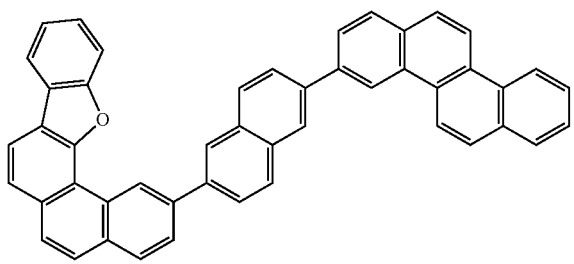
H-642
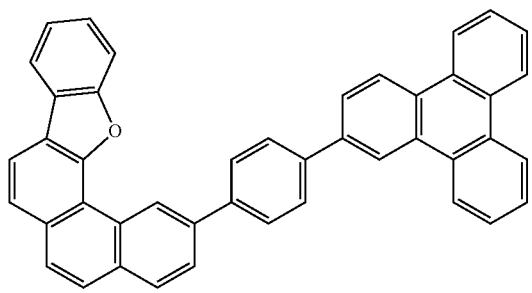
[Group 7 compound]
H-701
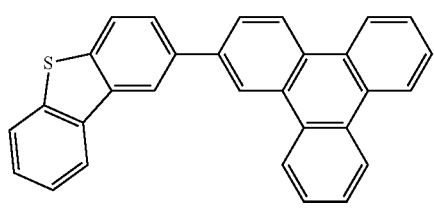
H-702
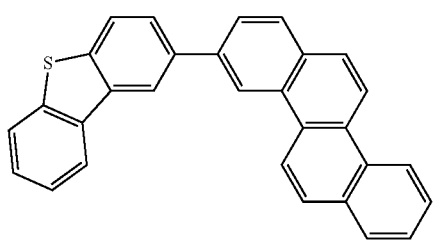

H-703
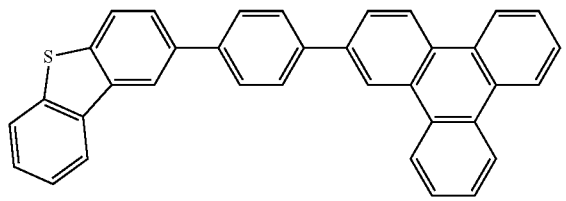
H-704
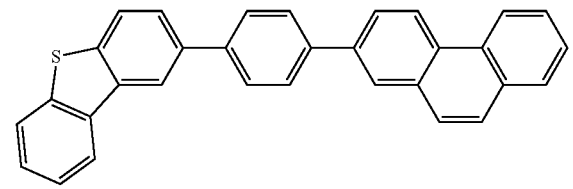
H-705
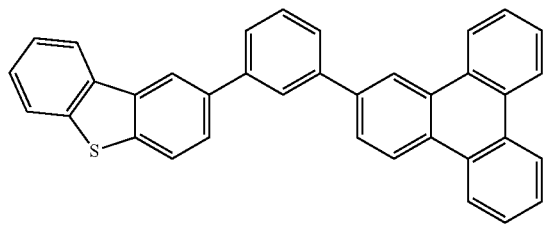
H-706
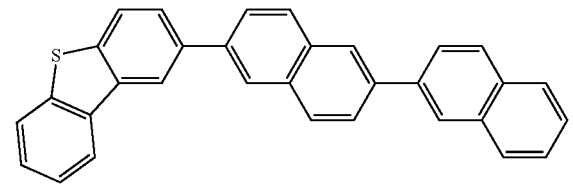
H-707
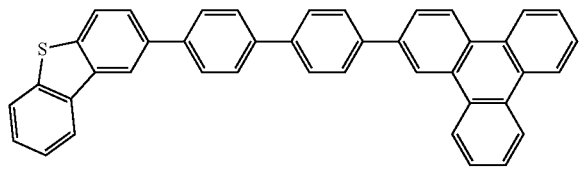
H-708
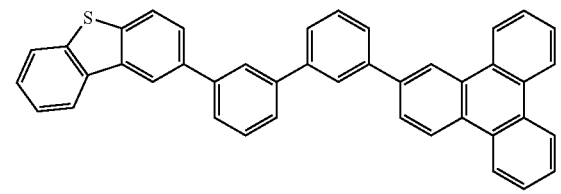
H-709
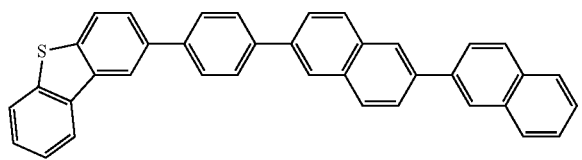
H-710
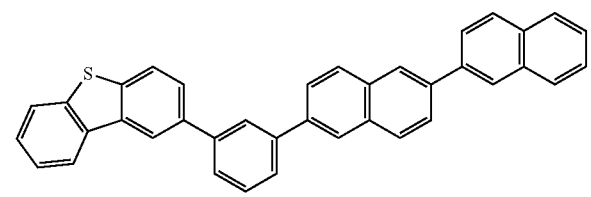
H-711
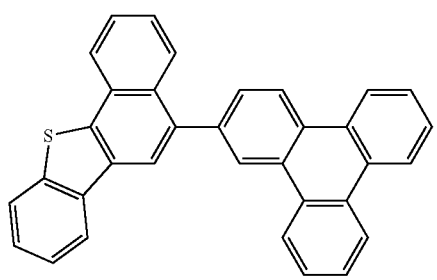
H-712
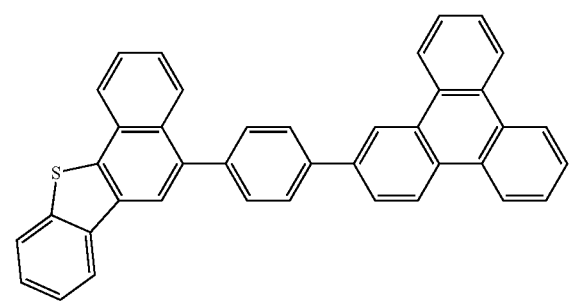
H-713
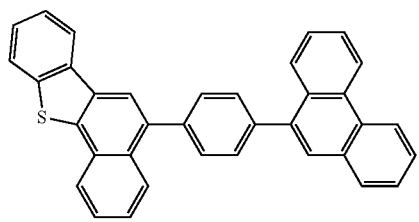
H-714
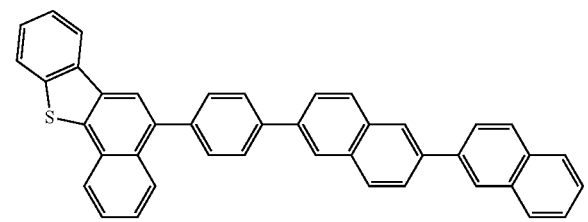

-continued
H-715
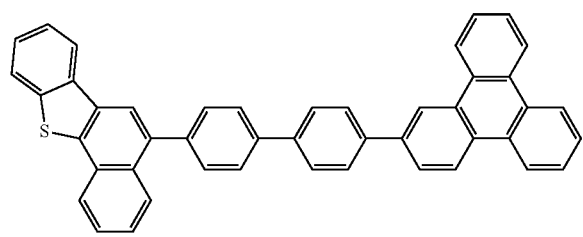
H-716
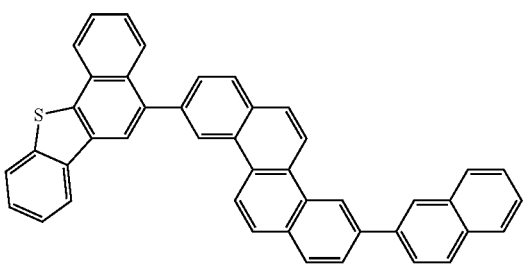
H-717
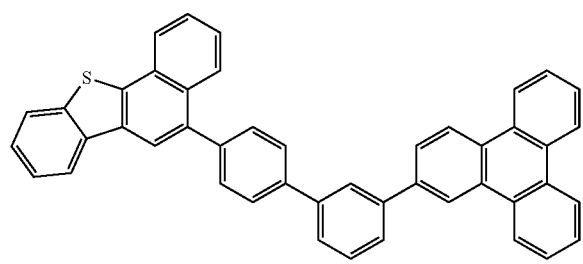
H-718
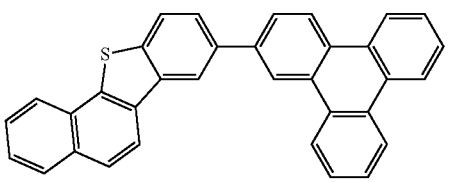
H-719
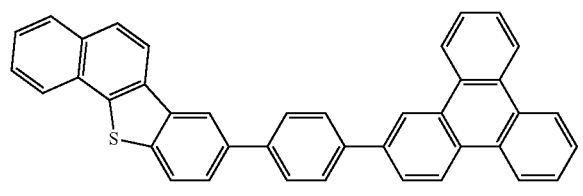
H-720
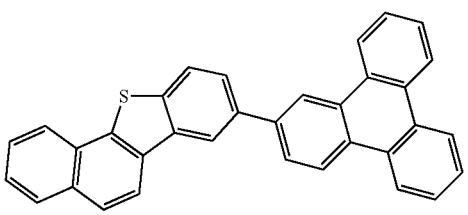
H-721
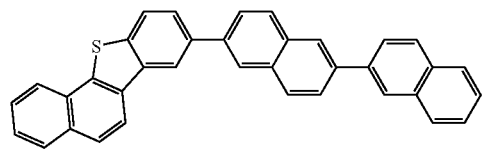
H-722
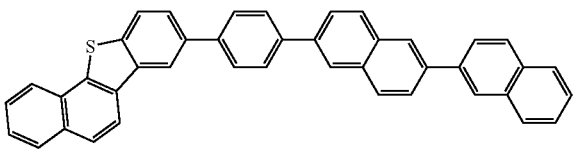
H-723
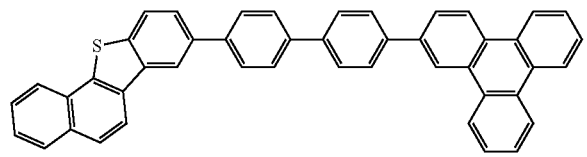
H-724
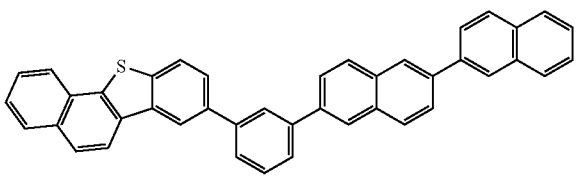
H-725
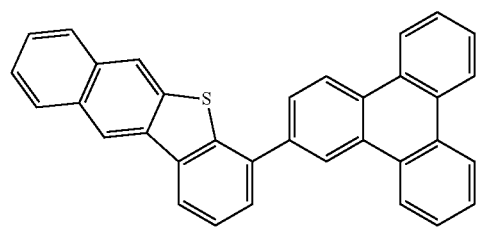
H-726
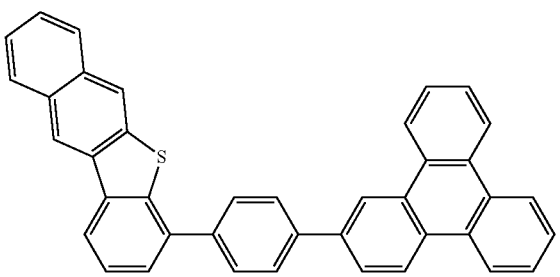

-continued
H-727
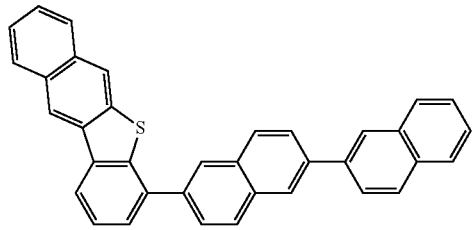
H-728
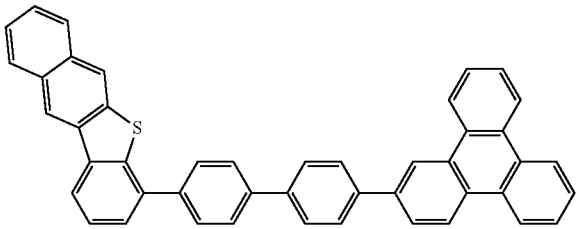
H-729
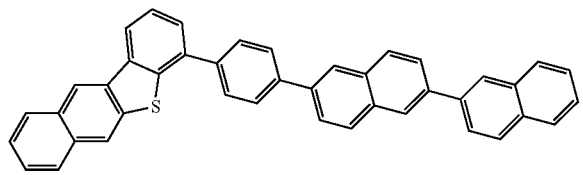
H-730
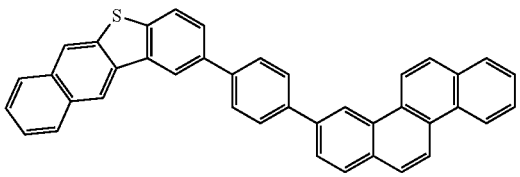
H-731
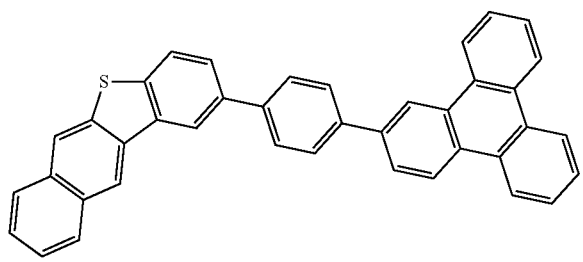
H-732
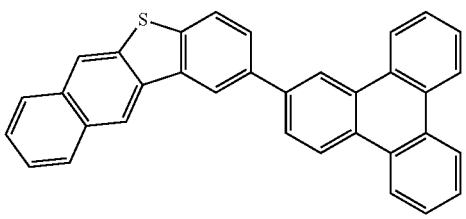
H-733
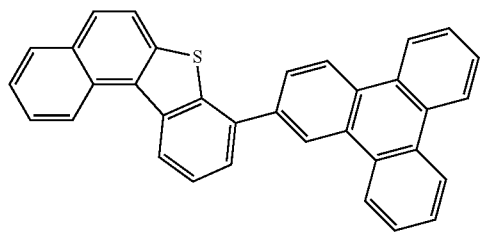
H-734
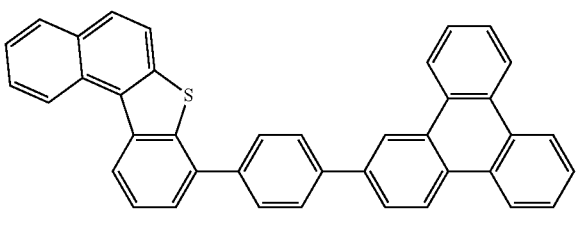
H-735
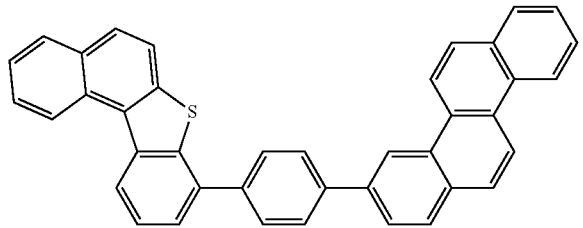
H-736
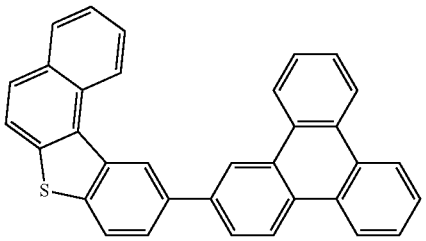
H-737
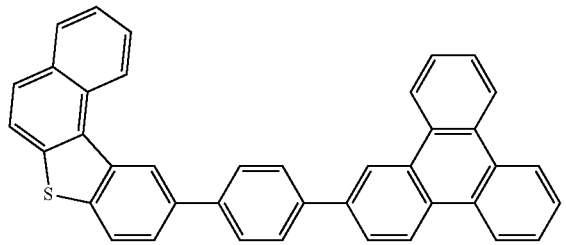
H-738
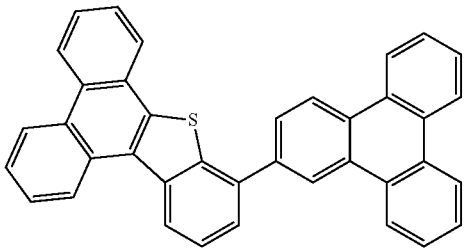

-continued
H-739
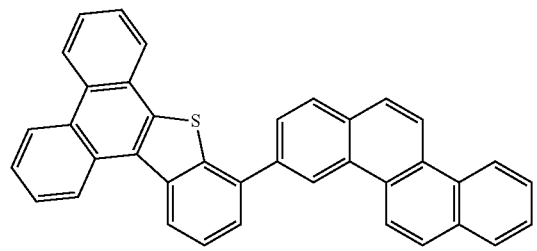
H-740
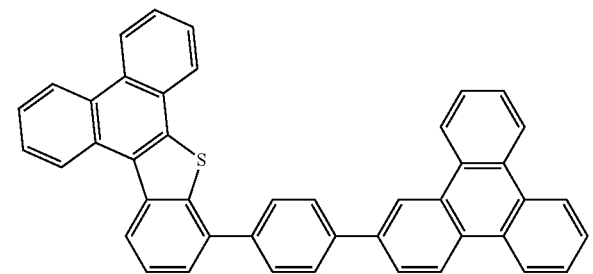
H-741
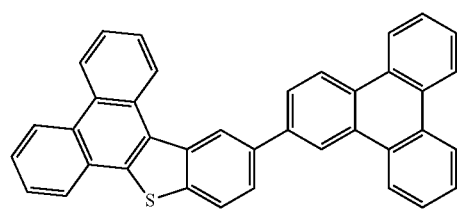
H-742
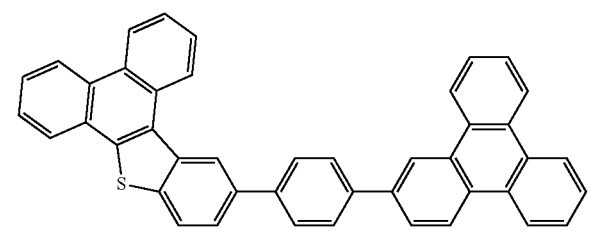
H-743
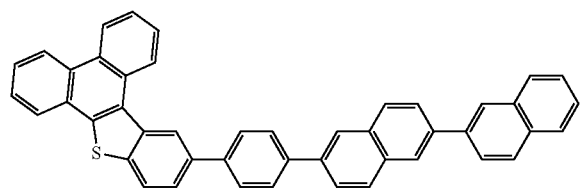
H-744
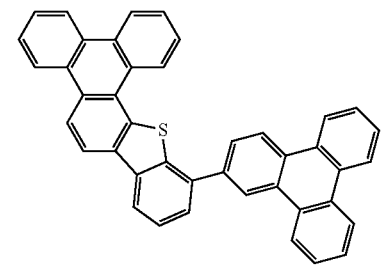
H-745
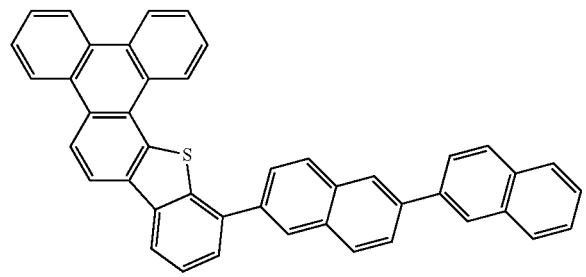
H-746
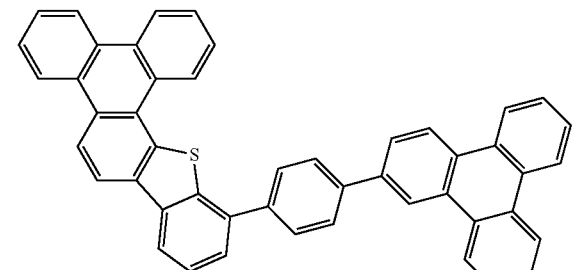
H-747
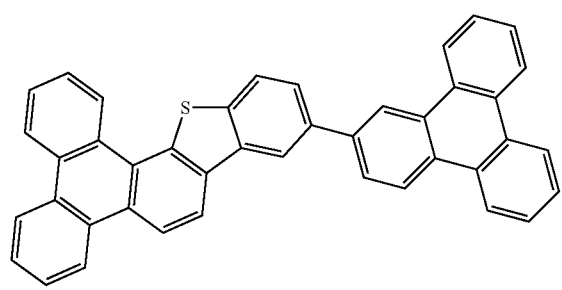

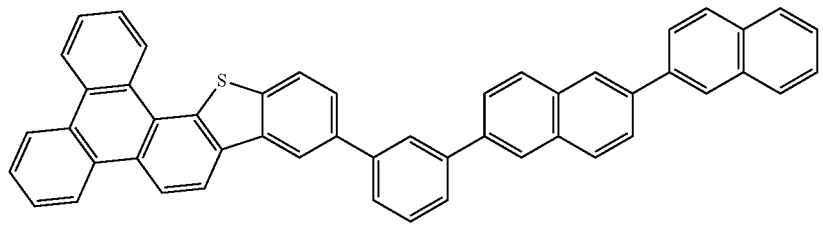

H-748

Of the exemplified compounds, the heterocycle-containing compounds represented by H-101 to H-158 are each a dibenzothiophene compound represented by the general formula [21]. Those heterocycle-containing compounds in the group 1 each have a moderately low hole mobility and high structural stability because the advantage of dibenzothiophene has been brought into play. Therefore, the incorporation of any one of those heterocycle-containing compounds in the group 1 as the host into the light-emitting layer optimizes a carrier balance between the host and guest (iridium complex represented by the general formula [1]) in the light-emitting layer. Therefore, an organic light-emitting element having high luminous efficiency and a long lifetime is obtained.

Of the exemplified compounds, the heterocycle-containing compounds represented by H-201 to H-229 are each a benzonaphthothiophene compound represented by the general formula [22]. As in the heterocycle-containing compounds in the group 1, those heterocycle-containing compounds in the group 2 can each also optimize the carrier balance between the host and guest (iridium complex represented by the general formula [1]) in the light-emitting layer. Therefore, an organic light-emitting element having high luminous efficiency and a long lifetime is obtained. In addition, the $S_1$ energy (HOMO-LUMO energy gap) of each heterocycle-containing compound in the group 2 is smaller than that of each heterocycle-containing compound in the group 1 because the π conjugation of benzonaphthothiophene is larger than that of dibenzothiophene. Therefore, the incorporation of the compound as the host into the light-emitting layer can reduce the driving voltage of the light-emitting element because the introduction reduces a carrier injection barrier from the carrier-transporting layer.

Of the exemplified compounds, the heterocycle-containing compounds represented by H-301 to H-329 are each a benzophenanthrothiophene compound represented by the general formula [23]. As in the heterocycle-containing compounds in the group 1 and the group 2, those heterocycle-containing compounds in the group 3 can each also optimize the carrier balance between the host and guest (iridium complex represented by the general formula [1]) in the light-emitting layer. Therefore, an organic light-emitting element having high luminous efficiency and a long lifetime is obtained. In addition, the π conjugation of benzophenanthrothiophene is larger than those of benzonaphthothiophene and dibenzothiophene. Therefore, for the same reason as described above, the driving voltage of the light-emitting element can be reduced more.

Of the exemplified compounds, the heterocycle-containing compounds represented by H-401 to H-444 are each a dibenzoxanthene compound represented by the general formula [24]. Those heterocycle-containing compounds in the group 4 each have a moderately low hole mobility, high structural stability, and a relatively shallow HOMO level because the advantage of dibenzoxanthene has been brought into play. As in the heterocycle-containing compounds in the group 1 to the group 3, the incorporation of any one of those heterocycle-containing compounds in the group 4 as the host into the light-emitting layer can also optimize the carrier balance between the host and guest (iridium complex represented by the general formula [1]) in the light-emitting layer. Therefore, an organic light-emitting element having high luminous efficiency and a long lifetime is obtained.

Of the exemplified compounds, the heterocycle-containing compounds represented by H-501 to H-518 are each a dibenzoxanthene compound represented by the general formula [25]. As in the heterocycle-containing compounds in the group 4, the incorporation of any one of those heterocycle-containing compounds in the group 5 as the host into the light-emitting layer can also optimize the carrier balance between the host and guest (iridium complex represented by the general formula [1]) in the light-emitting layer. Therefore, an organic light-emitting element having high luminous efficiency and a long lifetime is obtained.

Of the exemplified compounds, the heterocycle-containing compounds represented by H-601 to H-642 are each a compound having an oxygen-containing heterocycle in which Z represents an oxygen atom out of the heterocycle-containing compounds each represented by the general formula [5]. In this regard, the compounds in the group (group 6) are each an oxygen-containing heterocycle-containing compound except the dibenzoxanthene compounds represented by the general formulae [24] and [25]. Those heterocycle-containing compounds in the group 6 are each a compound having high structural stability as in the heterocycle-containing compounds in the group 1 to the group 5, and are each a compound having a relatively shallow HOMO level because the electron-donating property of the oxygen atom comes into play. As in the heterocycle-containing compounds in the group 1 to the group 5, the incorporation of any one of those heterocycle-containing compounds in the group 6 as the host into the light-emitting layer can also optimize the carrier balance between the host and guest (iridium complex represented by the general formula [1]) in the light-emitting layer. Therefore, an organic light-emitting element having high luminous efficiency and a long lifetime is obtained.

Of the exemplified compounds, the heterocycle-containing compounds represented by H-701 to H-748 are each a sulfur-containing heterocycle-containing compound in which Z in the general formula [5] represents a sulfur atom, and that does not correspond to the benzo-fused thiophene compounds represented by the general formulae [21] to [23] out of the heterocycle-containing compounds each represented by the general formula [5]. As in the heterocycle-containing compounds in the group 1 to the group 5, those heterocycle-containing compounds in the group 7 are each a compound having high structural stability. In addition, the compounds are each a compound having a relatively small S₁ energy because the compound contains the sulfur atom in a molecule thereof. As in the heterocycle-containing compounds in the group 1 to the group 6, the incorporation of any one of those heterocycle-containing compounds in the group 7 as the host into the light-emitting layer can also optimize the carrier balance between the host and guest (iridium complex represented by the general formula [1]) in the light-emitting layer. Therefore, an organic light-emitting element having high luminous efficiency and a long lifetime is obtained. In addition, the incorporation of any one of the heterocycle-containing compounds in the group 7 as the host into the light-emitting layer can reduce the driving voltage.

(7) Constituent Material Except Iridium Complex and Heterocycle-Containing Compound As described above, the organic compound layer (preferably the light-emitting layer) of the organic light-emitting element of the present invention contains at least the iridium complex represented by the general formula [1] and the heterocycle-containing compound represented by the general formula [5]. However, in the present invention, conventionally known low-molecular weight and high-molecular weight materials can each be used as required in addition to these compounds. More specifically, a hole-injectable/transportable material, a light emission assist material, an electron-injectable/transportable material, or the like can be used together with the iridium complex and the heterocycle-containing compound.

Examples of those materials are listed below.

The hole-injectable/transportable material is preferably a material having a high hole mobility so that the injection of a hole from the anode may be facilitated and the injected hole can be transported to the light-emitting layer. In addition, the material is preferably a material having a high glass transition point for preventing the deterioration of film quality such as crystallization in the organic light-emitting element. Examples of the low-molecular weight and high-molecular weight materials each having hole-injecting/transporting performance include a triarylamine derivative, an arylcarbazole derivative, a phenylenediamine derivative, a stilbene derivative, a phthalocyanine derivative, a porphyrin derivative, poly(vinyl carbazole), poly(thiophene), and other conductive polymers. Further, the hole-injectable/transportable material is suitably used for the electron-blocking layer as well.

Specific examples of a compound to be used as the hole-injectable/transportable material are shown below. However, the compound is of course not limited thereto.

HT1

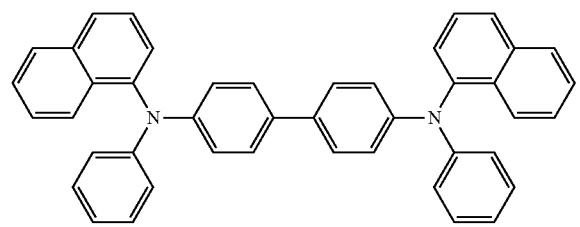

HT2

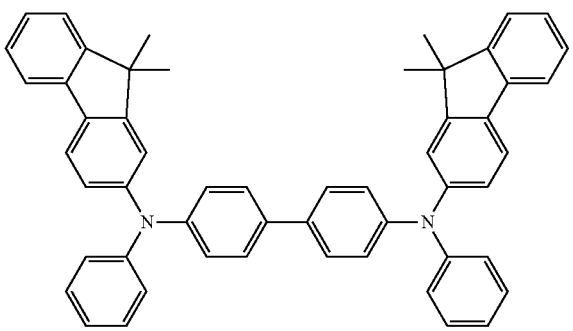

HT3

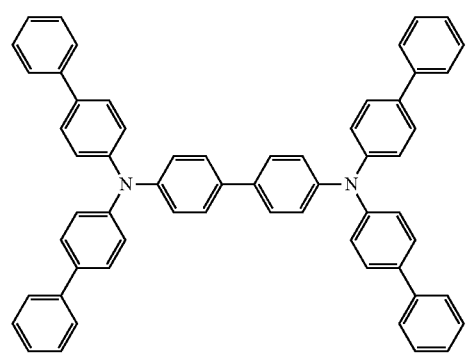

HT4

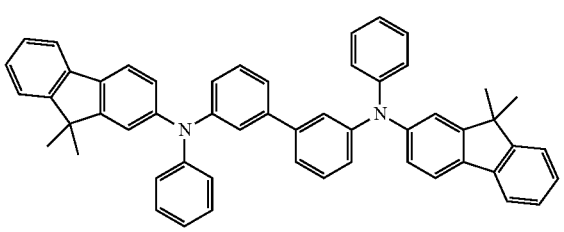

-continued
HT5
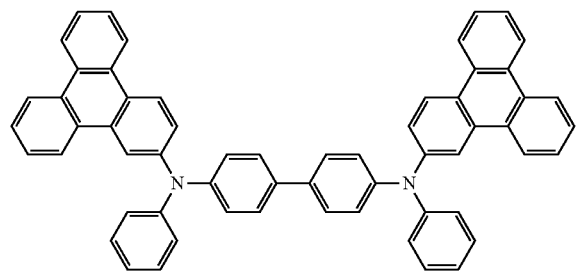
HT6
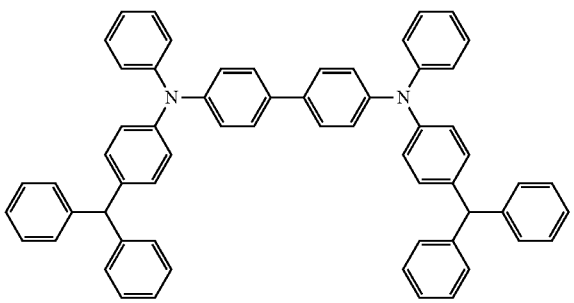
HT7
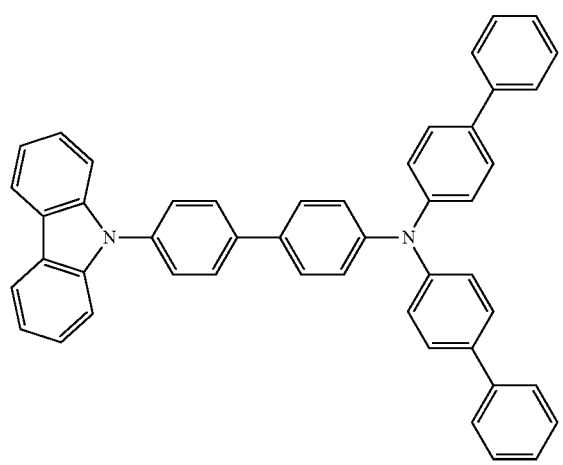
HT8
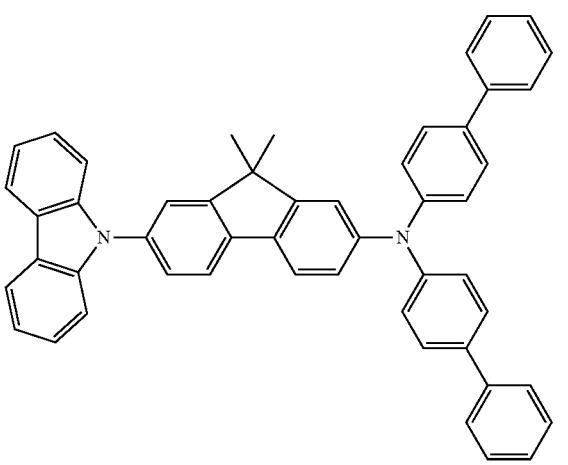
HT9
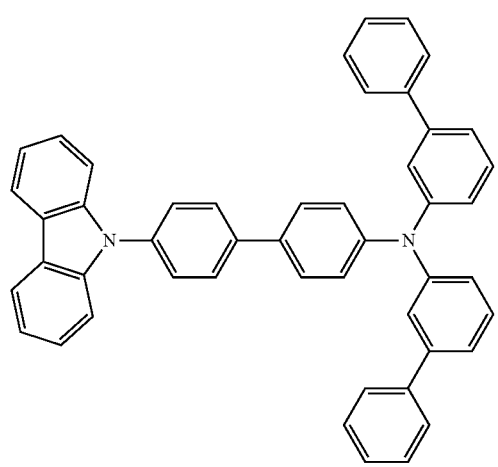
HT10
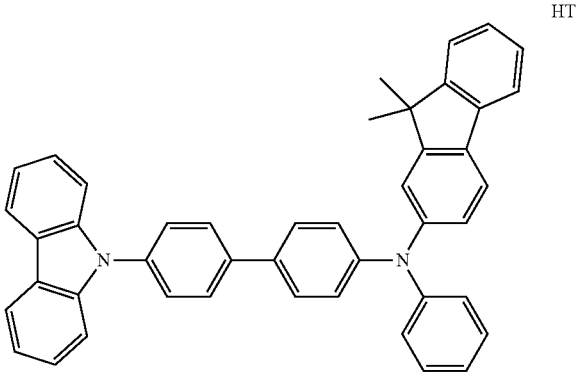
HT11
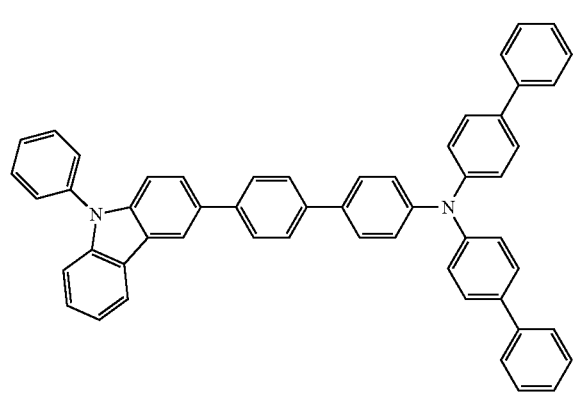
HT12
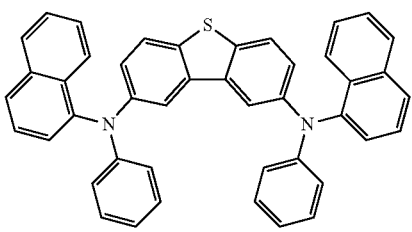

HT13

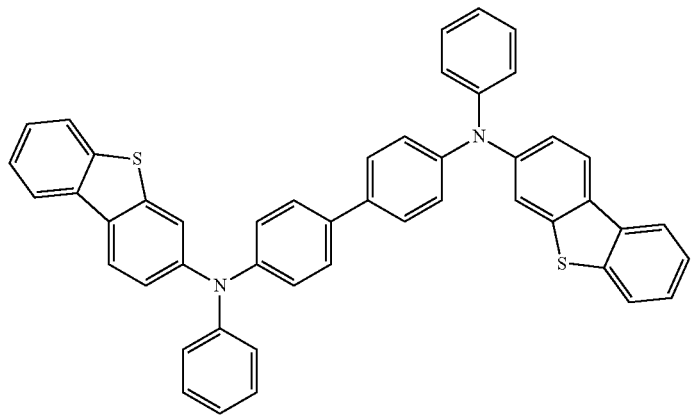

HT14

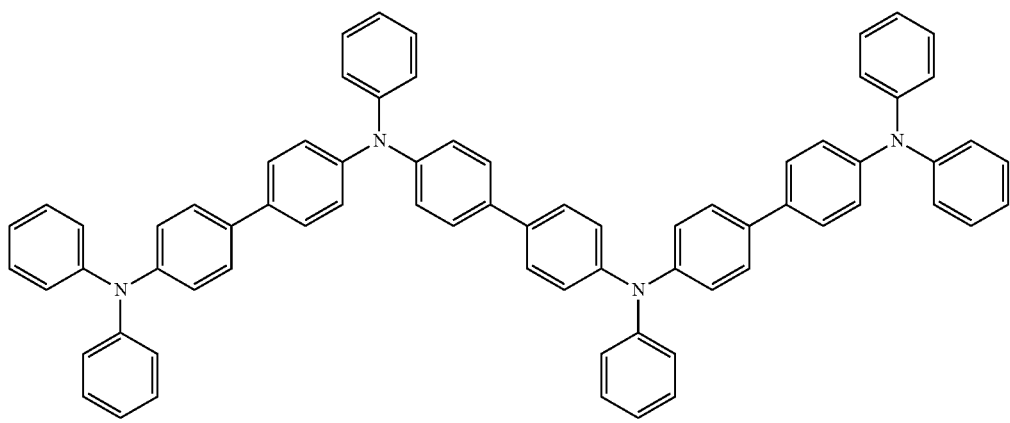

Examples of the light-emitting material mainly involved in a light-emitting function include: condensed ring compounds (such as a fluorene derivative, a naphthalene derivative, a pyrene derivative, a perylene derivative, a tetracene derivative, an anthracene derivative, and rubrene); a quinacridone derivative; a coumarin derivative; a stilbene derivative; an organic aluminum complex such as tris(8-quinolinolato)aluminum; a platinum complex; a rhenium complex; a copper complex; a europium complex; a ruthenium complex; and polymer derivatives such as a poly(phenylene vinylene) derivative, a poly(fluorene) derivative, and a poly(phenylene) derivative in addition to the iridium complex represented by the general formula [1] or a derivative thereof.

Specific examples of a compound to be used as the light-emitting material are shown below. However, the compound is of course not limited thereto.

BD1

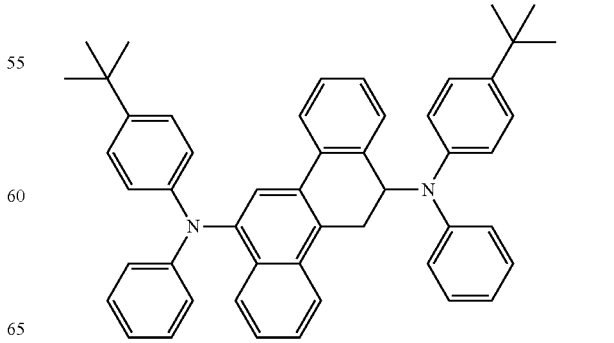

BD2
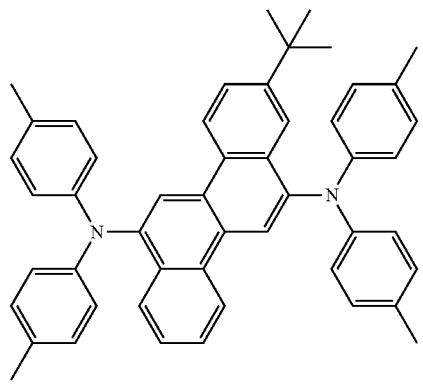
BD6
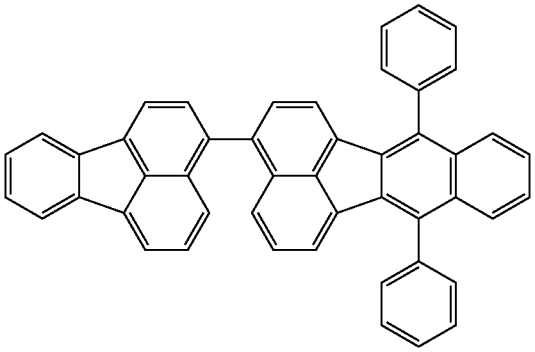
BD3
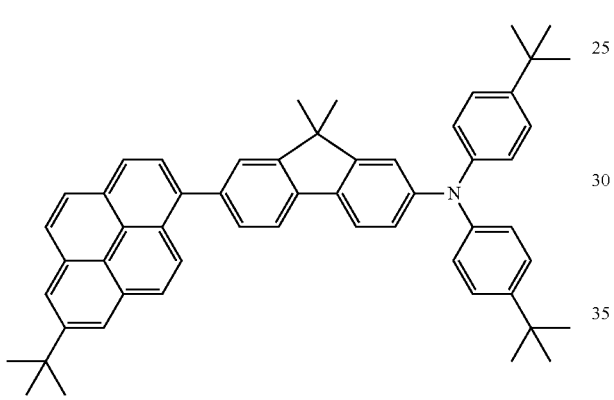
BD7
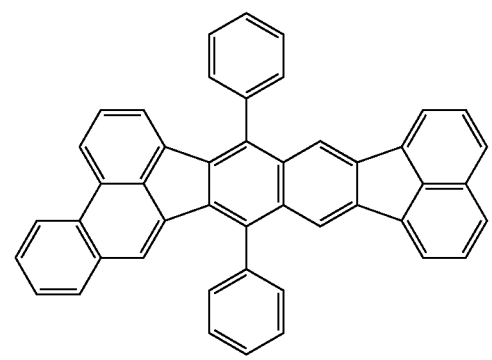
BD8
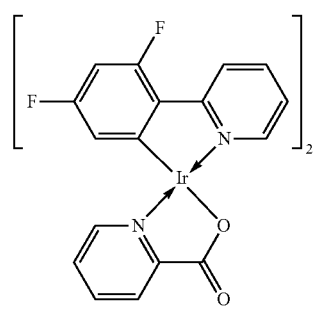
BD4
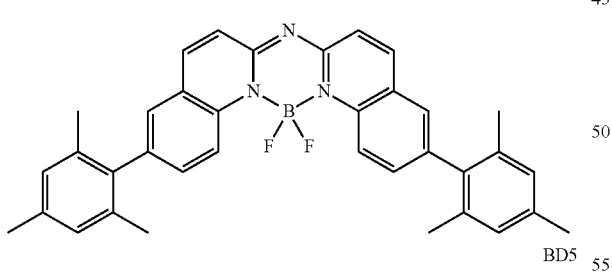
GD1
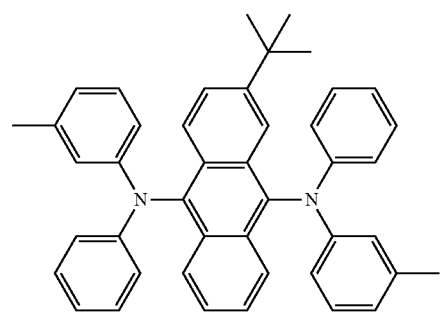
BD5
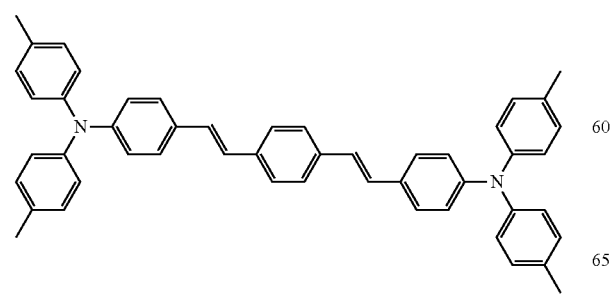
GD2
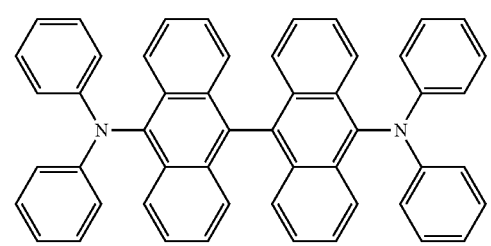

GD3
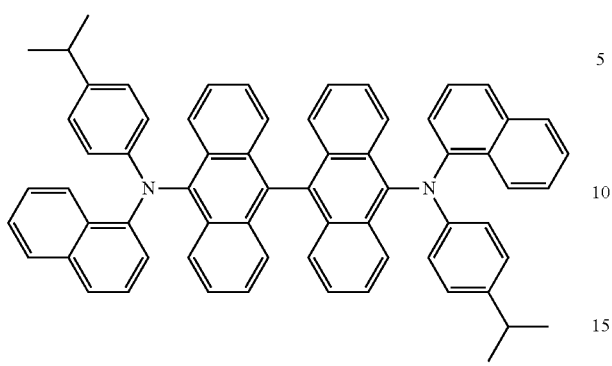
GD8
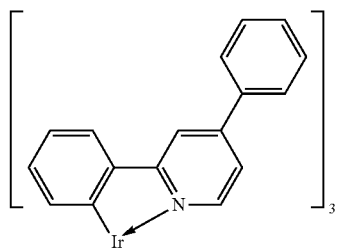
GD4
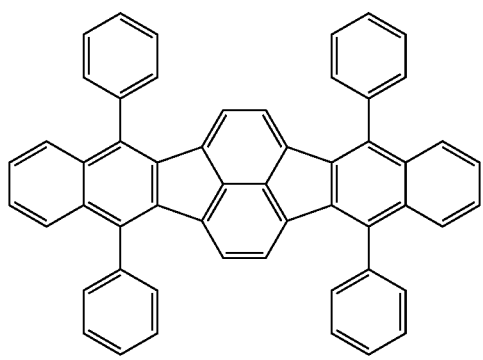
RD1
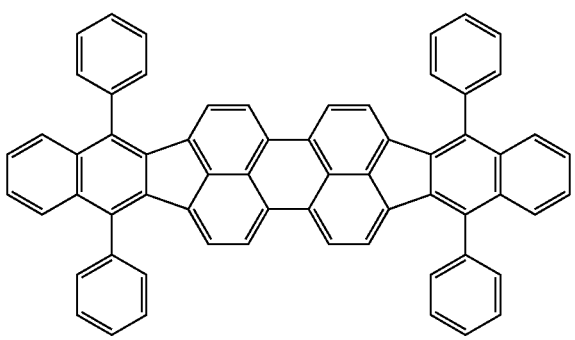
GD5
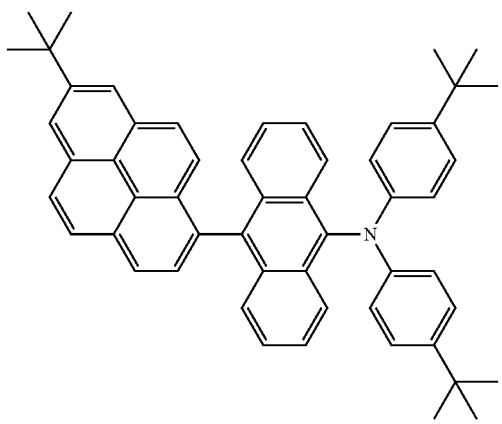
RD2
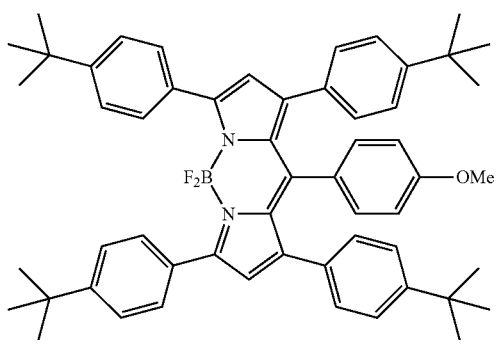
GD6
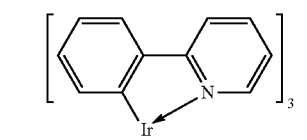
GD7
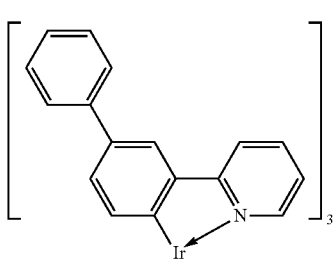
RD3
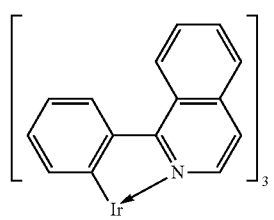

RD4
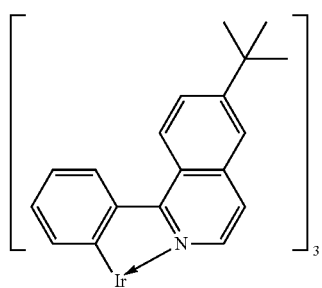

RD5
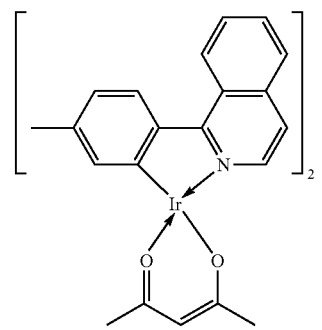

RD6
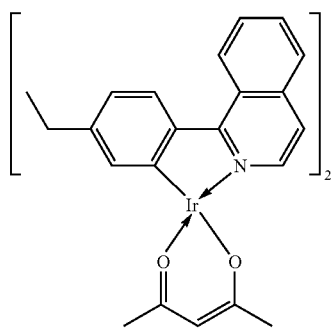

RD7
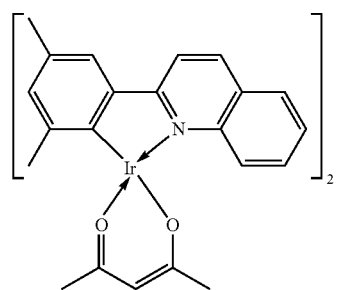

RD8
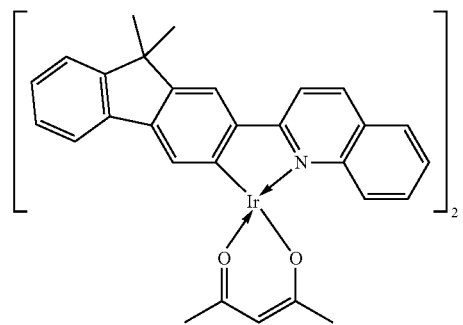

Examples of the host or assist material to be incorporated into the light-emitting layer include: an aromatic hydrocarbon compound or a derivative thereof; a carbazole derivative; a dibenzofuran derivative; a dibenzothiophene derivative; an organic aluminum complex such as tris(8-quinolinolato)aluminum; and an organic beryllium complex in addition to the heterocycle-containing compound represented the general formula [5].

Specific examples of a compound to be used as the host or assist material to be incorporated into the light-emitting layer are shown below. However, the compound is of course not limited thereto.

EM1
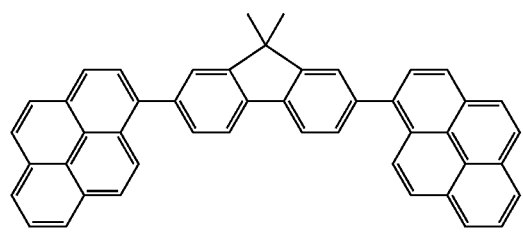

EM2
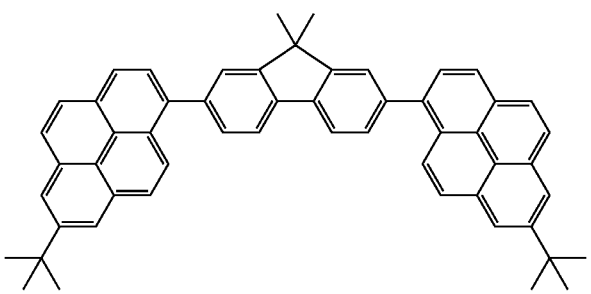

EM3
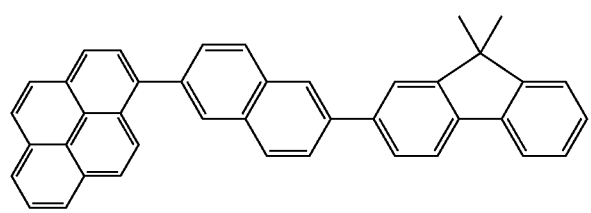

EM4
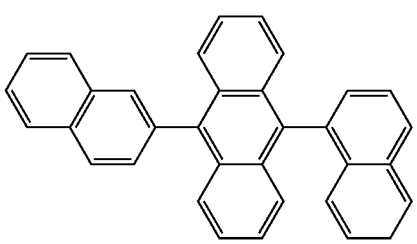

-continued
EM5
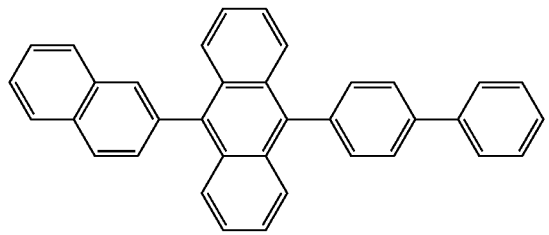
EM6
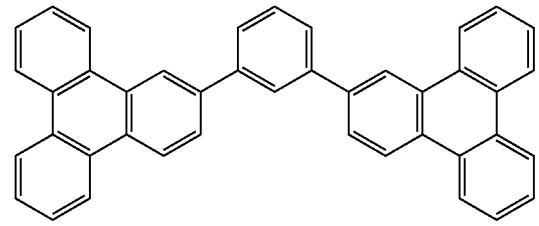
EM7
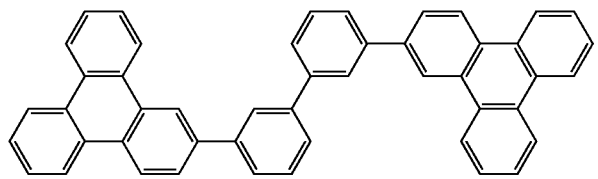
EM8
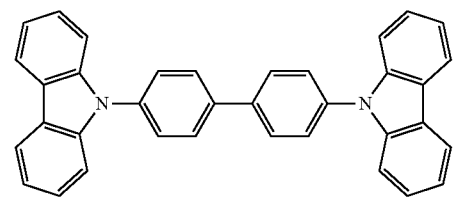
EM9
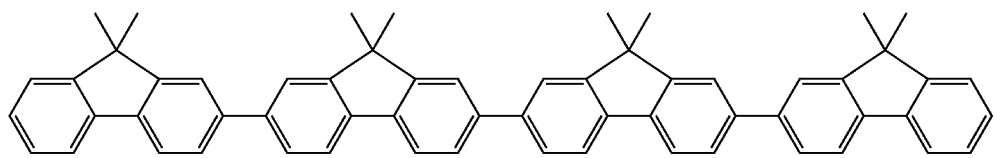
EM10
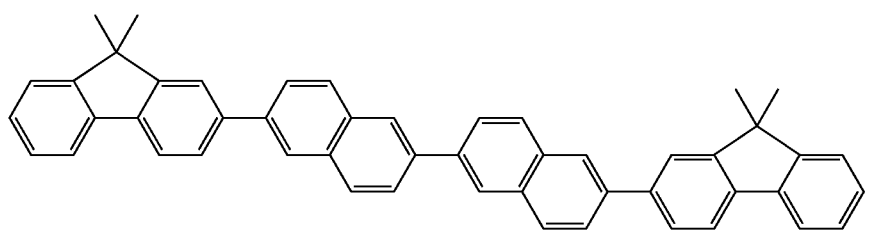
EM11
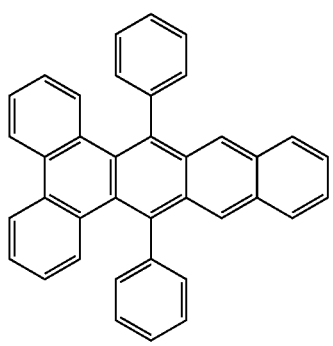
EM12
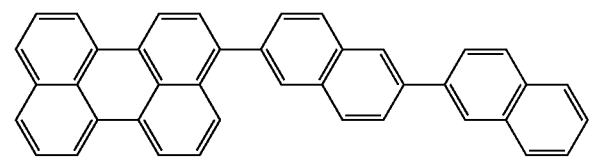
EM13
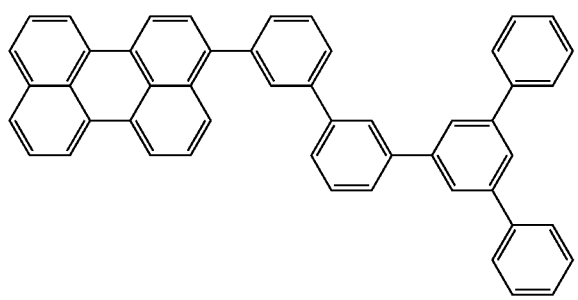
EM14
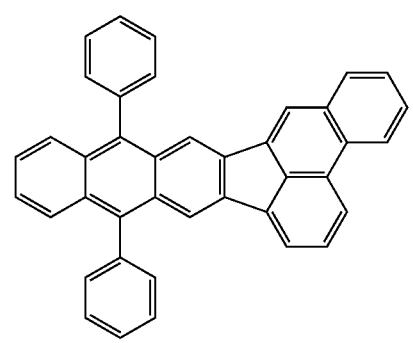

EM15

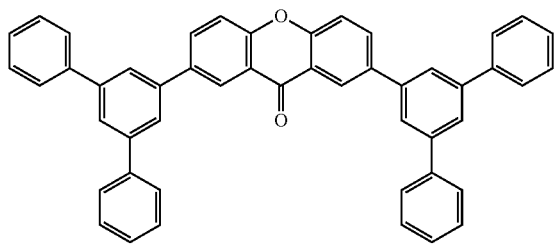

EM16

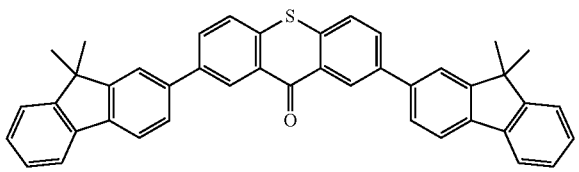

EM17

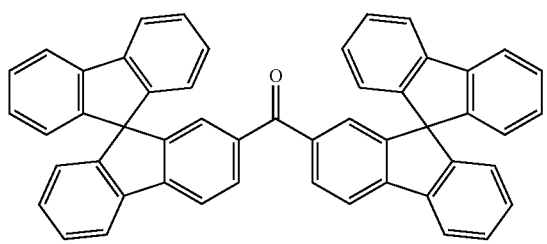

The electron-injectable/transportable material can be arbitrarily selected from materials that allow electrons to be easily injected from the cathode and can transport the injected electrons to the light-emitting layer in consideration of, for example, the balance with the hole mobility of the hole-transportable material. Examples of the material having electron-injecting performance and electron-transporting performance include an oxadiazole derivative, an oxazole derivative, a pyrazine derivative, a triazole derivative, a triazine derivative, a quinoline derivative, a quinoxaline derivative, a phenanthroline derivative, and an organic aluminum complex. Further, the electron-injectable/transportable material is suitably used for the hole-blocking layer as well.

Specific examples of a compound to be used as the electron-injectable/transportable material are shown below. However, the compound is of course not limited thereto.

ET2

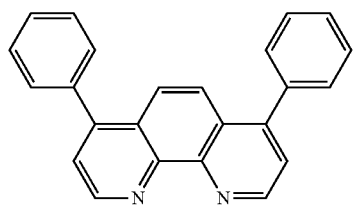

ET2

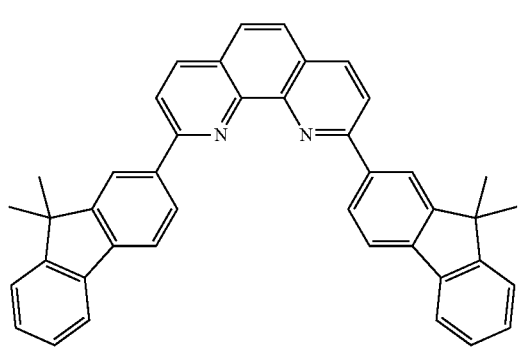

ET3

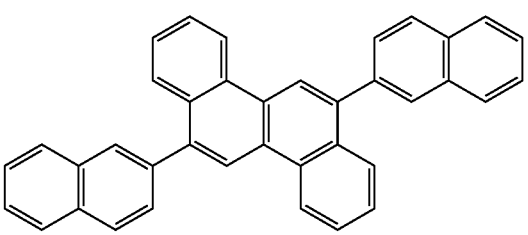

ET4

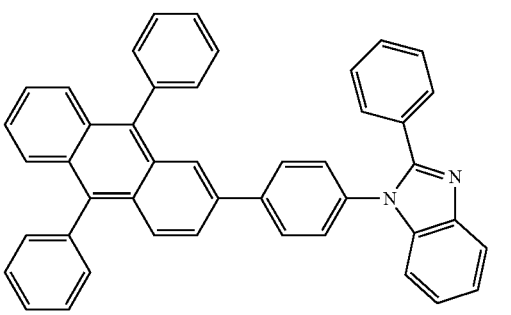

ET5

ET6

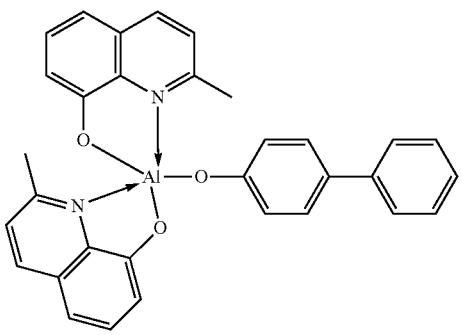

ET7

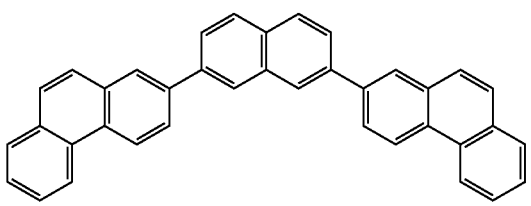

ET8

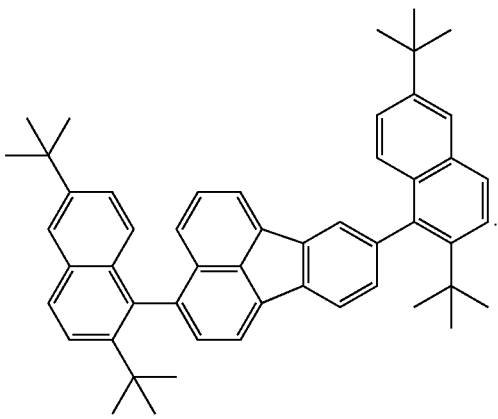

A constituent material for the anode desirably has as large a work function as possible. Examples thereof may include: metal simple substances such as gold, platinum, silver, copper, nickel, palladium, cobalt, selenium, vanadium, and tungsten or alloys obtained by combining those metal simple substances; metal oxides such as tin oxide, zinc oxide, indium oxide, indium tin oxide (ITO), and indium zinc oxide; and conductive polymers such as polyaniline, polypyrrole, and polythiophene.

One kind of those electrode substances may be used alone, or two or more kinds thereof may be used in combination. In addition, the anode may be of a single-layer construction or may be of a multilayer construction.

On the other hand, a constituent material for the cathode desirably has as small a work function as possible. Examples thereof include: alkali metals such as lithium; alkaline earth metals such as calcium; and metal simple substances such as aluminum, titanium, manganese, silver, lead, and chromium. Alternatively, alloys obtained by combining those metal simple substances can be used. For example, a magnesium-silver alloy, an aluminum-lithium alloy, or an aluminum-magnesium alloy can be used. A metal oxide such as indium tin oxide (ITO) can also be utilized. One kind of those electrode substances may be used alone, or two or more kinds thereof may be used in combination. In addition, the cathode may be of a single-layer construction or may be of a multilayer construction.

The organic compound layer (such as the hole-injecting layer, the hole-transporting layer, the electron-blocking layer, the light-emitting layer, the hole-blocking layer, the electron-transporting layer, or the electron-injecting layer) for forming the organic light-emitting element of the present invention is formed by the following method.

A dry process such as a vacuum vapor deposition method, an ionized vapor deposition method, sputtering, or a plasma process can be used for the formation of the organic compound layer for forming the organic light-emitting element of the present invention. In addition, a wet process involving dissolving the constituent materials in an appropriate solvent and forming a layer by a known application method (such as a spin coating method, a dipping method, a casting method, an LB method, or an ink jet method) can be used instead of the dry process.

Here, when the layer is formed by the vacuum vapor deposition method, the solution application method, or the like, the layer hardly undergoes crystallization or the like, and is excellent in stability over time. In addition, when the layer is formed by the application method, the film can be formed by using the constituent materials in combination with an appropriate binder resin.

Examples of the binder include, but not limited to, a polyvinyl carbazole resin, a polycarbonate resin, a polyester resin, an ABS resin, an acrylic resin, a polyimide resin, a phenol resin, an epoxy resin, a silicone resin, and a urea resin.

In addition, one kind of those binder resins may be used alone as a homopolymer or a copolymer, or two or more kinds thereof may be used as a mixture. Further, a known additive such as a plasticizer, an antioxidant, or a UV absorber may be used in combination as required.

(8) Application of Organic Light-Emitting Element of the Present Invention

The organic light-emitting element of the present invention can be used as a constituent member for a display apparatus or lighting apparatus. In addition, the element finds use in applications such as an exposure light source for an image-forming apparatus of an electrophotographic system, a backlight for a liquid crystal display apparatus, and a light-emitting apparatus including a white light source and a color filter. Examples of the color filter include filters that transmit light beams having three colors, i.e., red, green, and blue colors.

A display apparatus of the present invention includes the organic light-emitting element of the present invention in its display portion. It should be noted that the display portion includes multiple pixels.

In addition, the pixels each have the organic light-emitting element of the present invention and a transistor as an example of an active element (switching element) or amplifying element for controlling emission luminance, and the anode or cathode of the organic light-emitting element and the drain electrode or source electrode of the transistor are electrically connected to each other. Here, the display apparatus can be used as an image display apparatus for a PC or the like. The transistor is, for example, a TFT element and the TFT element is provided on, for example, the insulating surface of a substrate.

The display apparatus may be an information processing apparatus that includes an image input portion for inputting image information from, for example, an area CCD, a linear CCD, or a memory card, and displays an input image on its display portion.

In addition, the display portion of an imaging apparatus or inkjet printer may have a touch panel function. The drive system of the touch panel function is not particularly limited.

In addition, the display apparatus may be used in the display portion of a multifunction printer.

A lighting apparatus is an apparatus for lighting, for example, the inside of a room. The lighting apparatus may emit light having any one of the following colors: a white color (having a color temperature of 4,200 K), a daylight color (having a color temperature of 5,000 K), and colors ranging from blue to red colors.

A lighting apparatus of the present invention includes the organic light-emitting element of the present invention and an AC/DC converter circuit (circuit for converting an AC voltage into a DC voltage) connected to the organic light-emitting element. It should be noted that the lighting apparatus may further have a color filter.

An image-forming apparatus of the present invention is an image-forming apparatus including: a photosensitive member; a charging unit for charging the surface of the photosensitive member; a exposing unit for exposing the photosensitive member to form an electrostatic latent image; and a developing unit for developing the electrostatic latent image formed on the surface of the photosensitive member. Here, the exposing unit to be provided in the image-forming apparatus includes the organic light-emitting element of the present invention.

In addition, the organic light-emitting element of the present invention can be used as a constituent member for an exposing apparatus for exposing a photosensitive member. An exposing apparatus including a plurality of the organic light-emitting elements of the present invention is, for example, an exposing apparatus in which the organic light-emitting elements of the present invention are placed to form a line along a predetermined direction.

Next, the display apparatus of the present invention is described with reference to the drawing. FIG. 1 is a schematic sectional view illustrating an example of a display apparatus including an organic light-emitting element and a TFT element connected to the organic light-emitting element. It should be noted that the organic light-emitting element of the present invention is used as the organic light-emitting element constituting a display apparatus 1 of FIG. 1.

The display apparatus 1 of FIG. 1 includes a substrate 11 made of glass or the like and a moisture-proof film 12 for protecting a TFT element or organic compound layer, the film being provided on the substrate. In addition, a metal gate electrode 13 is represented by reference numeral 13, a gate insulating film 14 is represented by reference numeral 14, and a semiconductor layer is represented by reference numeral 15.

A TFT element 18 includes the semiconductor layer 15, a drain electrode 16, and a source electrode 17. An insulating film 19 is provided on the TFT element 18. An anode 21 constituting the organic light-emitting element and the source electrode 17 are connected to each other through a contact hole 20.

It should be noted that a system for the electrical connection between the electrode (anode or cathode) in the organic light-emitting element and the electrode (source electrode or drain electrode) in the TFT is not limited to the aspect illustrated in FIG. 1. In other words, one of the anode and the cathode, and one of the source electrode and drain electrode of the TFT element have only to be electrically connected to each other.

Although multiple organic compound layers are illustrated like one layer in the display apparatus 1 of FIG. 1, an organic compound layer 22 may be multiple layers. A first protective layer 24 and second protective layer 25 for suppressing the deterioration of the organic light-emitting element are provided on a cathode 23.

When the display apparatus 1 of FIG. 1 is a display apparatus that emits white light, a light-emitting layer in the organic compound layer 22 in FIG. 1 may be a layer obtained by mixing a red light-emitting material, a green light-emitting material, and a blue light-emitting material. In addition, the layer may be a laminated light-emitting layer obtained by laminating a layer formed of the red light-emitting material, a layer formed of the green light-emitting material, and a layer formed of the blue light-emitting material. Further, alternatively, the following aspect is permitted: the layer formed of the red light-emitting material, the layer formed of the green light-emitting material, and the layer formed of the blue light-emitting material are, for example, arranged side by side to form domains in one light-emitting layer.

Although the transistor is used as the switching element in the display apparatus 1 of FIG. 1, an MIM element may be used instead of the transistor as the switching element.

In addition, the transistor to be used in the display apparatus 1 of FIG. 1 is not limited to a transistor using a monocrystalline silicon wafer and may be a thin-film transistor including an active layer on the insulating surface of a substrate. A thin-film transistor using monocrystalline silicon as the active layer, a thin-film transistor using non-monocrystalline silicon such as amorphous silicon or microcrystalline silicon as the active layer, or a thin-film transistor using a non-monocrystalline oxide semiconductor such as an indium zinc oxide or an indium gallium zinc oxide as the active layer is also permitted. It should be noted that the thin-film transistor is also called a TFT element.

The transistor in the display apparatus 1 of FIG. 1 may be formed in a substrate such as an Si substrate. Here, the phrase "formed in a substrate" means that the transistor is produced by processing the substrate itself such as an Si substrate. In other words, the presence of the transistor in the substrate can be regarded as follows: the substrate and the transistor are integrally formed.

Whether the transistor is provided in the substrate is selected depending on definition. In the case of, for example, a definition of about a QVGA per inch, the organic light-emitting element is preferably provided in the Si substrate.

As described above, the driving of the display apparatus using the organic light-emitting element of the present invention enables display that has good image quality and is stable over a long time period.

EXAMPLES

Synthesis Examples 1 and 2

(Synthesis of Exemplified Compounds Ir-101 and Ir-201)

Ir-101 and Ir-201 were synthesized according to the following synthesis scheme with reference to, for example, Patent Literature 1 and Non Patent Literatures 1 to 3.

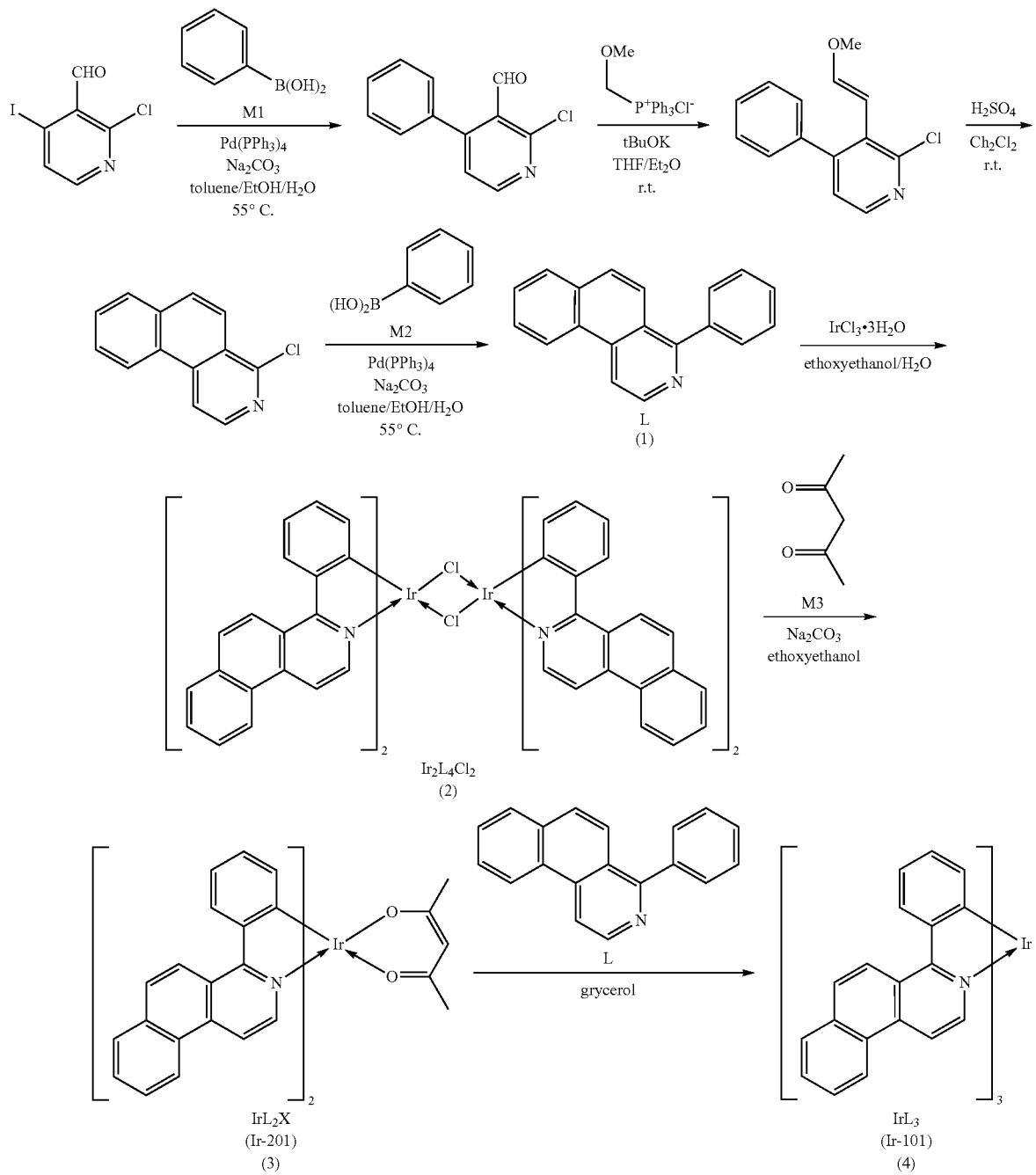

Specifically, the synthesis scheme is a synthesis process including the following steps:

(1) the synthesis of a ligand L (benzo[f]isoquinoline derivative);

(2) the synthesis of a chloro-bridged complex ($Ir_2L_4Cl_2$) having the ligand L;

(3) the synthesis of a complex ($IrL_2X$) having an auxiliary ligand X (the synthesis of Ir-201, Synthesis Example 1); and (4) the synthesis of a complex ($IrL_3$) to which the three ligands L's are coordinated (the synthesis of Ir-101, Synthesis Example 2).

Ir-101 and Ir-201 thus obtained were each identified by matrix-assisted laser desorption/ionization time-of-flight mass spectrometry (MALDI-TOF-MS). Further, the PL spectrum of each of the resultant iridium complexes in a toluene dilute solution having a concentration of $1\times10^{-5}$ M was measured with a UV-visible spectrophotometer (V-560 manufactured by JEOL Ltd.) and its maximum emission peak wavelength $\lambda_{max}$ was measured (excitation wavelength: 510 nm). Table 1 shows the results.

Synthesis Examples 3 to 16

Iridium complexes shown in Table 1 were each synthesized by the same synthesis method as that of Synthesis Examples 1 and 2 except that in the synthesis scheme of Synthesis Examples 1 and 2, the compounds (M1 to M3) serving as synthesis raw materials were appropriately changed. The structures of the resultant iridium complexes were confirmed by performing identification in the same manner as in the iridium complexes obtained in Synthesis Examples 1 and 2. In addition, their maximum emission peak wavelengths were measured by PL spectrum measurement. Table 1 shows the results.

Synthesis Example 17

(Synthesis of Exemplified Compound Ir-515)
Ir-515 was synthesized according to the following synthesis scheme with reference to, for example, Patent Literature 3.

tification in the same manner as in the iridium complexes obtained in Synthesis Examples 1 and 2. In addition, its maximum emission peak wavelength was measured by PL spectrum measurement. Table 1 shows the results.

TABLE 1

| | Ir complex | MS (calculated value) | MS (measured value) | $\lambda_{max}$ (nm) |
|---|---|---|---|---|
| Synthesis Example 1 | Ir-101 | 955.25 | 955.44 | 592 |
| Synthesis Example 2 | Ir-201 | 800.20 | 800.38 | 601 |
| Synthesis Example 3 | Ir-205 | 828.23 | 828.29 | 617 |

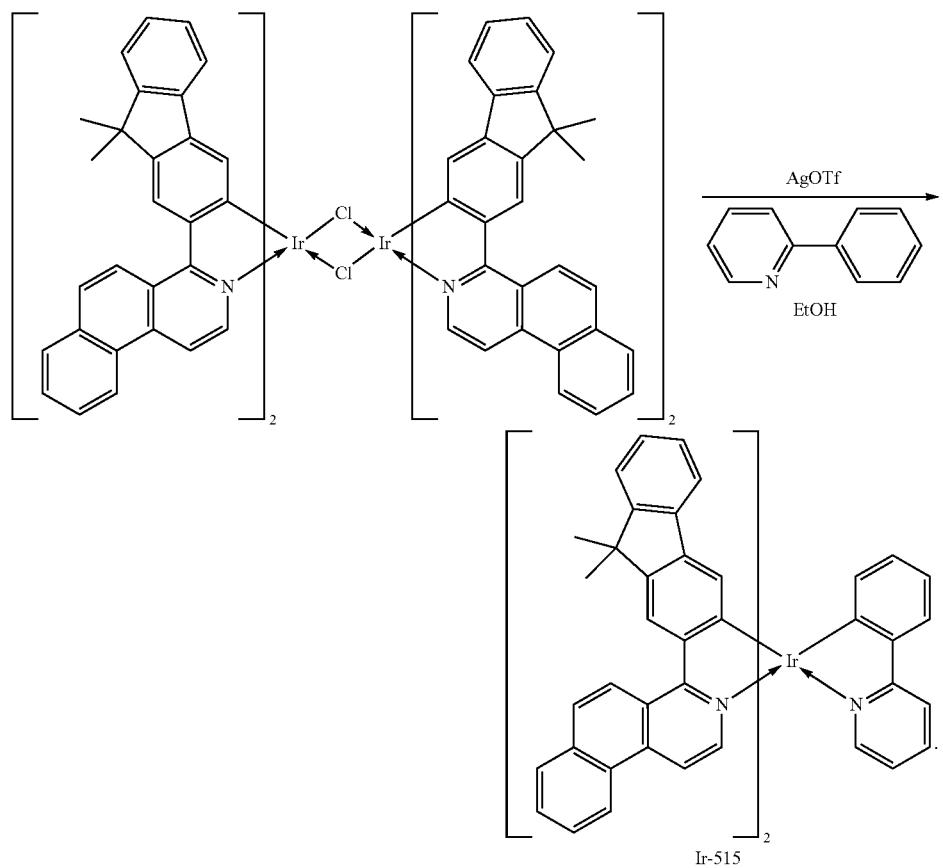

Ir-515

The structure of Ir-515 thus obtained was confirmed by performing identification in the same manner as in the iridium complexes obtained in Synthesis Examples 1 and 2. In addition, its maximum emission peak wavelength was measured by PL spectrum measurement. Table 1 shows the results.

Synthesis Example 18

(Synthesis of Exemplified Compound Ir-516)
Ir-516 was synthesized by the same synthesis method as that of Synthesis Example 17 except that in Synthesis Example 17, the loading amount of the auxiliary ligand (phenylpyridine) was appropriately regulated. The structure of Ir-516 thus obtained was confirmed by performing iden- TABLE 1-continued

| | Ir complex | MS (calculated value) | MS (measured value) | $\lambda_{max}$ (nm) |
|---|---|---|---|---|
| Synthesis Example 4 | Ir-206 | 912.33 | 912.56 | 614 |
| Synthesis Example 5 | Ir-212 | 856.26 | 856.45 | 614 |
| Synthesis Example 6 | Ir-213 | 940.36 | 940.85 | 614 |
| Synthesis Example 7 | Ir-214 | 1024.45 | 1025.80 | 612 |
| Synthesis Example 8 | Ir-221 | 912.33 | 912.23 | 621 |

TABLE 1-continued

| | Ir complex | MS (calculated value) | MS (measured value) | λ_max (nm) |
|---|---|---|---|---|
| Synthesis Example 9 | Ir-222 | 996.42 | 997.54 | 619 |
| Synthesis Example 10 | Ir-301 | 952.26 | 952.52 | 615 |
| Synthesis Example 11 | Ir-304 | 1064.39 | 1065.77 | 613 |
| Synthesis Example 12 | Ir-316 | 1036.36 | 1036.61 | 619 |
| Synthesis Example 13 | Ir-318 | 1148.48 | 1149.72 | 616 |
| Synthesis Example 14 | Ir-414 | 1012.36 | 1013.85 | 612 |
| Synthesis Example 15 | Ir-416 | 1032.33 | 1032.22 | 635 |
| Synthesis Example 16 | Ir-424 | 1276.36 | 1276.71 | 619 |

TABLE 1-continued

| | Ir complex | MS (calculated value) | MS (measured value) | λ_max (nm) |
|---|---|---|---|---|
| Synthesis Example 17 | Ir-515 | 1087.35 | 1087.34 | 623 |
| Synthesis Example 18 | Ir-516 | 871.25 | 817.17 | 624 |

Synthesis Examples 19 to 21

(Synthesis of Exemplified Compounds H-108, H-131, and H-139)

Exemplified Compounds H-108, H-131, and H-139 were each synthesized according to the following synthesis scheme with dibenzothiophen-4-ylboronic acid as a starting raw material by employing a cross-coupling reaction involving using a Pd catalyst.

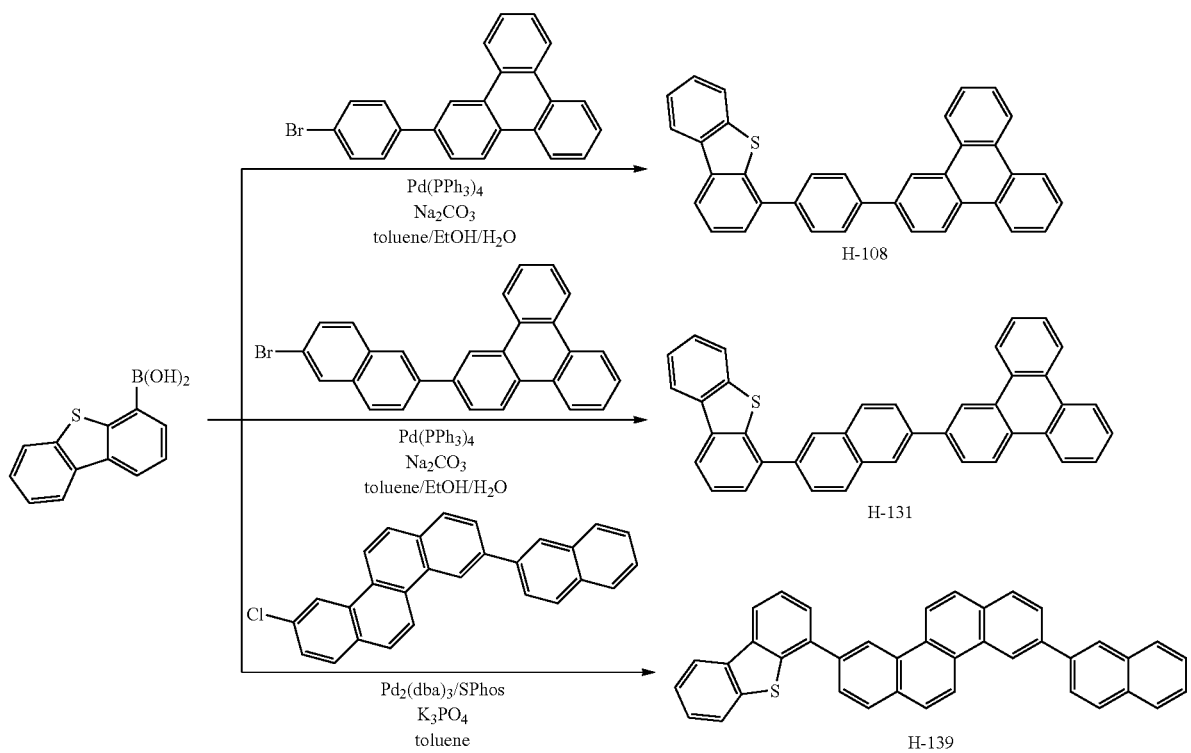

The resultant compounds (Exemplified Compounds H-108, H-131, and H-139) were identified by MALDI-TOF-MS. Table 2 shows the results.

Synthesis Examples 22 and 23

(Synthesis of Exemplified Compounds H-206 and H-210)

Exemplified Compounds H-206 and H-210 were each synthesized according to the following synthesis scheme by synthesizing benzo[b]naphtho[2,1-d]thiophen-10-boronic acid and then performing a cross-coupling reaction involving using a Pd catalyst.

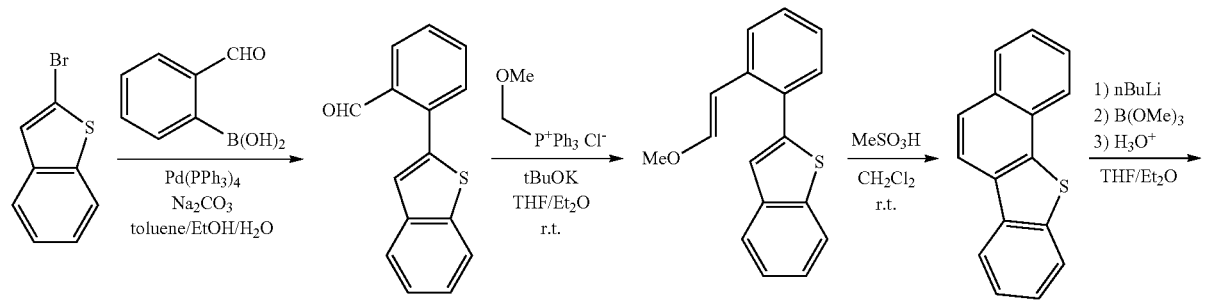

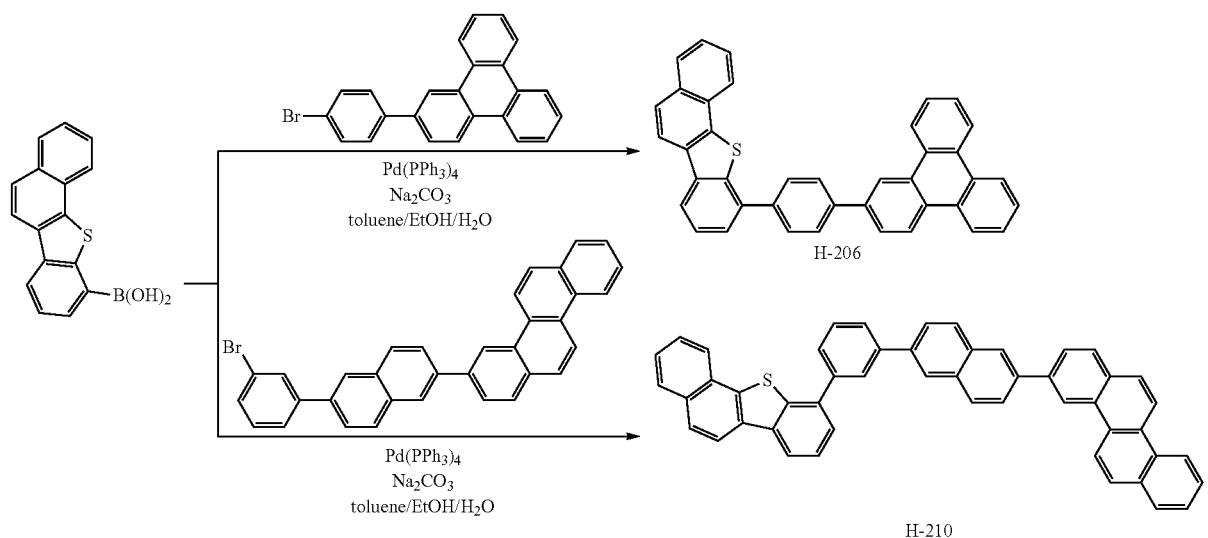

The resultant compounds (Exemplified Compounds H-206 and H-210) were identified by MALDI-TOF-MS. Table 2 shows the results.

Synthesis Examples 24 and 25

(Synthesis of Exemplified Compounds H-317 and H-322)
Exemplified Compounds H-317 and H-322 were each synthesized according to the following synthesis scheme by synthesizing 2-chlorobenzo[b]phenanthro[3,4-d]thiophene and then performing a cross-coupling reaction involving using a Pd catalyst.

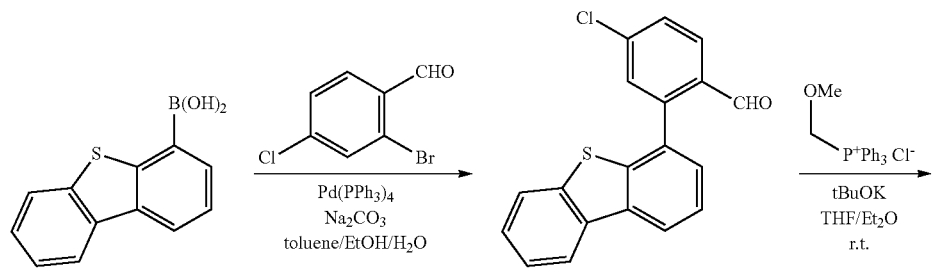

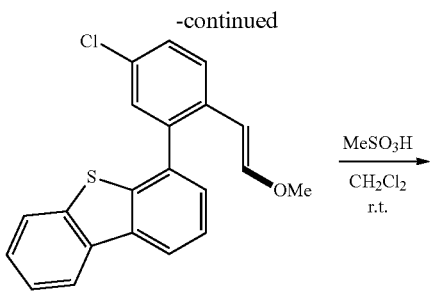

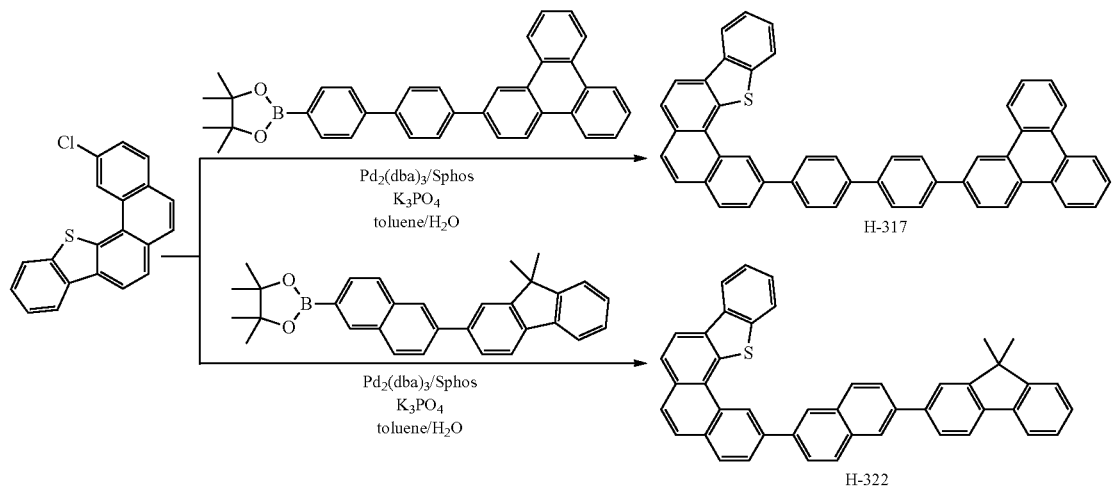

The resultant compounds (Exemplified Compounds H-317 and H-322) were identified by MALDI-TOF-MS. Table 2 shows the results.

Synthesis Examples 26 to 28

(Synthesis of Exemplified Compounds H-401, H-422, and H-424)

Dibenzo[b,mn]xanthen-7-ylboronic acid was synthesized according to the following synthesis scheme with reference to Non Patent Literature 4. Subsequently, Exemplified Compounds H-401, H-422, and H-424 were each synthesized by performing a cross-coupling reaction involving using a Pd catalyst.

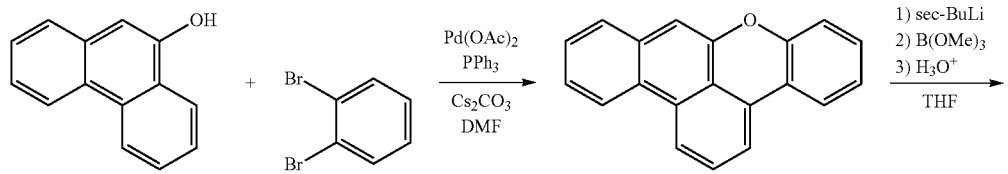

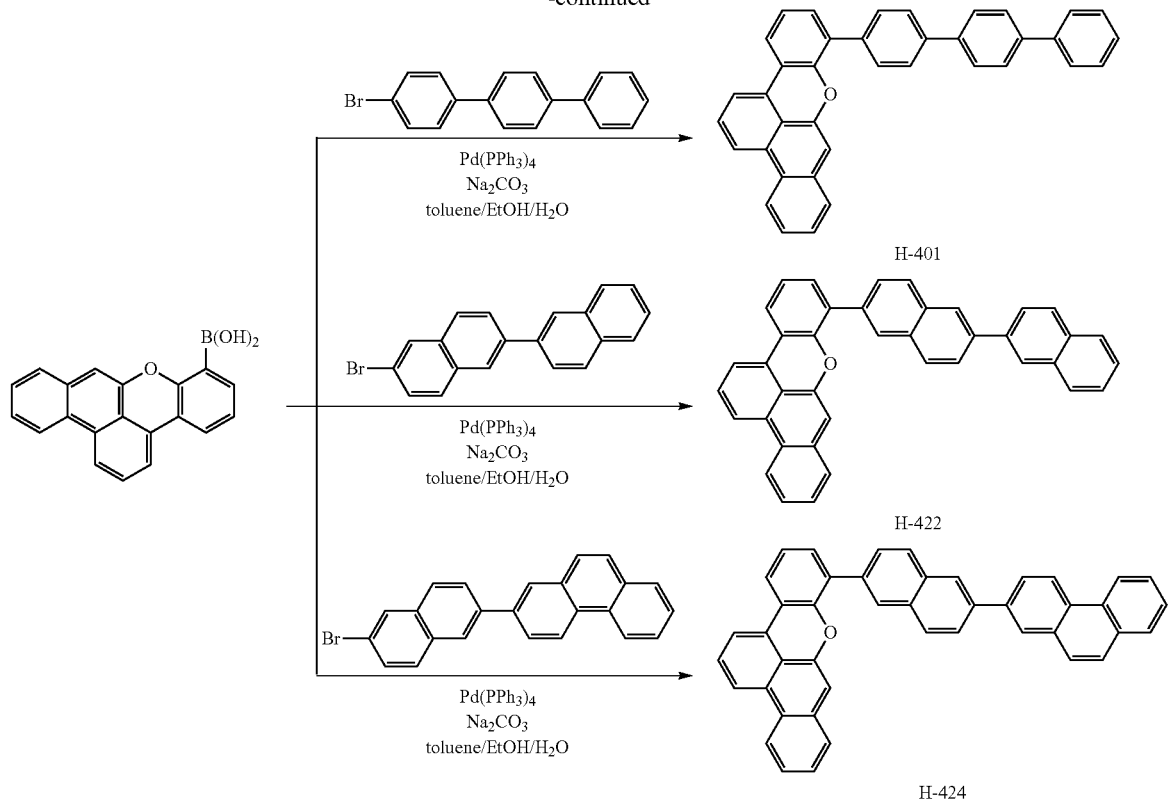

The resultant compounds (Exemplified Compounds H-401, H-422, and H-424) were identified by MALDI-TOF-MS. Table 2 shows the results.

Synthesis Example 29

(Synthesis of Exemplified Compound H-439)

Exemplified Compound H-439 was synthesized by the same method as that of Synthesis Example 27 except that in Synthesis Example 27, the starting raw material was changed from 9-hydroxyphenanthrene to 3,6-dimethylphenanthren-9-ol. The resultant compound (Exemplified Compound H-439) was identified by MALDI-TOF-MS. Table 2 shows the result.

Synthesis Examples 30 to 32

(Synthesis of Exemplified Compounds H-507, H-508, and H-509)

Exemplified Compounds H-507, H-508, and H-509 were each synthesized according to the following synthesis scheme by synthesizing 5-chlorodibenzo[b,mn]xanthene and then performing a cross-coupling reaction involving using a Pd catalyst.

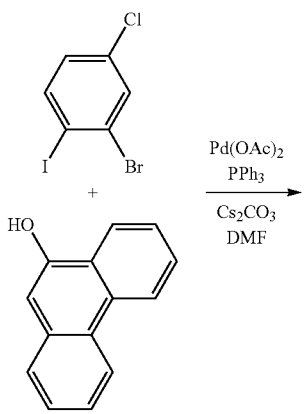

-continued

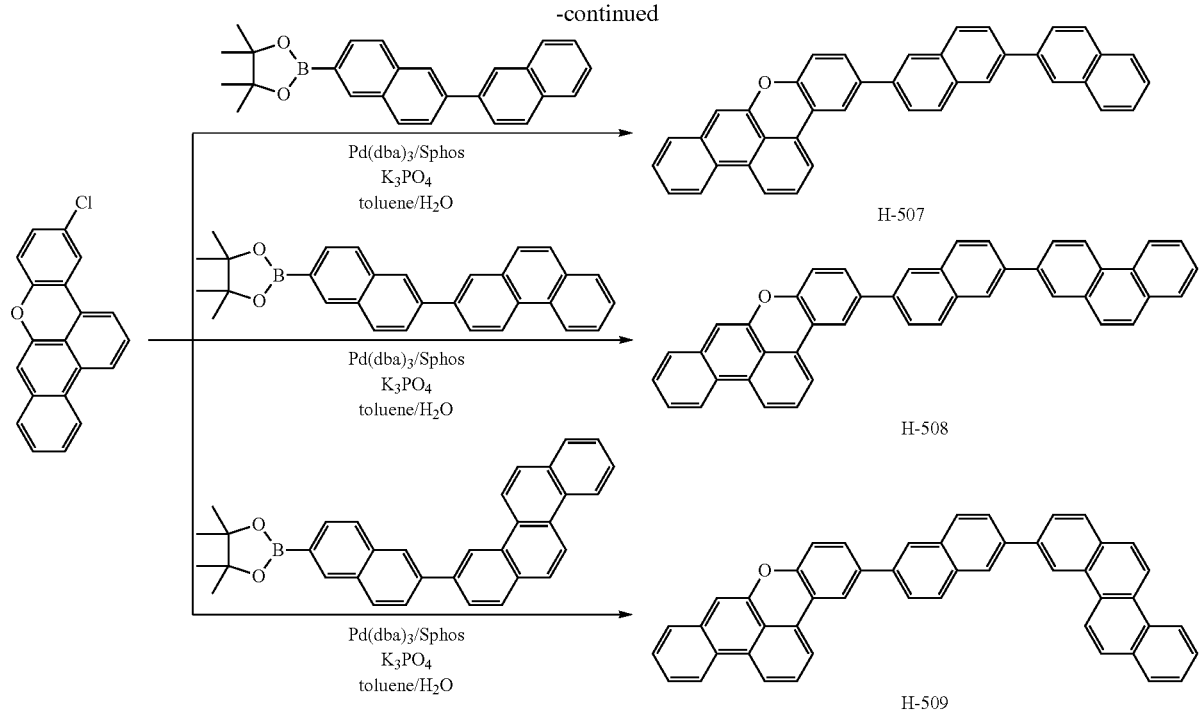

The resultant compounds (Exemplified Compounds H-507, H-508, and H-509) were identified by MALDI-TOF-MS. Table 2 shows the results.

Synthesis Example 33

(Synthesis of Exemplified Compound H-629)

Exemplified Compound H-629 was synthesized by the same method as that of Synthesis Example 22 except that in Synthesis Example 22, the starting raw material was changed from 2-bromobenzo[b]thiophene to 2-bromobenzofuran.

The resultant compound (Exemplified Compound H-629) was identified by MALDI-TOF-MS. Table 2 shows the result.

Synthesis Example 34

(Synthesis of Exemplified Compound H-712)

Exemplified Compound H-712 was synthesized according to the following synthesis scheme.

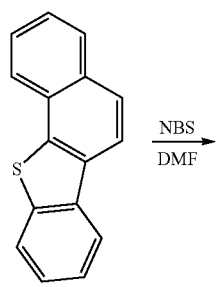

-continued

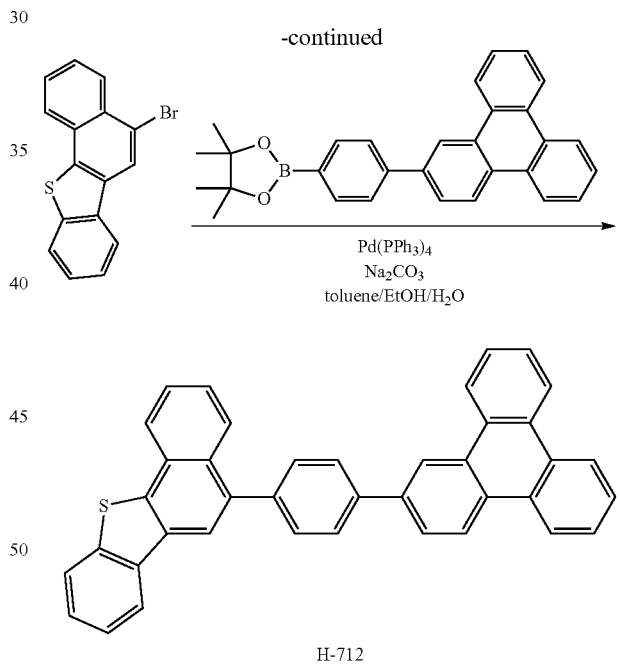

Specifically, 5-bromobenzo[b]naphtho[2,1-d]thiophene was synthesized from benzo[b]naphtho[2,1-d]thiophene obtained as an intermediate in Synthesis Examples 22 and 23 with reference to Patent Literature 4.

Subsequently, Exemplified Compound H-712 was synthesized by performing a cross-coupling reaction involving a Pd catalyst.

The resultant compound (Exemplified Compound H-712) was identified by MALDI-TOF-MS. Table 2 shows the result.

TABLE 2

| | Exemplified Compound | MS (calculated value) | MS (measured value) |
|---|---|---|---|
| Synthesis Example 19 | H-108 | 486.14 | 486.33 |
| Synthesis Example 20 | H-131 | 536.16 | 536.31 |
| Synthesis Example 21 | H-139 | 536.16 | 536.28 |
| Synthesis Example 22 | H-206 | 536.16 | 536.35 |
| Synthesis Example 23 | H-210 | 662.21 | 662.39 |
| Synthesis Example 24 | H-317 | 662.21 | 662.42 |
| Synthesis Example 25 | H-322 | 602.21 | 602.41 |
| Synthesis Example 26 | H-401 | 496.18 | 496.38 |
| Synthesis Example 27 | H-422 | 520.18 | 520.35 |
| Synthesis Example 28 | H-424 | 570.20 | 570.43 |
| Synthesis Example 29 | H-439 | 548.21 | 548.40 |
| Synthesis Example 30 | H-507 | 520.18 | 520.35 |
| Synthesis Example 31 | H-508 | 570.20 | 570.42 |
| Synthesis Example 32 | H-509 | 620.21 | 620.35 |
| Synthesis Example 33 | H-629 | 520.18 | 520.36 |
| Synthesis Example 34 | H-712 | 536.16 | 536.33 |

Example 1

In this example, an organic light-emitting element having a construction in which "an anode/a hole-transporting layer/an electron-blocking layer/a light-emitting layer/a hole-blocking layer/an electron-transporting layer/a cathode" were formed on a substrate in the stated order was produced by the following method.

First, ITO was formed into a film on a glass substrate and then subjected to desired patterning processing to form an ITO electrode (anode). At this time, the thickness of the ITO electrode was set to 100 nm. The substrate on which the ITO electrode had been thus formed was used as an ITO substrate in the following steps.

An organic light-emitting element was obtained by continuously forming, on the ITO substrate, organic compound layers and electrode layers shown in Table 3 below. It should be noted that at this time, the electrode area of the opposing electrode (metal electrode layers, cathode) was set to 3 mm$^2$.

TABLE 3

| | Material | Thickness [nm] |
|---|---|---|
| Hole-transporting layer: HTL | HT-2 | 40 |
| Electron-blocking layer: EBL | HT-7 | 10 |
| Light-emitting layer host: HOST guest: GUEST | H-108 (HOST) Ir-205 (GUEST) (H-108:Ir-205 = 96:4 (weight ratio)) | 30 |
| Hole-blocking layer: HBL | ET-3 | 10 |
| Electron-transporting layer: ETL | ET-2 | 50 |
| First metal electrode layer | LiF | 0.5 |
| Second metal electrode layer | Al | 100 |

The characteristics of the resultant element were measured and evaluated by measuring its current-voltage characteristics with a microammeter 4140B manufactured by Hewlett-Packard Company and measuring its emission luminance with a BM-7 manufactured by TOPCON CORPORATION. In this example, the light-emitting element had a maximum luminous wavelength of 619 nm and chromaticity coordinates (x, y) of (0.66, 0.34).

As a result, luminous efficiency in the case where the organic light-emitting element of this example was caused to emit light with its luminance set to 2,000 cd/m$^2$ was 23.8 cd/A. In addition, the luminance half lifetime of the organic light-emitting element of this example at a current value of 100 mA/cm$^2$ was 400 hours.

Examples 2 to 26 and Comparative Examples 1 to 9

Organic light-emitting elements were each produced by the same method as that of Example 1 except that in Example 1, the compounds used as the hole-transporting layer (HTL), the electron-blocking layer (EBL), the light-emitting layer host (HOST), the light-emitting layer guest (GUEST), the hole-blocking layer (HBL), and the electron-transporting layer (ETL) were appropriately changed to compounds shown in Table 4 below. The characteristics of the resultant elements were measured and evaluated in the same manner as in Example 1. Table 4 shows the results of the measurement.

TABLE 4

| | HTL | EBL | HOST | GUEST | HBL | ETL | Luminous efficiency at 2,000 cd/m$^2$ [cd/A] | Half lifetime at 100 mA/cm$^2$ [h] |
|---|---|---|---|---|---|---|---|---|
| Example 1 | HT2 | HT7 | H-108 | Ir-205 | ET-3 | ET-2 | 23.8 | 400 |
| Example 2 | HT2 | HT7 | H-108 | Ir-301 | ET-3 | ET-2 | 21.3 | 440 |
| Example 3 | HT1 | HT8 | H-108 | Ir-414 | ET-3 | ET-2 | 21.2 | 370 |
| Example 4 | HT1 | HT8 | H-108 | Ir-515 | ET-3 | ET-2 | 21.9 | 320 |
| Example 5 | HT1 | HT7 | H-131 | Ir-101 | ET-3 | ET-2 | 24.8 | 770 |
| Example 6 | HT1 | HT7 | H-131 | Ir-213 | ET-4 | ET-2 | 23.5 | 360 |
| Example 7 | HT1 | HT7 | H-131 | Ir-316 | ET-4 | ET-1 | 23.2 | 280 |
| Example 8 | HT2 | HT8 | H-206 | Ir-205 | ET-3 | ET-2 | 23.9 | 450 |
| Example 9 | HT2 | HT7 | H-210 | Ir-318 | ET-3 | ET-2 | 22.5 | 300 |
| Example 10 | HT2 | HT7 | H-322 | Ir-213 | ET-4 | ET-2 | 24.1 | 410 |
| Example 11 | HT2 | HT11 | H-322 | Ir-318 | ET-4 | ET-1 | 22.6 | 270 |
| Example 12 | HT2 | HT7 | H-322 | Ir-416 | ET-3 | ET-1 | 21.8 | 320 |
| Example 13 | HT1 | HT8 | H-401 | Ir-212 | ET-3 | ET-2 | 24.1 | 430 |
| Example 14 | HT1 | HT7 | H-401 | Ir-304 | ET-4 | ET-2 | 24.9 | 560 |

TABLE 4-continued

|  | HTL | EBL | HOST | GUEST | HBL | ETL | Luminous efficiency at 2,000 cd/m$^2$ [cd/A] | Half lifetime at 100 mA/cm$^2$ [h] |
|---|---|---|---|---|---|---|---|---|
| Example 15 | HT2 | HT8 | H-422 | Ir-101 | ET-3 | ET-2 | 24.7 | 790 |
| Example 16 | HT2 | HT7 | H-422 | Ir-205 | ET-3 | ET-2 | 24.2 | 430 |
| Example 17 | HT2 | HT7 | H-424 | Ir-206 | ET-3 | ET-2 | 24.1 | 360 |
| Example 18 | HT2 | HT8 | H-424 | Ir-304 | ET-3 | ET-2 | 25.0 | 630 |
| Example 19 | HT2 | HT8 | H-424 | Ir-316 | ET-4 | ET-2 | 23.0 | 340 |
| Example 20 | HT2 | HT7 | H-424 | Ir-424 | ET-7 | ET-2 | 21.0 | 320 |
| Example 21 | HT1 | HT7 | H-507 | Ir-205 | ET-3 | ET-2 | 24.2 | 500 |
| Example 22 | HT1 | HT11 | H-508 | Ir-301 | ET-3 | ET-1 | 22.0 | 590 |
| Example 23 | HT1 | HT7 | H-509 | Ir-424 | ET-3 | ET-2 | 21.4 | 350 |
| Example 24 | HT1 | HT8 | H-629 | Ir-222 | ET-3 | ET-2 | 24.4 | 300 |
| Example 25 | HT2 | HT7 | H-712 | Ir-212 | ET-4 | ET-2 | 24.2 | 400 |
| Example 26 | HT3 | HT7 | H-712 | Ir-516 | ET-4 | ET-2 | 22.2 | 320 |
| Comparative Example 1 | HT1 | HT8 | EM8 | Ir-101 | ET-3 | ET-2 | 24.8 | 120 |
| Comparative Example 2 | HT1 | HT7 | EM8 | Ir-205 | ET-3 | ET-2 | 23.8 | 70 |
| Comparative Example 3 | HT2 | HT7 | EM9 | Ir-206 | ET-4 | ET-2 | 23.9 | 150 |
| Comparative Example 4 | HT2 | HT7 | EM8 | Ir-301 | ET-4 | ET-2 | 21.5 | 90 |
| Comparative Example 5 | HT2 | HT7 | EM 9 | Ir-318 | ET-3 | ET-2 | 22.1 | 110 |
| Comparative Example 6 | HT2 | HT7 | H-108 | RD5 | ET-4 | ET-2 | 13.2 | 370 |
| Comparative Example 7 | HT2 | HT7 | H-131 | RD3 | ET-3 | ET-2 | 7.8 | 360 |
| Comparative Example 8 | HT2 | HT8 | H-424 | RD5 | ET-3 | ET-2 | 13.3 | 410 |
| Comparative Example 9 | HT2 | HT8 | EM8 | RD5 | ET-3 | ET-1 | 12.6 | 80 |

The organic light-emitting elements of Comparative Examples 1 to 5 had shorter luminance half lifetimes than those of the organic light-emitting elements of Examples, though the former elements were each substantially comparable to the latter elements in luminous efficiency. This is caused by the fact that the host in the light-emitting layer is not the heterocycle-containing compound represented by the general formula [5]. Therefore, the heterocycle-containing compound represented by the general formula [5] used as a host for the light-emitting layer in the organic light-emitting element of the present invention is a compound having high structural stability and moderate hole-transporting property. Accordingly, the organic light-emitting element of the present invention was found to have high luminous efficiency and a long luminance half lifetime.

On the other hand, the light-emitting elements used in Comparative Examples 6 to 8 had lower luminous efficiencies than those of the organic light-emitting elements of Examples, though the former elements were each substantially comparable to the latter elements in luminance half lifetime. This is caused by the fact that the guest in the light-emitting layer is not the big-based Ir complex represented by the general formula [1]. Therefore, an organic light-emitting element improved in luminous efficiency and luminance half lifetime is obtained only when the heterocycle-containing compound represented by the general formula [5] having a lifetime-lengthening effect and the big-based Ir complex represented by the general formula [1] having high luminous efficiency are combined like the organic light-emitting elements of Examples.

Example 27

In this example, an organic light-emitting element having a construction in which "an anode/a hole-transporting layer/an electron-blocking layer/a light-emitting layer/a hole-blocking layer/an electron-transporting layer/a cathode" were formed on a substrate in the stated order was produced. It should be noted that in this example, the light-emitting layer contains an assist material.

First, organic compound layers and electrode layers shown in Table 5 below were continuously formed on an ITO substrate that had been produced by the same method as that of Example 1. It should be noted that at this time, the electrode area of the opposing electrode (metal electrode layers, cathode) was set to 3 mm$^2$.

TABLE 5

| Material | Thickness (nm) |
|---|---|
| Hole-transporting layer: HTL | HT-2 | 40 |
| Electron-blocking layer: EBL | HT-7 | 10 |
| Light-emitting layer host: | H-108 (HOST) | 30 |
| HOST | HT-2 (ASSIST) | |
| ASSIST | Ir-222 (GUEST) | |
| GUEST | (H-108:HT-2:Ir-222 = 80:15:5 (weight ratio)) | |
| Hole-blocking layer: HBL | ET-3 | 10 |
| Electron-transporting layer: ETL | ET-1 | 50 |
| First metal electrode layer | LiF | 0.5 |
| Second metal electrode layer | Al | 100 |

The characteristics of the resultant element were measured and evaluated in the same manner as in Example 1. Here, the organic light-emitting element of this example had a maximum luminous wavelength of 621 nm and chromaticity coordinates (x, y) of (0.66, 0.34). In addition, the element had a luminous efficiency at the time of its light emission at a luminance of 1,500 cd/m$^2$ of 24.7 cd/A and a luminance half lifetime at a current value of 100 mA/cm$^G$ of 210 hours.

Examples 28 to 34 and Comparative Examples 10 to 12

Organic light-emitting elements were each produced by the same method as that of Example 27 except that in Example 27, the compounds used as the hole-transporting layer (HTL), the electron-blocking layer (EBL), the light-emitting layer host (HOST), the light-emitting layer assist (ASSIST), the light-emitting layer guest (GUEST), the hole-blocking layer (HBL), and the electron-transporting layer (ETL) were changed as shown in Table 6. The characteristics of the resultant elements were measured and evaluated in the same manner as in Example 27. Table 6 shows the results of the measurement.

TABLE 6

|  | HTL | EBL | HOST | ASSIST | GUEST | HBL | ETL | Luminous efficiency at 1,500 cd/m$^2$ [cd/A] | Half lifetime at 100 mA/cm$^2$ [h] |
| --- | --- | --- | --- | --- | --- | --- | --- | --- | --- |
| Example 27 | HT2 | HT7 | H-108 | HT2 | Ir-222 | ET-3 | ET-1 | 24.7 | 210 |
| Example 28 | HT1 | HT8 | H-139 | GD6 | Ir-205 | ET-3 | ET-2 | 23.9 | 430 |
| Example 29 | HT2 | HT7 | H-206 | HT2 | Ir-222 | ET-3 | ET-2 | 24.8 | 230 |
| Example 30 | HT2 | HT11 | H-210 | GD6 | Ir-206 | ET-4 | ET-1 | 24.1 | 490 |
| Example 31 | HT2 | HT7 | H-317 | GD6 | Ir-214 | ET-7 | ET-2 | 23.6 | 410 |
| Example 32 | HT2 | HT7 | H-424 | GD6 | Ir-221 | ET-3 | ET-2 | 24.0 | 360 |
| Example 33 | HT3 | HT8 | H-439 | HT1 | Ir-301 | ET-4 | ET-2 | 22.4 | 390 |
| Example 34 | HT2 | HT7 | H-507 | HT2 | Ir-316 | ET-3 | ET-2 | 23.2 | 200 |
| Comparative Example 10 | HT2 | HT7 | EM8 | GD6 | Ir-206 | ET-3 | ET-1 | 23.9 | 90 |
| Comparative Example 11 | HT1 | HT8 | EM9 | HT2 | Ir-304 | ET-3 | ET-2 | 23.7 | 140 |
| Comparative Example 12 | HT2 | HT8 | H-108 | GD6 | RD5 | ET-4 | ET-2 | 14.0 | 560 |

Examples 27 to 34 showed that even when part of the host in the light-emitting layer was changed to the assist material, an organic light-emitting element having high luminous efficiency and a long lifetime was obtained as in Examples 1 to 26.

On the other hand, the organic light-emitting elements of Comparative Examples 10 and 11 each had a shorter luminance half lifetime than those of Examples even when the assist material was incorporated into the light-emitting layer because the host in the light-emitting layer was not the heterocycle-containing compound represented by the general formula [5].

In addition, the organic light-emitting element of Comparative Example 12 had a lower luminous efficiency than those of Examples even when the assist material was incorporated into the light-emitting layer because the guest in the light-emitting layer was not the biq-based Ir complex represented by the general formula [1].

The foregoing showed that even in the case where the assist material was incorporated into the light-emitting layer, an organic light-emitting element having high luminous efficiency and a long luminance half lifetime was obtained only when the heterocycle-containing compound represented by the general formula [5] and the biq-based Ir complex represented by the general formula [1] were combined.

As described above with reference to the embodiments and Examples, according to one embodiment of the present invention, it is possible to provide the organic light-emitting element improved in luminous efficiency and lifetime.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-285619, filed on Dec. 27, 2012, which is hereby incorporated by reference herein in its entirety.

The invention claimed is:
1. An organic light-emitting element comprising:
a pair of electrodes; and
an organic compound layer placed between the pair of electrodes,
wherein the organic compound layer has an iridium complex represented by the following general formula [1] and a heterocycle-containing compound represented by the following general formula [5]:

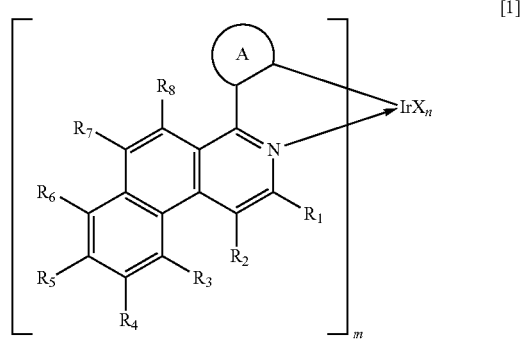

in the formula [1]:
R$_1$ to R$_8$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group;
m represents an integer of 1 to 3 and n represents an integer of 0 to 2, provided that m+n equals 3;
a ring A represents a cyclic structure selected from a benzene ring, a naphthalene ring, a fluorene ring, a phenanthrene ring, and a 9,9-spirobifluorene ring, and is covalently bonded to a benzo[f]isoquinoline skeleton and an Ir metal, and the ring A may further have a substituent;

X represents a bidentate ligand; and a partial structure $IrX_n$ comprises any one of structures represented by the following general formulae [2] to [4]:

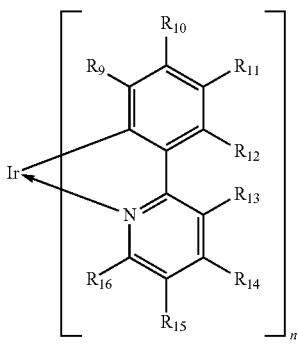

[2]

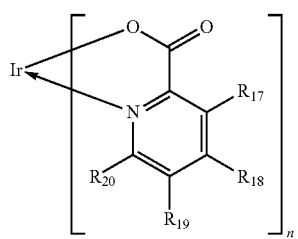

[3]

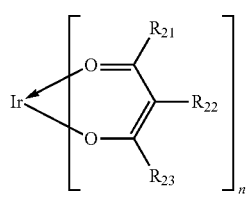

[4]

in the formulae [2] to [4]:

$R_9$ to $R_{23}$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group,

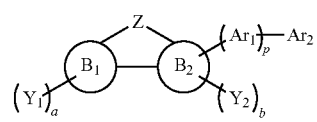

[5]

in the formula [5]:

Z represents an oxygen atom or a sulfur atom;

a ring including Z is a five- or six-membered ring;

a ring $B_1$ and a ring $B_2$ each represent a cyclic structure selected from a benzene ring, a naphthalene ring, a phenanthrene ring, a triphenylene ring, and a chrysene ring, and may be identical to or different from each other;

$Y_1$ and $Y_2$ each represent an alkyl group, or a substituted or unsubstituted aromatic hydrocarbon group;

a represents an integer of 0 to 4, and when a represents 2 or more, multiple $Y_1$'s may be identical to or different from each other;

b represents an integer of 0 to 4, provided that when the ring $B_2$ represents a benzene ring, b represents an integer of 0 to 3, and when b represents 2 or more, multiple $Y_2$'s may be identical to or different from each other;

$Ar_1$ represents a substituted or unsubstituted divalent aromatic hydrocarbon group;

$Ar_2$ represents a substituted or unsubstituted monovalent aromatic hydrocarbon group; and p represents an integer of 0 to 4, and when p represents 2 or more, multiple $Ar_1$'s may be identical to or different from each other, wherein when:

(a) both of $B_1$ and $B_2$ are benzene rings, (b) Z is a sulfur atom, and (c) the ring including Z is a five-membered ring, then p is not 0, and the $Ar_1$ is selected from the group consisting of a naphthalenediyl group, a phenanthrenediyl group, an anthracenediyl group, a benzo[a]anthracenediyl group, a fluorenediyl group, a benzo[a]fluorenediyl group, a benzo[b]fluorenediyl group, a benzo[c]fluorenediyl group, a dibenzo[a,c]fluorenediyl group, a dibenzo[b,h]fluorenediyl group, a dibenzo[c,g]fluorenediyl group, an acenaphthylenediyl group, a chrysenediyl group, a benzo[b]chrysenediyl group, a pyrenediyl group, a benzo[e]pyrenediyl group, a triphenylenediyl group, a benzo[a]triphenylenediyl group, a benzo[b]triphenylenediyl group, a picenediyl group, a fluoranthenediyl group, a benzo[a]fluoranthenediyl group, a benzo[b]fluoranthenediyl group, a benzo[j]fluoranthenediyl group, a benzo[k]fluoranthenediyl group, a perylenediyl group, and a naphthacenediyl group.

2. The organic light-emitting element according to claim 1, wherein m represents 2 and n represents 1.

3. The organic light-emitting element according to claim 1, wherein the iridium complex represented by the general formula [1] comprises a compound represented by the following general formula [6]:

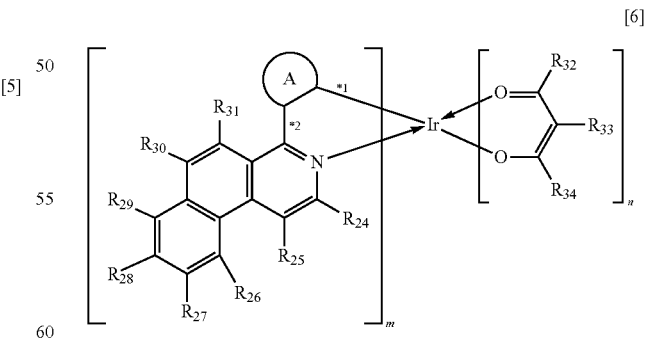

[6]

in the formula [6]:

$R_{24}$ to $R_{34}$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group;

m represents an integer of 1 to 3 and n represents an integer of 0 to 2, provided that m+n equals 3;

*1 represents a bond between the ring A and the Ir metal, and *2 represents a bond between the ring A and a carbon atom at a 4-position in the benzo[f] isoquinoline skeleton; and the ring A comprises any one of structures represented by the following general formulae [7] to [11]:

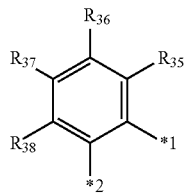
[7]

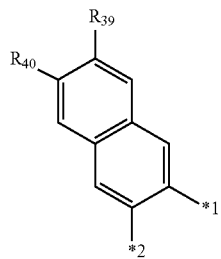
[8]

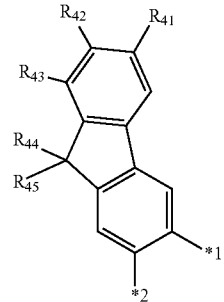
[9]

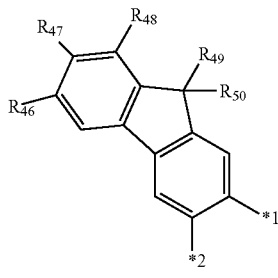
[10]

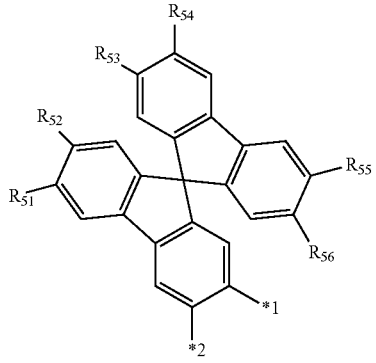
[11]

in the formulae [7] to [11]:

$R_{35}$ to $R_{56}$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group; and

*1 represents a bonding position with the Ir metal and *2 represents a bonding position with the carbon atom at the 4-position in the benzo[f]isoquinoline skeleton.

4. The organic light-emitting element according to claim 3, wherein the ring A comprises the structure represented by the general formula [7].

5. The organic light-emitting element according to claim 1, wherein in the heterocycle-containing compound represented by the general formula [5], a heterocycle formed of Z, the ring $B_1$, and the ring $B_2$ comprises any one of heterocycles represented by the following general formulae [12] to [19]:

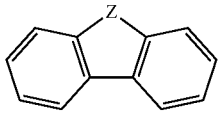
[12]

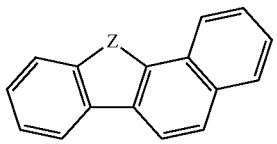
[13]

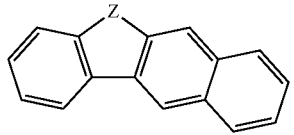
[14]

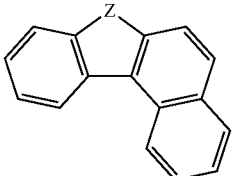
[15]

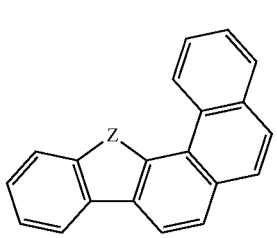
[16]

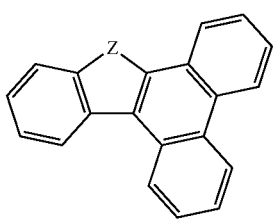
[17]

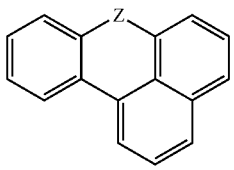

[18]

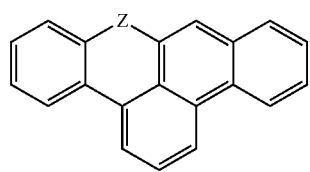

[19]

in the formulae [12] to [19], Z represents an oxygen atom or a sulfur atom.

6. The organic light-emitting element according to claim 1, wherein the iridium complex represented by the general formula [1] comprises an iridium complex represented by the following general formula [20]:

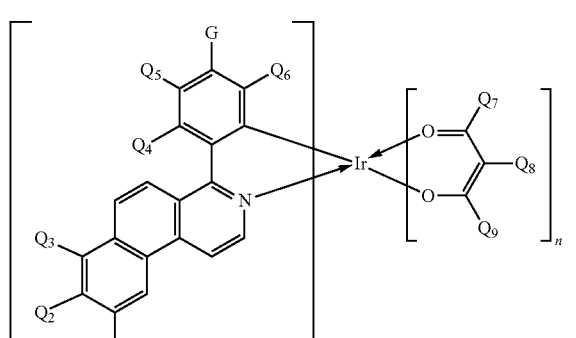

[20]

in the formula [20]:
Q$_1$ to Q$_9$ each represent a hydrogen atom, a halogen atom, an alkyl group, an alkoxy group, a trifluoromethyl group, or a cyano group; and G represents a hydrogen atom, a halogen atom, an alkyl group, an alkoxy group, a trifluoromethyl group, a cyano group, or a substituted or unsubstituted phenyl group.

7. The organic light-emitting element according to claim 1, wherein the heterocycle-containing compound represented by the general formula [5] comprises a dibenzothiophene compound represented by the following general formula [21]:

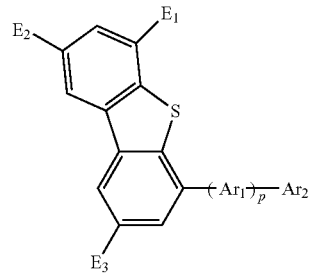

[21]

in the formula [21], E$_1$ to E$_3$ each represent a hydrogen atom, an alkyl group, or a substituted or unsubstituted aromatic hydrocarbon group.

8. The organic light-emitting element according to claim 7 wherein in the heterocycle-containing compounds represented by the general formulae [21] to [25]:
the p represents 1;
the Ar$_1$ represents a substituted or unsubstituted phenylene group, a substituted or unsubstituted biphenylene group, a substituted or unsubstituted terphenylene group, a substituted or unsubstituted naphthalenediyl group, a substituted or unsubstituted fluorenediyl group, a substituted or unsubstituted phenanthrenediyl group, a substituted or unsubstituted chrysenediyl group, or a substituted or unsubstituted triphenylenediyl group; and
the Ar$_2$ represents a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted phenanthrenyl group, a substituted or unsubstituted chrysenyl group, or a substituted or unsubstituted triphenylenyl group.

9. The organic light-emitting element according to claim 1, wherein the heterocycle-containing compound represented by the general formula [5] comprises a benzonaphthothiophene compound represented by the following general formula [22]:

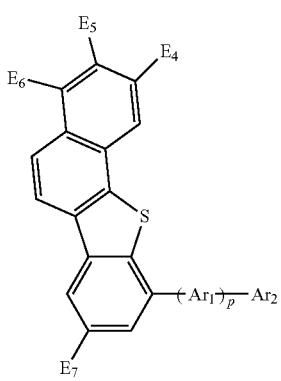

[22]

in the formula [22], E$_4$ to E$_7$ each represent a hydrogen atom, an alkyl group, or a substituted or unsubstituted aromatic hydrocarbon group.

10. The organic light-emitting element according to claim 1, wherein the heterocycle-containing compound represented by the general formula [5] comprises a benzophenan-throthiophene compound represented by the following general formula [23]:

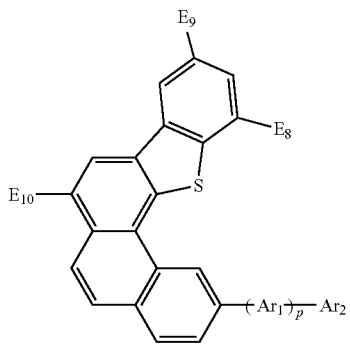

[23]

in the formula [23], $E_8$ to $E_{10}$ each represent a hydrogen atom, an alkyl group, or a substituted or unsubstituted aromatic hydrocarbon group.

11. The organic light-emitting element according to claim 1, wherein the heterocycle-containing compound represented by the general formula [5] comprises a dibenzoxanthene compound represented by the following general formula [24]:

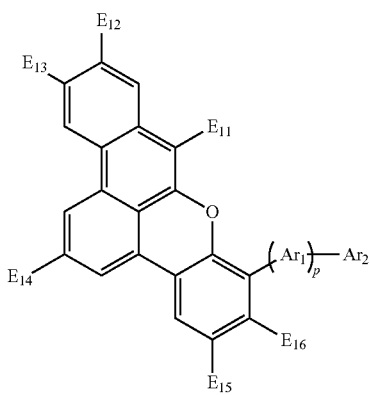

[24]

in the formula [24], $E_{11}$ to $E_{16}$ each represent a hydrogen atom, an alkyl group, or a substituted or unsubstituted aromatic hydrocarbon group.

12. The organic light-emitting element according to claim 1, wherein the heterocycle-containing compound represented by the general formula [5] comprises a dibenzoxanthene compound represented by the following general formula [25]:

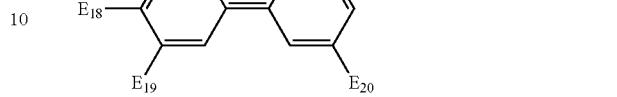

[25]

in the formula [25], $E_{17}$ to $E_{22}$ each represent a hydrogen atom, an alkyl group, or a substituted or unsubstituted aromatic hydrocarbon group.

13. The organic light-emitting element according to claim 1, wherein the organic compound layer comprises a light-emitting layer including a host and a guest;
the guest comprises the iridium complex represented by the general formula [1]; and
the host comprises the heterocycle-containing compound represented by the general formula [5].

14. The organic light-emitting element according to claim 13, wherein the organic compound layer further includes an assist material different from the host and the guest.

15. The organic light-emitting element according to claim 14, wherein the assist material comprises an iridium complex.

16. A display apparatus comprising multiple pixels, wherein each pixel has the organic light-emitting element according to claim 1 and an active element connected to the organic light-emitting element.

17. An information processing apparatus comprising:
a display portion for displaying an image; and
an input portion for inputting image information,
wherein the display portion comprises the display apparatus according to claim 16.

18. A lighting apparatus comprising:
the organic light-emitting element according to claim 1; and
an AC/DC converter circuit connected to the organic light-emitting element.

19. An image-forming apparatus comprising:
a photosensitive member;
a charging unit for charging a surface of the photosensitive member;
an exposing unit for exposing the photosensitive member to form an electrostatic latent image; and
a developing unit for developing the electrostatic latent image formed on the surface of the photosensitive member,
wherein the exposing unit includes the organic light-emitting element according to claim 1.

20. An exposing apparatus for exposing a photosensitive member comprising a plurality of the organic light-emitting elements according to claim 1, wherein the organic light-emitting elements are placed to form a line along a predetermined direction.

* * * * *